(12) United States Patent
 de la Huerga

(10) Patent No.: US 7,922,073 B2
(45) Date of Patent: Apr. 12, 2011

(54) VIAL PRINTING METHOD AND APPARATUS

(76) Inventor: Carlos de la Huerga, Milwaukee, WI (US)

( * ) Notice: Subject to any disclaimer, the term of this patent is extended or adjusted under 35 U.S.C. 154(b) by 840 days.

(21) Appl. No.: 11/800,792

(22) Filed: May 7, 2007

(65) Prior Publication Data

US 2007/0204497 A1     Sep. 6, 2007

Related U.S. Application Data

(63) Continuation-in-part of application No. 09/426,553, filed on Oct. 22, 1999, now Pat. No. 7,216,802, which is a continuation-in-part of application No. 08/955,475, filed on Oct. 21, 1997, now Pat. No. 6,032,155.

(51) Int. Cl.
 *G06F 17/00*     (2006.01)
(52) U.S. Cl. ........................................ 235/375; 235/380

(58) Field of Classification Search .................. 235/494, 235/492, 380, 375
 See application file for complete search history.

(56) References Cited

U.S. PATENT DOCUMENTS

2008/0303265 A1* 12/2008 Kaufman ........................ 283/81
* cited by examiner

*Primary Examiner* — Karl D. Frech
(74) *Attorney, Agent, or Firm* — Quarles & Brady

(57) ABSTRACT

A container label printing method and apparatus, the method comprising the steps of providing a label having first section and a second section spaced apart from the first section and oppositely facing front and back surfaces, providing a container with an external surface, securing the first section of the label to a portion of the external surface of the container with the second section of the label extends from the first surface, providing a printer, using the printer to print indicia on the a the front surface of the second section of the label and securing the second section of the label to the external surface.

40 Claims, 33 Drawing Sheets

| | |
|---|---|
| 500 | Memory Contents -- Information Device 10 |
| 504 | Information Device Data Elements |
| 505 | Serial Number of Information Device |
| 506 | End of Life for Battery |
| 507 | Communication Encryption Codes |
| 508 | Number of Compartments |
| | Information Received from Dispensing System 200, 280 for Compartment $i$ |
| 520 | Selected Patient Information |
| 540 | Selected Prescribed Medication Dose Information |
| 560 | Predetermined Healthcare Worker Information |
| 580 | Dispensed Medication Information |
| 600 | Medication Report Components |
| | Information Received from Patient Identification Device 300 for Compartment $i$ |
| 621 | Specific Patient Information |
| | Information Received from Healthcare Worker Identification Device 320 for Compartment $i$ |
| 681 | Administering Healthcare Worker Information |
| 621 | Specific Patient Information |
| | Information Received from Patient Room Workstation 350 or Computer Peripheral Device 355 for Compartment $i$ |
| 621 | Specific Patient Information |
| | Information Created when Container 100 opened for Compartment $i$ |
| 640 | Consumption Information: |
| 642 | Consumption Tiem Information/Date and time portable container opened |
| 643 | Amount of Medication offered to Patient |
| 644 | Amount of Medication Patient Consumed |
| 660 | Final Transaction Medication Report |

Figure 17

| | |
|---|---|
| 700 | Patient Medication Information -- Dispensing Workstation 200, 280 |
| 520 | Selected Patient Information |
| 521 | Patient Identification Number |
| 522 | Patient Name |
| 523 | Admitting Physician |
| 524 | Patient Room Number |
| 525 | Patient Blood Type |
| | |
| 540 | Selected Prescribed Medication Dose Information for each Medication Prescribed |
| 541 | Medication Type Prescribed |
| 542 | Medication Quantity Prescribed |
| 543 | Dosing Times |
| 544 | Identification of Physician Prescribing Medication |
| | |
| 560 | Predetermined Healthcare Worker Information |
| 561 | Responsibilities/Title Of Healthcare Worker Allowed to Give Medication |
| 562 | Healthcare Worker Identification Number(s) Allowed to Give Medication |
| 563 | Healthcare Worker Name(s) Allowed to Give Medication |
| 564 | List of Patients Under Care of each Healthcare Worker |

Figure 18

| | |
|---|---|
| 580 | Dispensed Medication Information -- Dispensing Workstation 200, 280 |
| 581 | Medication Information |
| 582 | Date and Time Medication Dispensed |
| 583 | Identification of Healthcare Worker who dispensed Medication |
| 584 | Type and Quantity Actually Dispensed |
| 600 | Medication Report Components |
| 720 | Medication Report |
| 724 | Universal Record Locator |

Figure 19

| 620 | Memory Contents -- patient identification device 300 |
|---|---|
| 621 | Specific Patient Information |
| 622 | Patient Identification Number |
| 623 | Patient Name |
| 624 | List of Medications to which Patient is Allergic |
| 625 | Admitting Physician |
| 626 | Patient Blood Type |

Figure 20

| 680 | Memory Contents -- Healthcare Worker Identification Device 320 |
|---|---|
| 681 | Administering Healthcare Worker Information |
| 682 | Responsibilities/Title |
| 683 | Identification Number |
| 684 | Name |
| 685 | List of Patients Under Care of Healthcare Worker |
| 621 | Information Received from patient identification device 300<br>Specific Patient Information |
| 660 | Information Received from Information Device 10<br>Final Medication Transaction Report |

Figure 21

| 690 | Memory Contents -- Patient Room Information Workstation 350 or Computer Peripheral Device 355 |
|---|---|
| 621 | Specific Patient Information |
| 660 | Information Received from Information Device 10<br>Final Medication Transaction Report |

Figure 22

| 660 | Final Medication Transaction Report |
|---|---|
| 520 | Selected Predetermined Patient Information |
| 540 | Selected Prescribed Medication Dose Information |
| 560 | Predetermined Healthcare Worker Information |
| 580 | Dispensed Medication Information |
| 621 | Specific Patient Information |
| 680 | Administering Healthcare Worker Information |
| 640 | Consumption Information: |
| 670 | Medication Report Components |
| 730 | Medication Report |
| 734 | Universal Record Locator |

Figure 23

```
<html>
<body>
<a href="http://hww.st._mary.springfield/demographics/987654321/19_May_1996">
ID: 987654321</a><br>
Date: 13:59 19-May-1996<br>
Report type: Medication Administration<br>
Patient ID Verified: YES<br>
<br>
Medication Given:<br>
Penicillin            100mg        2 capsules<br>
Tylenol w/Codeine    200mg        1 capsules<br>
<br>
Given by: XXXXXX,  at: HH:MM  DD/MM/YYYY<br>
Dispensed by: Sam W. Johnston, R.N., at: 13:42 19-May-1996<br>
<br>
ID Device Serial Number: 1265338<br>
</html>
```
— 720
— 726
— 728

Figure 24 hww.st_mary.springfield/medication/given/987654321/DD-MM-YYYY/HH-MM — 724

```
<html>
<body>
<a href="http://hww.st._mary.springfield/demographics/987654321/19_May_1996">
ID: 987654321</a><br>
Date: 13:59 19-May-1996<br>
Report type: Medication Administration<br>
Patient ID Verified: YES<br>
<br>
Medication Given:<br>
Penicillin                    100mg         2 capsules<br>
Tylenol w/Codeine    200mg        1 capsules<br>
<br>
Given by: Mary T. Adamson, R.N.,  at: 13:59 19-May-1996<br>
Dispensed by: Sam W. Johnston, R.N.,  at: 13:42 19-May-1996<br>
<br>
ID Device Serial Number: 1265338<br>
</html>
```

Figure 26 hww.st_mary.springfield/medication/given/987654321/19_May_1996/13:42

Figure 27

ID: 987654321
Date: 13:59 19-May-1996
Report type: Medication Administration
Patient ID Verified: YES Medication Given:
Penicillin                    100mg         2 capsules
Tylenol w/Codeine    200mg        1 capsules Given by: Mary T. Adamson, R.N.,  at: 13:59 19-May-1996
Dispensed by: Sam W. Johnston, R.N.,  at: 13:42 19-May-1996

ID Device Serial Number: 1265338

Figure 28

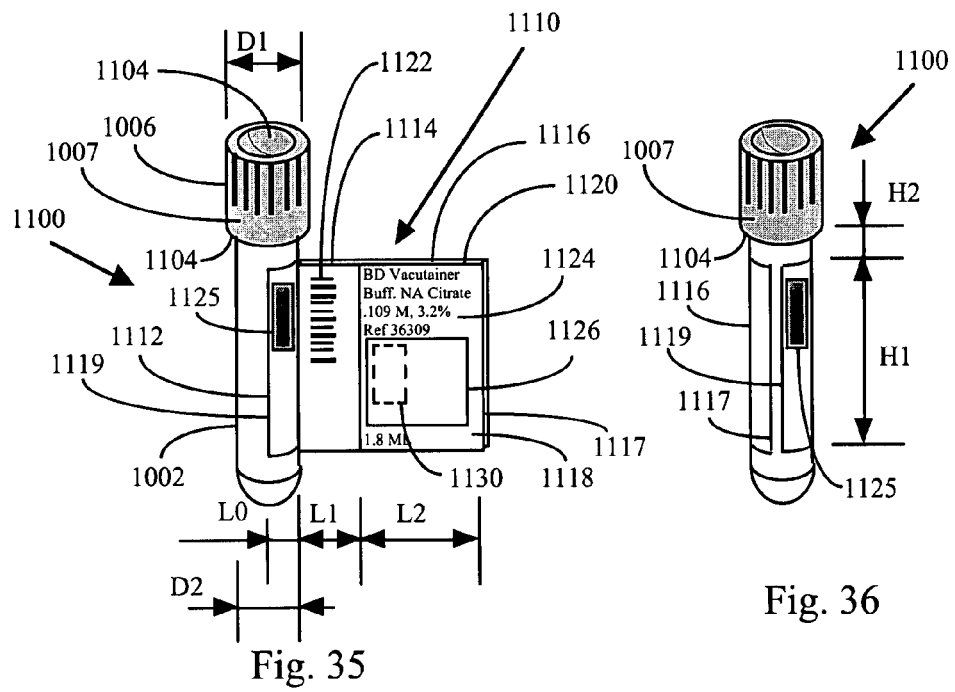
Fig. 35
Fig. 36
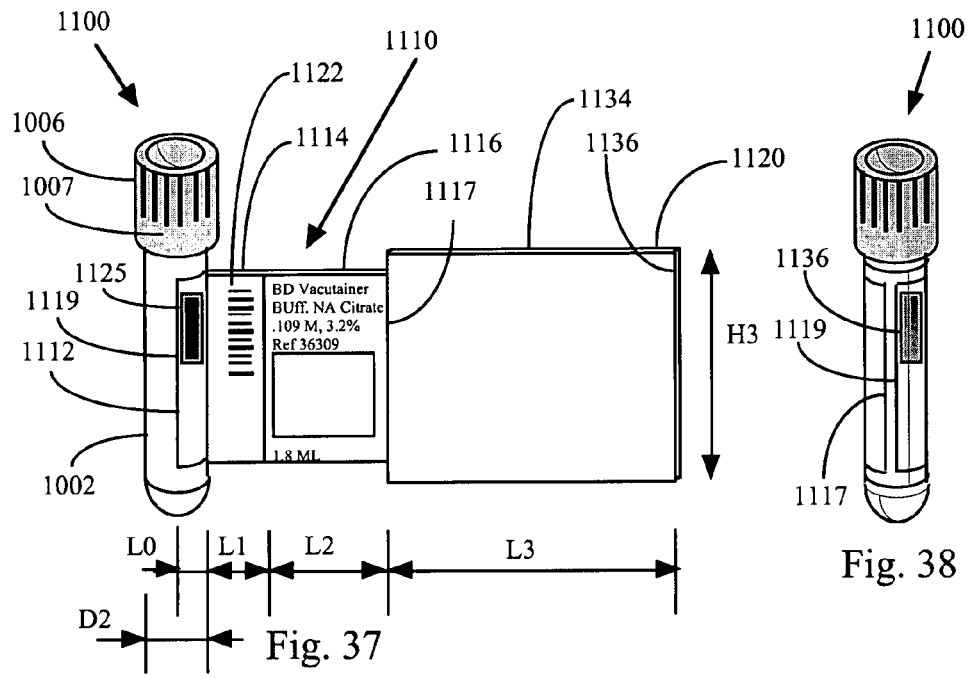
Fig. 37
Fig. 38

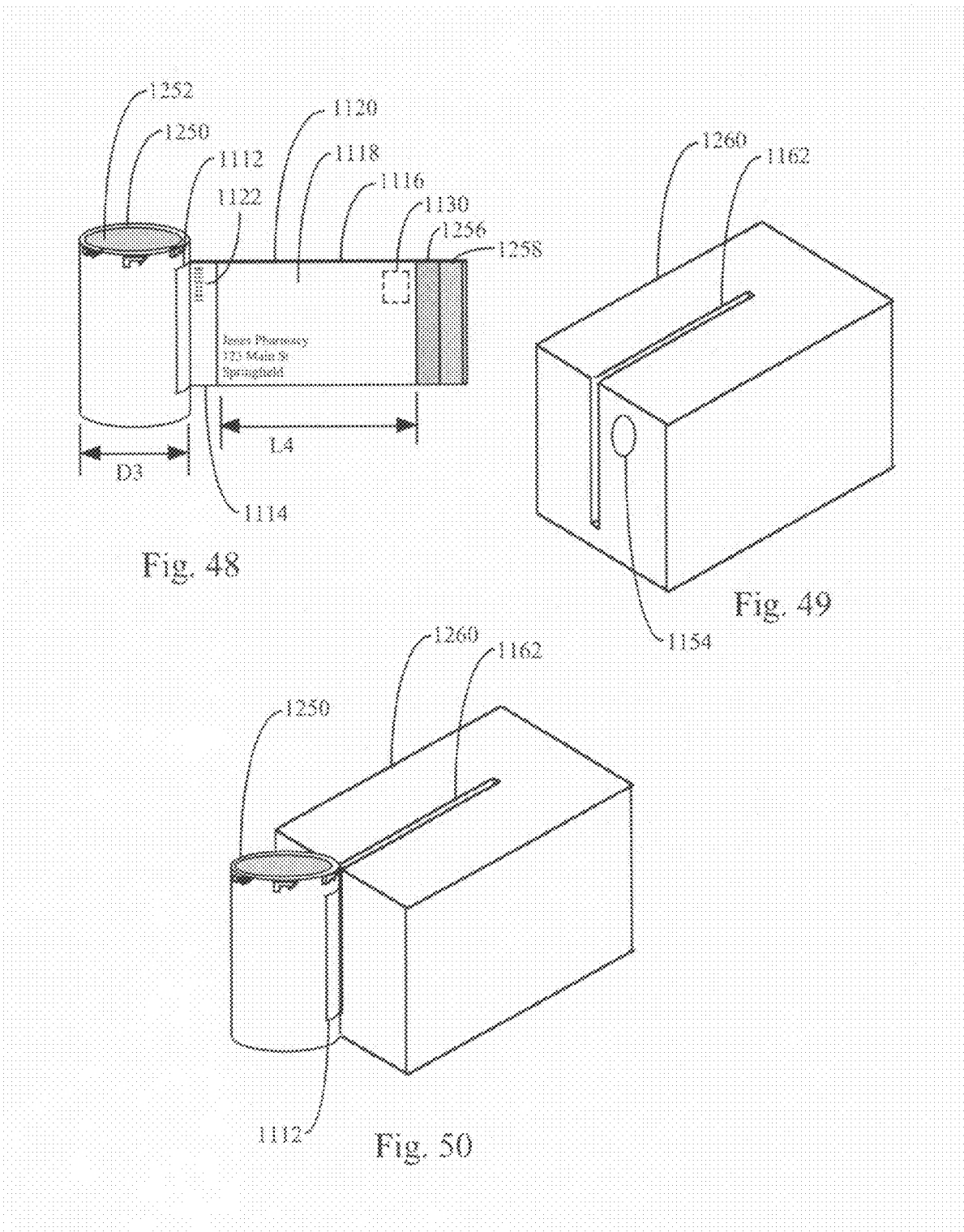

VIAL PRINTING METHOD AND APPARATUS

CROSS-REFERENCES TO RELATED APPLICATIONS

This application is a continuation-in-part of application Ser. No. 09/426,553, filed Oct. 22, 1999 now U.S. Pat. No. 7,216,802 which is titled "Method and Apparatus Verifying Information" which is a continuation-in-part of application Ser. No. 08/955,475 that was filed on Oct. 21, 1997 and that has issued as U.S. Pat. No. 6,032,155.

TECHNICAL FIELD OF THE INVENTION

This invention relates generally to a method and apparatus for verifying different pieces of information, determining if an object can be used to follow the instructions of a work order, and associating information with a physical object. More particularly, this invention relates to a method and apparatus for collecting medical samples according to a work order, verifying that the sample is collected from a specific patient into a specific type of container, automatically recording the time the sample is collected and identifying the health care worker collecting the sample. The sample container is associated with the work order by printing a portion of the work order in a label attached to the container or by linking a sample container serial number with work order information in a hospital database.

BACKGROUND OF THE INVENTION

Millions of medical specimens are collected in hospitals and clinics every day. Each specimen has to be labeled identifying the patient from whom the specimen was collected to ensure that laboratory results associated with the specimen are returned to a correct patient's file or database. It is generally desirable to include the date and time a specimen was collected, the physician order that caused the specimen to be collected and related tests that are to be performed on the specimen, and the healthcare worker who collected the specimen. In the past a paper label was prepared by hand writing the appropriate information on the front surface and then adhering the label to a medical specimen container. However, this technique is prone to error, misreading by others, and is generally unsuitable for automated laboratory equipment to recognize.

One common medical specimen is a blood sample that is normally collected in a vacuum tube. These tubes are often labeled with a manufacturer label and then with a pre-printed secondary adhesive labels that have been prepared for a specific patient. In some cases a sheet of labels is printed and used as needed when samples are collected for the patient. Where sheets of labels are employed, unfortunately, the sheet labels lack information about the healthcare worker who collects the blood sample and the date and time at which a sample is collected. The collection of blood samples is further complicated in that different blood tests require the blood to be collected into tubes with specific reagents (for example anti-clotting or clot activation chemicals) to preserve or start a reaction with the blood and when multiple tubes are to be collected the sequence of collection is important to prevent the reagent in certain tubes from contaminating samples collected in other tubes.

Another concern about the use of hand applied labels is that they can be put on crooked, upside down, or sideways making it much more difficult for laboratory systems to properly read identifying bar codes or other machine readable information printed on the labels. In some cases sample tubes are extremely small such that, when a label is misapplied, a portion of the label may wrap around the tube completely and obscure printed material on a different portion of the label.

Recently the Becton Dickinson Company has made some improvements in the collection of blood samples. In one case blood tubes have been introduced with color coded caps that have matched color coded labels with printed indicia along the top edge. Secondary labels are printed to identify the blood tube and typically include information identifying the patient from whom the blood sample is collected, the collection order number, and other useful information. The secondary labels can include a notch or second indicia along the top edge. A worker aligns the second indicia to the pre-adhered manufacturer label indicia on the tube. Once aligned the secondary label can be wrapped around and adhered to the blood tube in what is a fairly precise orientation.

One desirable secondary label size and alignment criteria is that a portion of the original tube label remain exposed after the secondary label is applied. For instance, in most cases it is desirable that at least a portion of the color coded section of the manufacturer label be exposed after the secondary label is applied so that the tube type can be identified after application and after the cap is removed. Similarly, in most cases it is desirable for at least a portion of the transparent portion of the tube be exposed after the secondary label is applied so that a tube user can observe the condition of the reagent and other material (e.g., a specimen) within the tube after label application. Blood collection tubes are typically 13 mm in diameter and 75 mm in height, allowing for a secondary identification label that is less than 40 mm wide (typically 33 mm wide) and 55 mm high so that when the narrow part of the label is wrapped around the tube (with a diameter of 40.8 mm) a portion of the transparent tube remains unobstructed for viewing.

Another, improvement that has been developed includes a printer that can print blood sample secondary labels at the bedside of a patient. In known embodiments a printer can add the time and can read a bar code corresponding to a patient (e.g., from a wrist band or the like) to the get the patient identification number and even a healthcare worker identification bar code to get a healthcare worker identity number, all of which can be printed using the printer.

Unfortunately, even in the case of bedside printers and color coded specimen tubes, there is still the opportunity for a secondary label to be attached in a misaligned fashion to a tube, for a label to be attached to the wrong type of tube or for a secondary label for a first patient to be inadvertently attached to a tube that includes a specimen from a second patient. Here, where a labeling error occurs, a laboratory processing a blood sample (or other specimen type) may associate the results with the wrong patient in a medical record.

Blood tubes are not the only container that needs to be carefully labeled. There are a variety of body fluid and other samples that are collected and need to be carefully labeled to ensure that a laboratory can associate the samples correctly with patients.

There are also a variety of other containers in healthcare that need to be carefully labeled, for example medication containers or vials. As in the case of specimen tubes, medication vials are often relatively small relative to the amount of human readable text and bar codes that are to printed on them.

The proper labeling and using of non-medical containers and objects is also of great importance.

There are many instances where individuals wish to transport items between locations and track the whereabouts of the items, who is entitled to have access to the items, and other pertinent information. For example, medication prescribed by a physician in a hospital for a patient can be dispensed either manually by a pharmacist or by a unit dose dispensing system in the pharmacy or placed at various locations in the hospital for nurses to use. In the case of manual dispensing, a medication order is sent to the pharmacy where the correct medication is selected or formulated. The medication is then placed in a container, plastic bag, or envelope which is in turn labeled with identification information specifying the patient that is to receive the medication as well as information about the medication dispensed. Such labeling can be achieved by the use of a marking pen or a computer printer adhesive label.

A variety of devices have been invented and several placed in commercial production for the dispensing of unit dosages of medication. These systems are often designed to be placed in a variety of locations in a hospital for local and convenient dispensing of medications. A key advantage of these systems is a reduction in time and labor in the delivery of prescribed medication to a patient. Without such systems, each prescribed medication must be dispensed by the central hospital pharmacy, labeled, and transported to the nurses station near the patient's room. This process must be done 24 hours a day and the dispensing must be done in anticipation of when each new dosage is due with an allowance for time spent in transmit. Unit dosage dispensing systems usually have a tray or cartridge that is loaded with multiple dosages of medication by the central pharmacy. This tray or cartridge is then carried to the unit dosage dispensing system where it is inserted, along with information regarding the medication in the tray or cartridge. This information usually includes the medication name and the number of doses contained. When a patient is to receive medication the nurse usually must use a mechanical key, an electronic key, or a computer password to gain access to the dispensing process. The nurse will identify the medication and may identify the patient to receive the medication. The dispensing system then locates the correct tray or cartridge containing the desired medication and then removes one or more doses of the medication as required, typically delivering them to a drawer or door that the nurse may open to remove the medication.

After dispensing the nurse carries the medication to the patient for consumption. The dispensing system can keep track of the date and time when the medication was dispensed, for which patient it was for, and possibly the nurse to whom it was dispensed. However, the dispensing system cannot determine if the medication was in fact given, if it was given later, who gave it to the patient, or if it was given to the correct patient.

Several studies have documented that most medications in a hospital are given to the correct patient. However, the small percentage of medications that are given to the wrong patient is cause for great concern. This can happen if a patient is moved from one room to another and a new patient is now in the former patient's bed. Occasionally, the former patient's name may be left written on a board near the bed or by the doorway. While nurses are suppose to verify the patient's name or identification number written on a bracelet each time they administer a medication, this may not always happen. The nurse may receive a call to go to an emergency while giving a medication and thus be rushed, the patient may be unable to speak to identify themselves, or the nurse may not want to disturb a patient who is sleeping. Errors in giving medication to the wrong patient can cause a variety of reactions that can sometimes lead to death.

To track when a patient was given medication and who gave it, hospitals employ either manual or computerized recording systems. Manual systems are time consuming and can cause errors in patient billing. Even with computerized record systems, the nurse must spend some amount of time entering and verifying the information. It is claimed that within a hospital that over 60% of all expenses are related to nursing, and of that nearly half of this is for nurses to fill out paperwork and write observations. With continuing efforts to control the rising cost of providing health care, hospitals need to explore all methods possible to reduce nurse time spent away from directly caring for patients.

Problems such as these can occur in other situations, both in hospital settings and elsewhere. For example, hospital personnel may want to store the personal belongings of a particular patient while the patient is receiving treatment and need to identify the belongings so that they are returned to the appropriate patient. Similarly, when medical personnel desire to dispense fluid medication, either in the form of an intravenous solution or medication to be taken orally, they must keep track of how much and what type of fluid is being dispensed and which patients have received their medication. In each of these cases, it can be very time consuming to write down the type and quantity of substances being identified, who is accessing the substances, what time the transaction is taking place and other important information in order to ensure that the task is being performed correctly.

Problems such as these can go far beyond the medical field. In the manufacturing industry, for instance, it is often important to keep adequate records of individual components. For example, if a particular prototype device or key part is being transported from one place to another, and only a few qualified individuals are supposed to have access to the component, or the component is only to be delivered to a particular location or process, it is important to have a system for ensuring that only the proper individuals are allowed to access the component. It may also be important to record the time at which the component is delivered to its destination, where it is currently located, and similar pertinent information.

Although these problems may appear to be particular to certain industries, the common theme between them all is that there is a need for tracking and permitting access to certain objects, recording relevant information, and doing so with minimum expense, time, and effort.

The present invention is intended to solve these and other problems.

SUMMARY OF THE INVENTION

The present invention includes containers with manufacturer applied labels that can be printed or written to. In one embodiment a label is partially pre-attached to a container and compatible information devices or printers print text or machine readable codes, such as bar codes, to the free end of the label. The printer in some cases can also read and/or write to memory tags, such as radio frequency identification tags or other memory devices attached to or that form part of the label. Combined, the labeled containers and compatible printers, can create a system to reduce medical errors by ensuring information about a specific medical sample collection is either printed, written, or programmed to the label of the container in which the sample will be or has been collected.

In some cases a serial number that is preprinted on (for example as a bar code) or written to (for example a memory tag) a label is read. Information about the sample collected (blood collection work order number, patient identification, healthcare worker identification, and date/time) is transferred to a database (e.g., via wireless communication such as one of the 802.11 standards) along with the container serial number.

A laboratory system that later reads the serial number code or tag can use it to retrieve from the database the remaining information about the sample collected.

In either case a work order (for example an order written by a physician to collect a specific sample, for example blood, from a specific patient on a specific day) is obtained by the printer. The printer receives the work order by reading a work order bar code printed on a work order sheet of paper or it is obtained by the printer receiving the work order by wireless communication (for example using an 802.11 standard) in response to sending a patient identification number to a database or by having the data base send the work order to a printer associated with a location in a hospital.

After collecting a blood sample, the specific container used to collect the sample is associated with a portion of the work order. The association can be in the form of printing text, bar codes, or memory tags that identify the work order, patient, time and/or healthcare worker who is following the work order on a label that is adhered to the container or a label that will be attached to the container used to collect the sample. Any one who can read the label or the machine code or memory tag will understand that the container contains a sample from the patient and that it is to be analyzed according to the work order. As stated above the association can be in the form of a link, between a container serial number used to collect the sample and the work order in a database. By reading the serial number (as text, a machine code or memory tag) the remaining information for the work order can be obtained from the database.

When the container is a blood tube the partially pre-attached label can be color coded to match the cap color that is used to indicate the type of reagent in the tube. The label can be made of tear-resistant synthetic or other durable paper. The label may have three sections including, first, an adhered section which may be color coded or have manufacturer printed information, such as a tube type designation or serial number bar code. The adhered section may be as narrow as 2 mm wide and will be attached to the vertical wall of the blood tube/container. Second, the label may include a spacer section which can also be color coded and have manufacturer information printed on it. This spacer section is the section that, while inserted into the printer, cannot be printed as most printer mechanisms require some distance between a print head and a wall of the container, similar to the margin in conventional printers. Third, the label will include a section that is printed to by the printer, and, when the label includes a memory tag, that can be read and/or written to.

At least a portion or the entire rear surface of the unattached label sections can be coated with an adhesive with a removable release liner. After printing blood collection information to the label, the release liner can be removed and the label wrapped around blood tube, adhering it to the vertical wall of the tube and, when desired, leaving a portion of transparent tube unobstructed. For example, if a tube is 13 mm in diameter, the total length of the label with all sections might be 38 mm. This will leave a gap of 2 mm so that the blood sample can be viewed at every height along the tube.

When the label is partially pre-attached to the tube, when the healthcare worker wraps the label around the tube, the label will be precisely aligned, both vertically and laterally, with the tube at an optimal location.

Before the label can be printed, a variety of information is typically collected either by the printer or by a data collector. For instance, a hand held bar code reader or a personal digital assistant equipped with a bar code reader may be used to transfer collected information to the printer. The printer or data collector can read a bar code number corresponding to a work order number on a work order sheet, a patient identification number bar code from a patient wristband, a healthcare worker identifier from a bar code on a badge, and a bar code identifier from a blood tube/container. The work order number can also be obtained by reading the patient's identification number and communicating this number to a database (e.g., wirelessly via the 802.11 or other standards) to obtain the current blood collection order information. The date and time of collection can be provided by the printer or the data collector. In some cases the printer or data collector will send some of the collected information to a database by wireless communication that can be linked to the patient's identification number, the work order number, or a blood tube serial number. While some embodiments are contemplated wherein no information needs to be printed onto a label, in most cases it is anticipated that at least some of the collected information will be printed on the print section of the front surface of the label or written to a memory tag that is part of the label.

It is also anticipated that the printer or data collector or the database will compare the patient identification number read from a wristband and the patient identification number associated with the work order number to ensure blood is being collected from the correct patient (i.e., the patient associated with an order). If the identity of a patient does not match the patient associated with an order, an alert is presented to the healthcare worker that the worker has the wrong patient.

Similarly, the printer or data collector or the database will compare a bar code number on a blood container that identifies the blood container type to the blood containers or blood tests ordered in a blood collection work order to be sure that the correct container types have been selected by the healthcare worker for obtaining blood from a patient associated with the order. Furthermore, the order in which the blood tube types are presented can be compared to a standard procedure for blood collection, to make sure that the blood tubes are used in the correct sequence. Thus, for instance, in cases where blood tests A, B and C are always to be performed in the sequence A, B and C (e.g., a sequence of B, C and A would be wrong), the present system may help a healthcare worker sequence tubes in the proper order A, B and C.

As a further safety measure, the time between starting to collect various information and the printing of a label can be limited to a time period, for example 3 minutes plus some extra time (for example 30 seconds) for each blood tube over one used. By imposing a time limit, the system can prevent a healthcare worker from reading a first patient's wristband, being called away to a second patient and printing labels for the second patient using the first patient's identification number for labeling a container label.

The extended label is designed to be placed in the printer to print textual information and/or a bar code when desired (e.g., the order number or the patient identification number) on the front surface of the label and when the label is so equipped to write information to a memory tag. The printer is designed so that the unattached sections of the label are inserted in the printer mechanism. The spacer section cannot be printed, while the print section can be printed on in any conventional manner, for example inkjet printing, laser printing, direct laser printing without toner (similar to LightScribe® printing developed by the HP Company), thermal printing, or thermal transfer printing.

After printing, the label is removed from the printer and the release liner is removed exposing the adhesive on the rear surface of the label. The label is then wrapped around and adhered to the blood tube. The worker can be advised that the tube needs to be inverted or rotated a specific number of times to ensure proper mixing with the reagent in the container. The number of rotations varies by the reagent used and can be determined by the printer reading the tube type bar code of the blood container. In some cases the printer can rotate the tube for the healthcare worker before, while or after the label is being printed.

To assist with printing the label, the blood tube can be inserted into an opening in the printer and the label inserted in a corresponding slot in the printer. The blood collection tube can rest on the underside ledge formed between the tube and the cap and the top of the printer. This creates a physical reference between the top edge of the label and the upper part of the printer. Other physical characteristics can be used for this purpose, for example the bottom of the tube can rest against a stop in the printer and the top of the label can be registered relative to the bottom of the tube, or a special alignment ring can be provided around a section of the tube to align it and the label with the printer. In this manner tubes of various lengths can be used with the printer and the labels for each of them will be aligned properly in the printer.

Some blood tubes have a larger diameter than others. The opening in the printer where the tube is inserted can be sized to the largest tube diameter and a spring in the printer can push the tube close to the printing section. Alternately a friction roller can pull the label into the printer, aligning the tube in the printer adjacent to the printing section.

A more comprehensive system for selecting blood tubes and printing label can be created by using a smart tray, tote, or cart designed to hold a variety of identified blood tubes. For example a single package holding several blood tubes of a specific type can be inserted into one matching recess in the tray and another package holding several tubes of a different type can be inserted in to another recess. The contents of each tray can be registered with a computer by keyboard or by the tray reading a machine readable code attached to printed on each package. When a patient order is obtained by the processor, the system can identify, using a display and/or individual LED indicators, the packages from which blood tubes are to be selected, how many tubes are to be selected from each package and the sequence in which the tubes are to be selected.

Tubes not in the smart tray but needed to complete an order can be stored in a drawer or other compartment. When needed, the bar code or machine readable code can be read by an external bar code reader that is part of the smart tray or by a handheld reader that communicates with the smart tray to determine that a specific tube corresponds to a specific blood collection order.

The smart tray may also be equipped with a printer to print on a print section of a label information about blood collection and to write to a memory tag when the label is so equipped. The labels and matching printer can be used to print information on a variety of medical containers for specimens collected from a patient as well as printing labels for medication containers given to a patient.

Alternately, the smart tray may be equipped with a label printer to print a secondary label with blood collection information. The label printer can be a color printer and the secondary labels can be printed to include a color code to match the color code of the blood tubes caps and labels. Once printed. the secondary label may be wrapped around and adhered to the blood tube.

The present invention provides a system and method for verifying information and activating a response function when two or more pieces of information correspond to each other. Such a system is comprised of an information device and an identification device. The information device has certain identification information stored therein. Additionally, the information device may be adapted to store and be capable of receiving various other information from various sources.

The identification device has an additional set of identification information stored therein or thereon. The information device is capable of receiving or otherwise obtaining the identification information stored in or on the identification device. The information device compares the identification device and information device identification information. If the two sets of identification information correspond, then the information device activates a response function by providing a response signal.

Alternatively, the information device may act as a relay, communicating the identification information from the identification device and other identification information stored in the information device, such as prescription information, via RF communication or some other conventional method, to a remote or local computer comparison system. At the remote or local computer comparison system, the identification information from the identification device and other information are analyzed to determine if the information corresponds, e.g., the information corresponds if the prescription defined by the prescription information is appropriate for a patient identified by the identification information. A comparison result signal is communicated back to the information device indicating whether or not the two sets of information correspond. The information device may then activate a response function by providing a response signal in response to the comparison result signal received from the remote or local computer comparison system.

The response function may comprise an indicator, a locking mechanism, or both. In the case of an indicator, when the two sets of identification information correspond to each other, the information device activates the indicator. The indicator may provide a visual and/or audible signal, informing the user that the two pieces of identification information correspond to each other, thereby verifying the information.

In the case of a locking mechanism, the locking mechanism may control access to another object, such as a container. When the two sets of identification information correspond to each other, the information device communicates with the locking mechanism to unlock the container. This system can be applied in a modified form in the case where there are two or more compartments located inside the container. In such a case, there may be more than two pieces of identification information that are compared to each other. If the identification information corresponds to only one portion of the information in the information device, then fewer than all of the compartments of the container will be unlocked or locked.

An information device in accordance with the present invention may be adapted to receive updated information, via wireless or non-wireless communications, from a remote location, relating to a required change in the contents of a container to which the information device is attached. For example, a container may hold items identified by an information device in accordance with the present invention attached thereto. Prior to comparing the identification information of the information device with the identification information of an identification device, a change, e.g., in the intended use of the items in the container, may be communicated to the information device. An audible or visual indication or message may be provided by the information device when the changed information is received by the information device, or at the time a comparison of identification information is performed, indicating, e.g., that additional items not in the container need to be obtained or that some or all of the contents of the container are no longer to be used.

The present invention is application in many situations and industries. In particular, and for example, the present invention may be employed in a medical setting wherein a system for placing unit doses of medication into a portable container labeled with textual and electronic information is provided. The electronic information or electronic labeling is recorded on an information device. The information device is used in conjunction with other electronic devices to record when the doses of medication are given to a patient, the patient who received the medication, and the healthcare worker, such as a nurse, who administered the medication. The information device can include a sensor for sensing when the container is opened, a date and time clock for determining the time the medication is administered, and a locking mechanism. The locking mechanism locks the medication in the container until an appropriate time has been reached and the appropriate patient has been identified. The electronic labeling can include information regarding the intended patient, the names and quantities of each medication in the container, the time the medication is intended to be given, the physician who ordered the medication, the healthcare worker who dispenses the medication, and other pertinent information.

The information device may be separate from the portable container, and therefore not in contact with the medication, or it can be in integral part of the portable container. The information device includes a computer processor, a memory element, a power source, and a communication device for transmitting and receiving electronic information to and from other electronic devices. The information device can also include a display, such as an LCD.

The information device may be used in conjunction with an automated dispensing system that automatically dispenses desired medications into the portable container, or an automated dispensing system where a healthcare worker manually dispenses medication into the portable container. When medication is dispensed by an automated dispensing machine, the healthcare worker must properly identify themselves. This can be accomplished by the entry of a password unique to the healthcare worker. The healthcare worker then identifies the patient to whom medication is to be given. This may be by selection from a list of patients to whom the healthcare worker has been assigned. The healthcare worker may not select an inappropriate patient or one not in this area of the hospital. If the patient has been transferred outside of the area where the dispenser is located, the dispensing system can alert the nurse to this fact and can prevent any medication from being dispensed. The correct location of the patient may be determined via an information exchange with other computer systems in the hospital, e.g. Admit, Transfer, Discharge System (ADT) using a computer network, or this data can be maintained within the dispenser itself and updated manually.

Having selected a patient, the healthcare worker is presented with a list of medications that have been prescribed for the patient. Medication that can be given at this time, determined by the prescription regimen and the times of previous doses being consumed by the patient, may be distinctly displayed for selection. After selecting one or more medications and the quantity to give, the system dispenses each medication.

As each medication is dispensed, they are placed in the portable container. When all the desired medications have been dispensed, the container is closed, and a textual label may be written on the container with information to identify the patient, the medication, its quantity, when the medication is to be given, and other data as appropriate. The same information is also written electronically to an information device. After being written, the data is verified and attached to the container. The information device includes the medication information described above. Finally, the information device is attached to or otherwise associated with the portable container and presented to the healthcare worker. The information device can be attached to the container so that it locks the medication in the container until an appropriate clearance is granted, or the device can be constructed so that it only detects the opening of the container and communicates any necessary warning to the healthcare worker.

The medication may also be manually dispensed at a workstation from bulk containers into the portable container. The workstation includes a computer and input terminal to enter data, such as medication information regarding the medication placed in the portable container. The healthcare worker then uses the workstation to transmit or write the medication information to the information device. Alternately, the healthcare worker may use a computer workstation to determine the medications due to be given to the patient. By selecting the medication due to be given, the healthcare worker can cause the workstation to automatically prepare medication information for transfer to the information device.

The medication container may be of a single use variety, in which case only the information device is returned to the dispensing system for reuse. When the information device is returned to the dispensing system or presented to a computer workstation, the information device is read to assist in data recording and examined for any errors or operational problems. When the device is read, a variety of data may be retrieved from the information device besides that previously written to it regarding the medication information. This data may include the date and time the container was opened, information confirming that patient identification verification was used to confirm that the medication was given to the correct patient, and the healthcare worker identification of the person who gave the medication to the patient.

The medication information and other data is transmitted to the dispensing machine or the workstation in a format that can automatically be sent to the correct database for the patients records and formatted appropriately for the database system. An example of this is the creation of a Universal Record Locator (URL) address compatible with a hospital Intranet network. The address may be in a format not normally known to the dispensing system. Thus, the dispensing system can be used in several different hospitals without having to be significantly modified to accommodate differing address schemes. A medication report can also be formatted in a manner compatible with the Hypertext Markup Language (HTML), which will help preserve the independence of the dispensing system from the specific software requirements of the nurse reporting and charting system, which may vary from hospital to hospital.

In the case of any errors or operational problems being detected (e.g., inability to read the information stored in the information device, or battery beyond its expected service life), the device will be removed from service and stored in an area for retrieval by a service technician. A failure or service request message can be presented to the healthcare worker or sent by computer network to the pharmacy or hospital engineering department.

The information device will be compatible with a patient identification verification system. Such a system can transmit some or all of the patient identification information to the information device. This may be done by a communication between a patient information device, with a compatible communication device, attached to or associated with the patient and the information device. It may also be done by communication from a patient information device to a computer processor associated with a healthcare worker with a compatible communication device. The patient identification information is then communicated to the information device. The healthcare worker computer processor may be a workstation the worker has logged into, a portable computer device (e.g., personal digital assistant—PDA), or a healthcare worker information device such as an electronic badge that is worn. The healthcare worker computer processor is in some manner known to be temporarily or permanently associated with the patient, for example, by having recently read the patient information device. In this case, the medication information held in the information device can be transmitted to the healthcare worker computer processor and in turn can later be transferred to the dispenser or a computer workstation for prompt and automatic data recording or for transmission to database computer system as described above.

The information device may also be adapted to receive updated medication orders. For example, the information device may receive communications from, e.g., the hospital computer system indicating that there has been a change in the medication order contained in the container to which the information device is attached (e.g., medication is cancelled and/or added to a prescription). This information relating to a required change in the contents of the container to which the information device is attached may be presented to a user as a display or alarm, which may be presented by the information device when the container is opened or an identification verification is attempted.

A portable information device in accordance with the present invention may also be employed as part of an infusion pump control system. Infusion pump control information (e.g., prescribed flow rates and durations) may be stored in the information device. The information device may then be attached to the appropriate IV bag, which is conveyed to the infusion pump. At the infusion pump, the control information is communicated to the infusion pump controller from the information device. This system may be employed in combination with a patient verification system to ensure that the correct patient is provided with the correct IV prescription.

At least some embodiments include a container label printing method comprising the steps of providing a label having first section and a second section spaced apart from the first section and oppositely facing front and back surfaces, providing a container with an external surface, securing the first section of the label to a portion of the external surface of the container with the second section of the label extends from the first surface, providing a printer, using the printer to print indicia on the a the front surface of the second section of the label and securing the second section of the label to the external surface.

Other embodiments include a container/label assembly for use in filling work orders that specify container types to be used to fill each order, the assembly comprising a container with an external surface, a label having a first section and a second section spaced apart from the first section and oppositely facing front and back surfaces, the first section secured to the external surface of the container with the second section of the label extends from the first surface and a container type identifier physically associated with the container, the type identifier including at least one of text, a machine readable code and a color indicia indicating the type of the container, wherein the container type is useable to verify that the container can be used to complete a work order.

Still other embodiments include a method to properly complete a medical work order providing a medical work order that specifies a type of container to be used to facilitate the order, providing a container of a specific type where the container is at least substantially empty and the container includes a container type identifier identifying the container type and the container has an external surface, securing a first section of a label to the exterior surface where the label has a second section that extends from the first surface and filling the container according to the container type identifier.

Some embodiments include an apparatus for storing containers and for use with a database that stores at least a first work order that specifies a first container type to be used to facilitate the first work order, the apparatus comprising carrier with at least first and second recesses, the first recess holding at least one of the first container type and the second recess holding at least one of a second container type, a memory storing information that specifies the type of container in each of the recesses, an output device and a processor that is linked to the memory and the output device, the processor programmed to obtain the first work order from the database, identify the first container type specified by the work order and generate an output via the output device that indicates the first container type specified by the first work order.

Other aspects and advantages of the invention will become apparent upon making reference to the specification, claims and drawings.

BRIEF DESCRIPTION OF THE DRAWINGS

FIG. 17 is a listing of the memory contents of the information device.

FIG. 18 is a listing of patient medication information.

FIG. 19 is a listing of dispensed medication information.

FIG. 20 is a listing of the memory contents of the patient information device.

FIG. 21 is a listing of the memory contents of the healthcare worker identification device.

FIG. 22 is a listing of the memory contents of a patient room workstation or computer peripheral device.

FIG. 23 is a listing of final medication transaction report.

FIG. 24 is a medication report for transmission in an HTML format.

FIG. 25 is a universal resource locator data storage address.

FIG. 26 is a medication report for transmission in an HTML format.

FIG. 27 is a universal resource locator data storage address.

FIG. 28 is a medication report as displayed on a computer monitor.

FIG. 35 shows a container with a label for printing that is partially attached to the container;

FIG. 36 shows the container of FIG. 35 now with a label wrapped and adhered to the container;

FIG. 37 shows a container with a label for printing and a protective overcoat partially attached to the container;

FIG. 38 shows the container of FIG. 37 with the label wrapped around the container and the overcoat further wrapped around the container to protect the printed part of the label;

FIG. 48 shows a medication container with a partially attached label;

FIG. 49 shows a medication container printer;

FIG. 50 shows the partially attached label of a medication container being printed;

DESCRIPTION OF THE PREFERRED EMBODIMENTS

Figure 14:
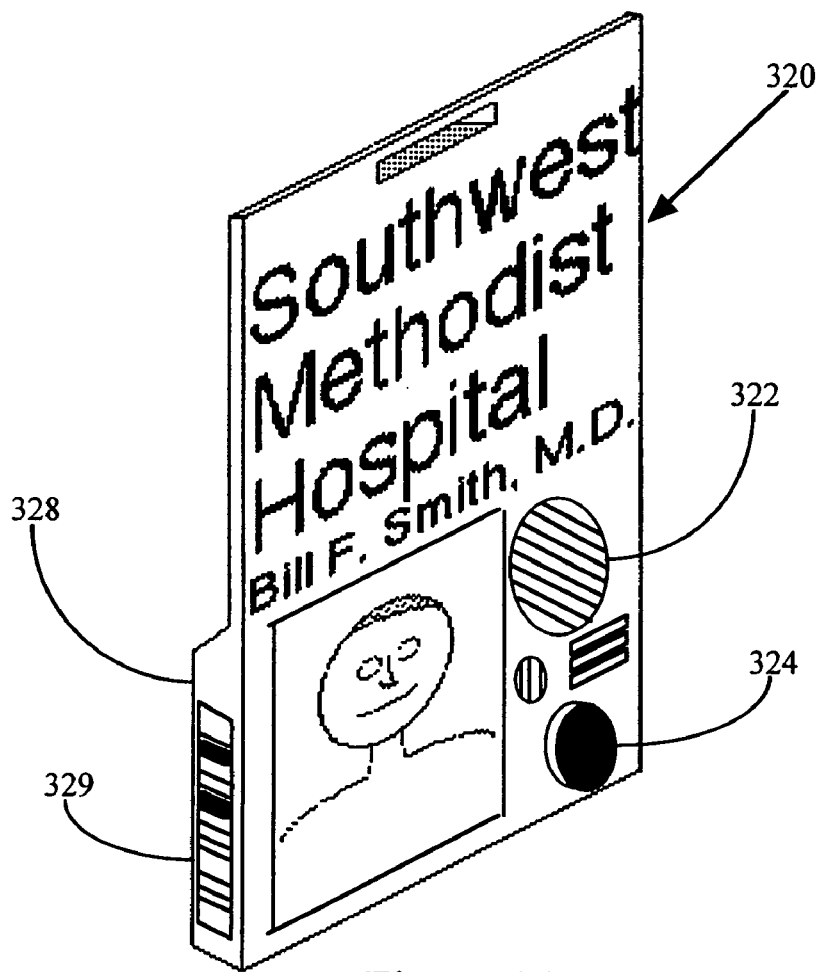
FIG. 14 is a perspective view of a healthcare worker identification device.

A verification apparatus in accordance with the present invention comprises an information device 10 and an identification device 300, 320. The identification device 300, 320 includes identification device identification information 621, 681. The types of identification device identification information 621, 681 that can be included in the identification device 300, 320 are almost limitless. In a preferred embodiment of the invention, identification device identification information 621, 681 may include the name of an individual worker, the worker's position, job description, qualifications, certification, and duties, and what tasks the worker is authorized to perform. The identification device 320 can be as small as a credit card or an ID badge, as shown in FIG. 14. Identification device identification information 621, 681 can be stored in memory in the identification device or on the identification device 300, 320 via either a bar code, a magnetic strip, or other similar means.

The information device 10 is preferably portable and is also capable of having identification information stored therein. Information device identification information (exemplified as selected patient identification information 520) can also cover a variety of matters. The information device 10 can include information about the contents of an attached container 100, the day's date and time, the location of the information device 10, and individuals who are entitled to have access to the contents of the attached container 100. The information device 10 also includes means for reading or otherwise obtaining the identification device identification information 621, 681. In an embodiment where the identification device identification information 621, 681 is stored as a bar code 319, 329, the means for reading this information is comprised of a scanner. When the identification device identification information 621, 681 is stored on a magnetic strip, the means for reading this information can be in the form of a magnetic strip reader.

Figure 10:
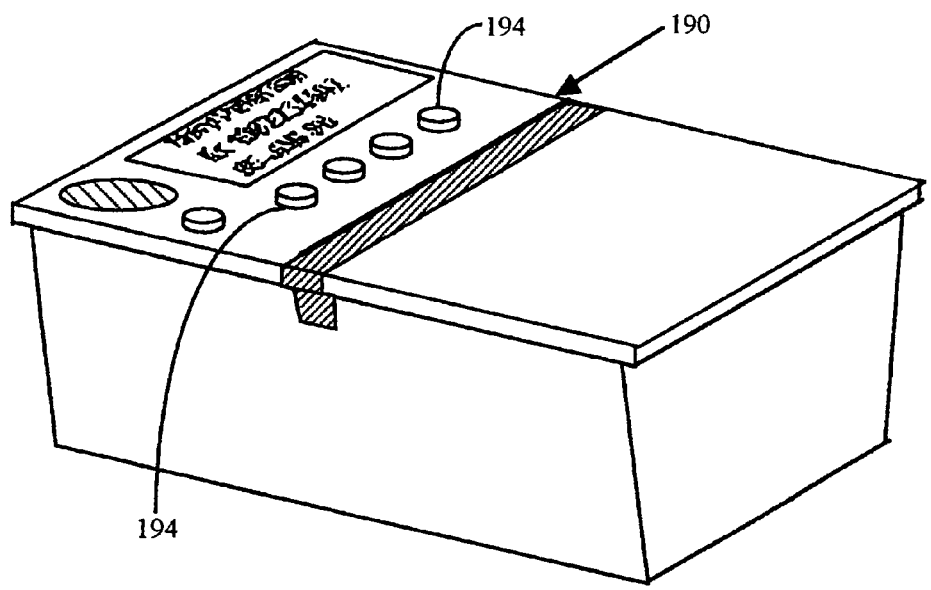
FIG. 10 is a perspective view of an integral portable container and information device with the information device built into its cover.

In a preferred embodiment of the invention, the verification apparatus also comprises a container 100. The present invention may be employed in combination with any type of container. (Container 100 as illustrated is only exemplary of the types of containers which may be employed. Container 190, shown in FIG. 10, is another example.) This container 100 may store items of various sizes ranging from individual pieces of medication to large personal belongings, items or parts of manufacture, etc. Although the container 100 is preferably portable, it can be integrally connected to the information device and can also remain in a fixed position depending upon the intended use. In a more preferred embodiment of the invention, the container 100 includes a latching mechanism for opening and closing a door of the container 100. The container 100 may also include a sensor 86 for providing an indication when the container is opened or is attempted to be opened.

The operation of a verification apparatus in accordance with the present invention is as follows: the identification device 300, 320 is presented to the information device 10. The information device 10 then obtains the identification device identification information 621, 681 from the identification device 300, 320. The information device 10 then proceeds to compare the identification device identification information to the information device identification information 520 stored therein. In the event that the identification device identification information 621, 681 and the information device identification information 520 correspond to each other, then the information device 10 activates a response function by providing a response signal.

Alternatively, the information device 10 may relay the identification information obtained from the identification device 300, 320, along with other information device identification information, such as prescribed medication information 580, to a remote or local (attached) computer comparison system. This communication may be performed in a conventional manner using RF communication, employing an RF transmitter/receiver in the information device 10, or by any other conventional wired or wireless communication method. A determination is made if the identification device identification information corresponds with the information device information by the remote or local computer comparison system. For example, where the communicated information device information is prescription information 580 and the identification information is patient identification information obtained from a patient identification device 300, a determination may be made by the comparison system whether or not the prescription information and identification information correspond. Correspondence may be found by the comparison system if the prescription is appropriate for the identified individual. (In this case, the comparison system may be part of a medication dispensing system.) The computer comparison system may provide an identification information comparison result signal back to the information device 10, over the same or a different communication channel, indicating the result of the determination. The information device 10, in turn, may activate a response function by providing the response signal in response to the received comparison result signal.

In a preferred embodiment of the invention, the response function is in the form of unlocking a latching mechanism on the container 100. This action allows the user to access the contents of the container 100. In an alternate embodiment of the invention, the response function is in the form of either an audible or visual indicator. For example, when the two pieces of information correspond to each other, then the indicator could produce an audible noise informing the user that the identification device identification information has been accepted. The information device 10 may also activate a response function when the two pieces of information do not correspond to each other, or if the two pieces of information do not correspond to each other and a sensor indicates that the container 100 to which the information device is attached was opened or was attempted to be opened nevertheless. In such a case, the response function could be in the form of audio or visual alert signal. Also, the opening of, or attempt to open, the container 100 when the two pieces of identification information do not match may be noted in memory 62 of the information device for later examination or communication to a remote computer system. Whenever an indicator is used, it may indicate that the information does or does not correspond. The response function is preferably integrally connected to the information device 10.

The verification apparatus may also include several peripheral items. For example, the information device 10 may include data entry means such as a computer keyboard for modifying or inputting new information device identification information (e.g., selected patient information 520) to be stored in the information device 10. The verification apparatus may also include output means such as an LCD display 34. This display 34 may be used for either sending alert messages to the user or for displaying pertinent information device identification information or identification device identification information. Additionally, the verification apparatus may include a printer or other means for transcribing information located on either the information device or the identification device.

Figure 32:
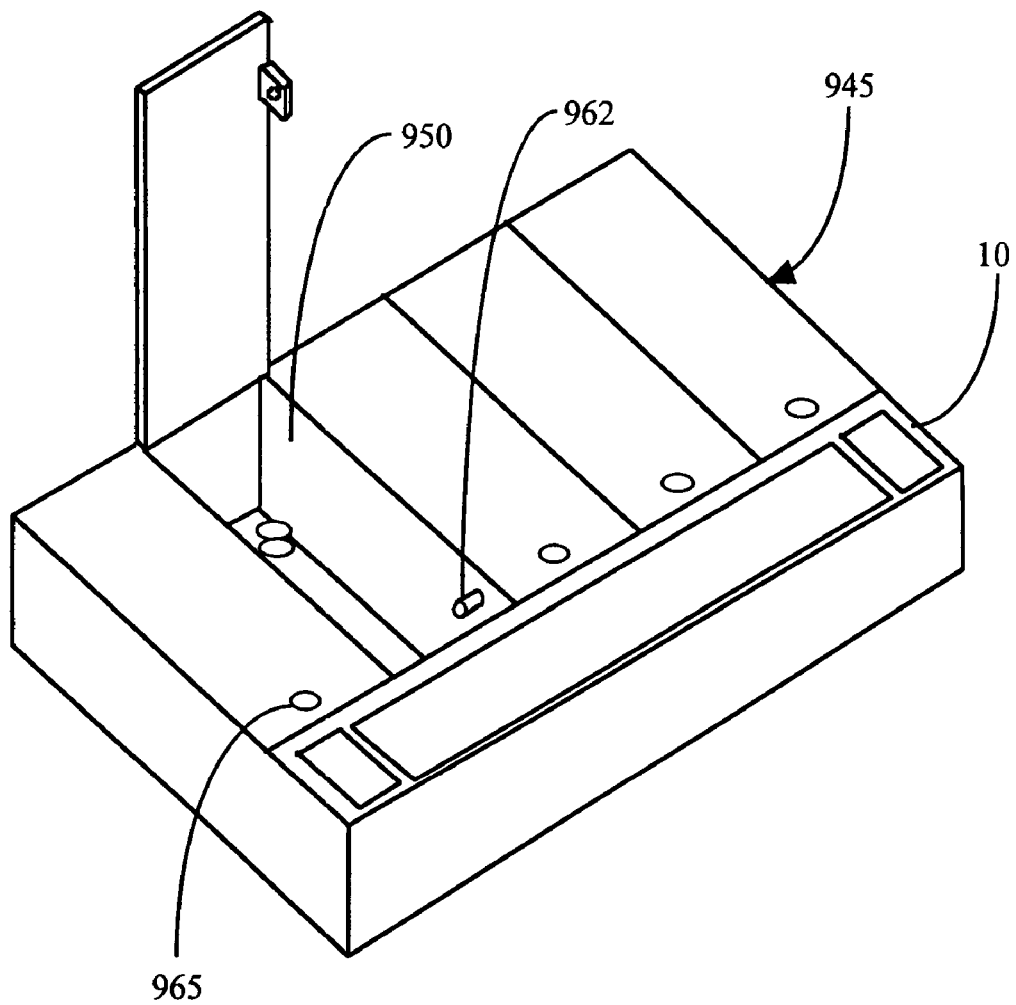
FIG. 32 shows a container with multiple compartments according to one embodiment of the invention.

In an alternate embodiment of the invention, a container 945 may be modified to include multiple compartments 950. As shown in FIG. 32, each compartment 950 includes separate latching mechanisms 962 for opening and closing individual compartments 950. The information device 10, which may be integrally formed with the container 945, may include information device identification information (e.g., selected patient information 520) for each compartment 950 of the container 100. (See FIG. 17.) When identification device identification information 621, 681 is presented to the information device 10, only those compartments 950 for which the information device identification information 520 corresponds to the identification device identification information 621, 681 would be capable of being opened. Additionally, or alternatively, an indicator, such as an LED 965 or an audible tone, may be provided when there is correspondence of selected identification information for selected compartments 950 of the container 945. This could be very important in a hospital setting where the same verification apparatus could be utilized to control prescription drugs for several different patients held in the same container. By having multiple compartments 950 with their own associated information device identification information 520, one apparatus could be used while still ensuring that the wrong medication is not given to the wrong person. Individual compartments 950 may also only be opened, and/or an indication provided, when an appropriate time for opening the compartment (e.g., to dispense medicine) is reached. Thus, different medications may be provided to a patient at appropriate times during a day.

While this invention is susceptible of embodiment in many different forms, the drawings show and the following specification describes in detail, and for example, a preferred embodiment of the invention. It should be understood that the drawings and specification are to be considered an exemplification of the principles of the invention. They are not intended to limit the broad aspects of the invention to the embodiment illustrated. In particular, although the present invention is described in detail with reference to the exemplary application of dispensing medication in a hospital setting, the present invention is applicable in many other situations and settings, including commercial and industrial applications. Thus, it should be understood that, throughout the following description, reference to a "patient" can be considered an exemplary reference to a larger class of generic "objects" to be identified, "medication" can be considered an exemplary reference to generic "materials" or "goods" to be contained in a container, a "healthcare worker" is an exemplary reference to a generic worker or other authorized person, and a medication "prescription" is an exemplary reference to a generic type of process order.

Information Device and Portable Container

Figure 1:
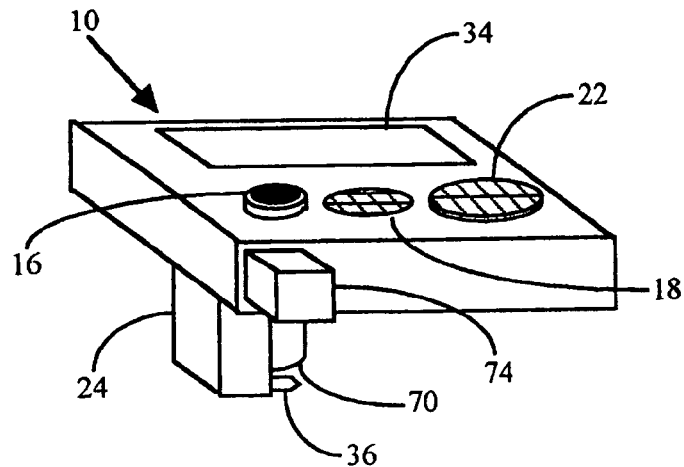
FIG. 1 is a perspective view of an information device having a latch for locking a portable container into a closed position.
Figure 2:
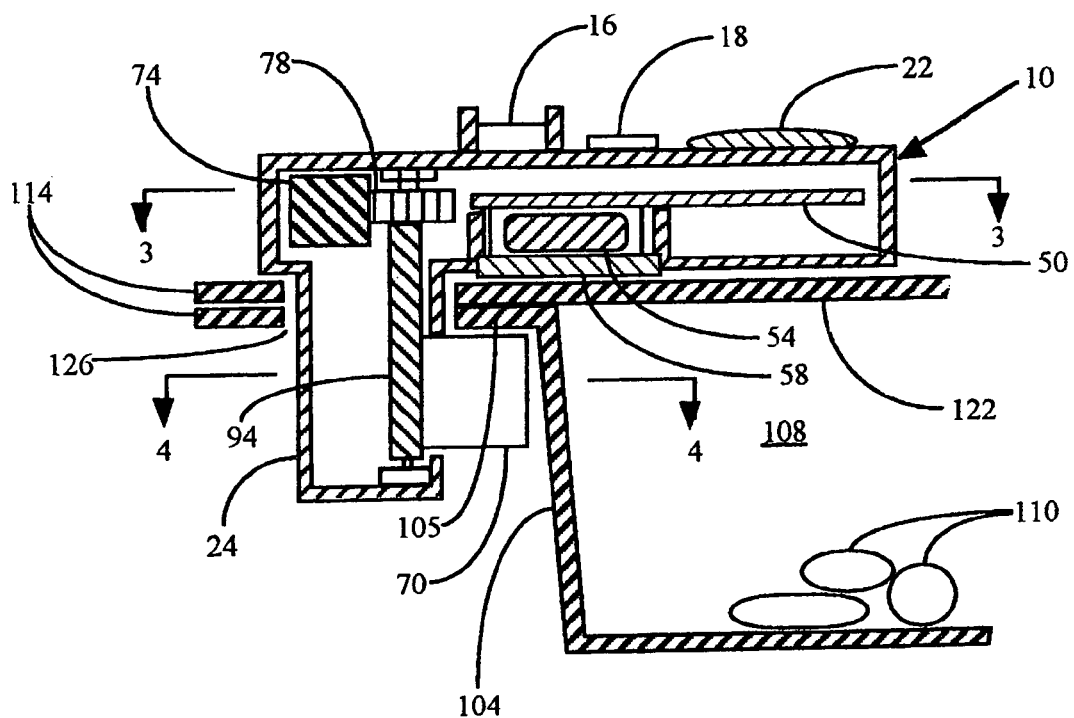
FIG. 2 is a sectional view of the information device attached to the container, with the latch of the information device locking the container into its closed position.

An information device 10 is shown in FIGS. 1-4. The information device 10 includes activation button 16, audible alert device 18, infrared receiver and transmitter or transceiver device 22, alignment projection 24 with securing latch 70, and latch release button 74. Securing latch 70 is movable between a locked position 71 and an unlocked position 72. The information device 10 also includes an optional display device 34 or visual display 34 which may be an LCD device, and optional sensing switch 36. While the infrared transceiver 22 is shown and infrared communications described, it should be understood that many other methods of communication can be used, such as radio frequency communication, magnetic induction, direct electrical contact, ultrasound, 802.11 protocols, cellular communications, and the reading of bar codes or magnetic strips. Thus, the information device 10 may include, additionally, or alternatively, a conventional bar code or magnetic strip reader. As best shown in FIG. 2, the internal components of the information device 10 include a processor 50, power source or battery 54, battery cover 58, and latch movement gear 78. It should be understood that the power source 54 may be a solar energy device, or it may be an external device providing energy by magnetic coupling or radio frequency transmission.

Figure 5:
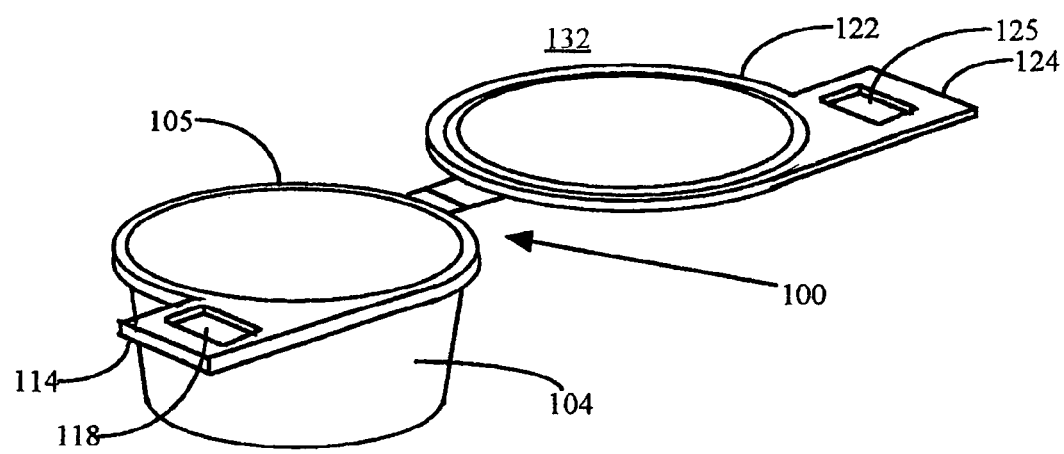
FIG. 5 is a perspective view of a portable medication container in an open position.
Figure 6:
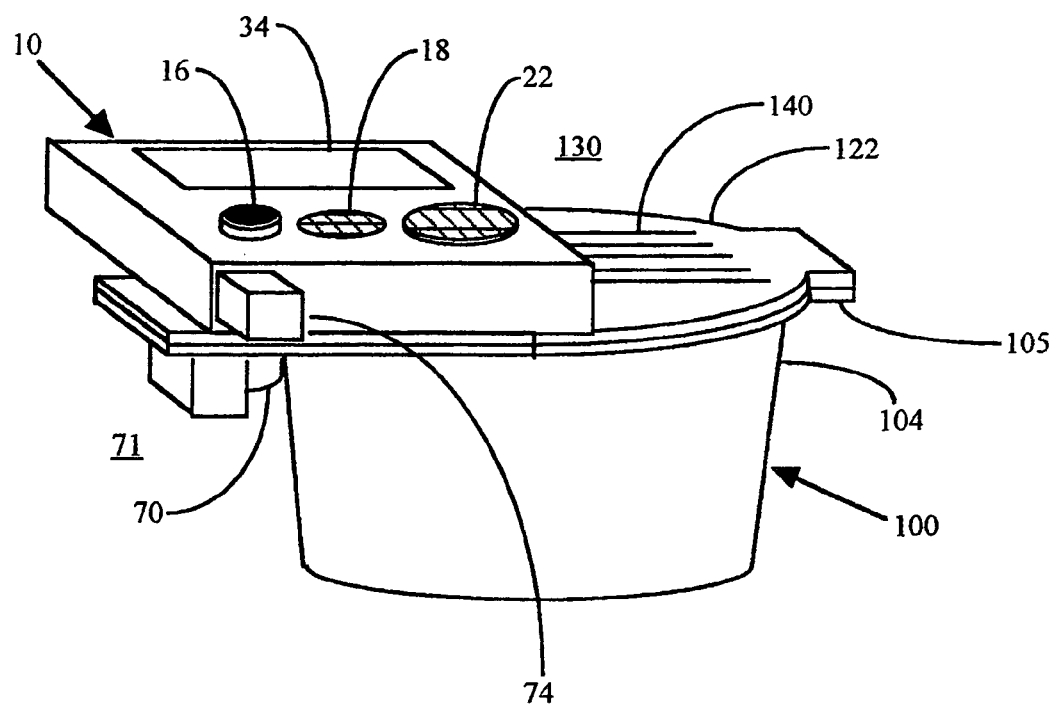
FIG. 6 is a perspective view of the portable medication container with the information device attached thereto and locking the container into its closed position.

A portable container 100 is shown in FIGS. 2, 5, and 6. The portable container 100 includes base 104 forming compartment 108. The container 100, and thus the compartment 108, may be sized and shaped to hold any desired item or items of interest. For exemplary purposes, the compartment 108 illustrated in the figures is for holding a prescribed dose of medication 110. The base 104 has a rim 105 that forms an open top. One side of the rim 105 has an integral, projecting tab 114 with a hole 118 formed through its middle portion. The container 100 includes container lid 122 that is hingably attached to the other side of the rim 105. Lid 122 also has an integral, projecting tab 124 with a hole 125 formed through its middle portion. As shown in FIGS. 2 and 6, the hole 118 in the tab of the rim 114 is adapted to align with the hole 125 in the tab of the lid 124 when the lid is in a closed position 130. The holes 118 and 125 combine to form an opening 126 when in this closed position 130. The information device 10 is adapted to attach to the portable container 100 when the lid is in its closed position 130. The alignment projection 24 of the information device 10 passes through the opening 126 and combines with the forward extension of the securing latch 70 to prevent base 104 and lid 122 from separating and moving to an open position 132.

Figure 3A:
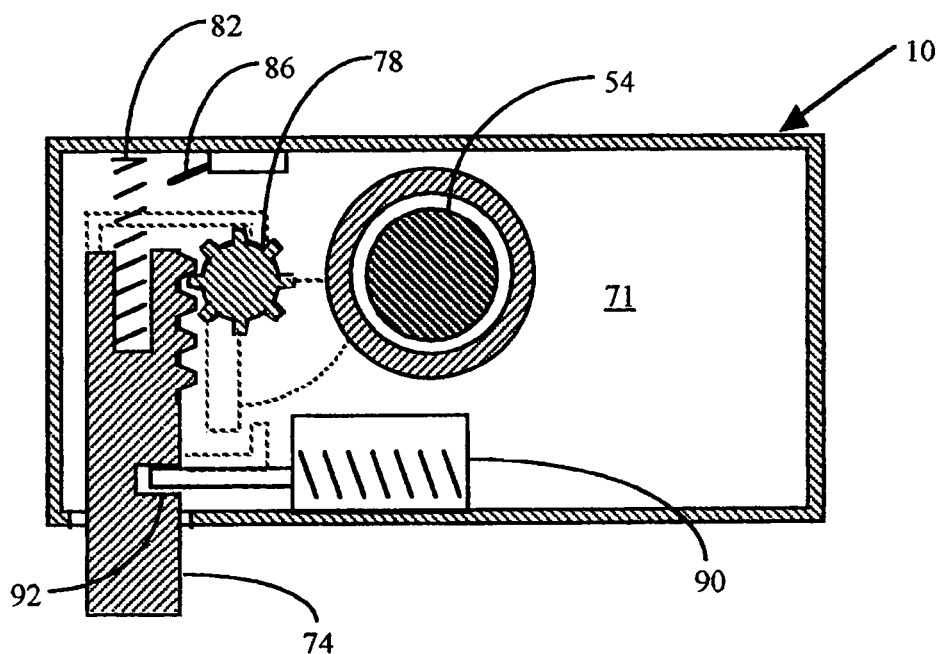
FIG. 3A is a sectional view of FIG. 2 taken along line 3-3 showing the locking mechanism of the information device with its latch in a locked position.
Figure 4A:
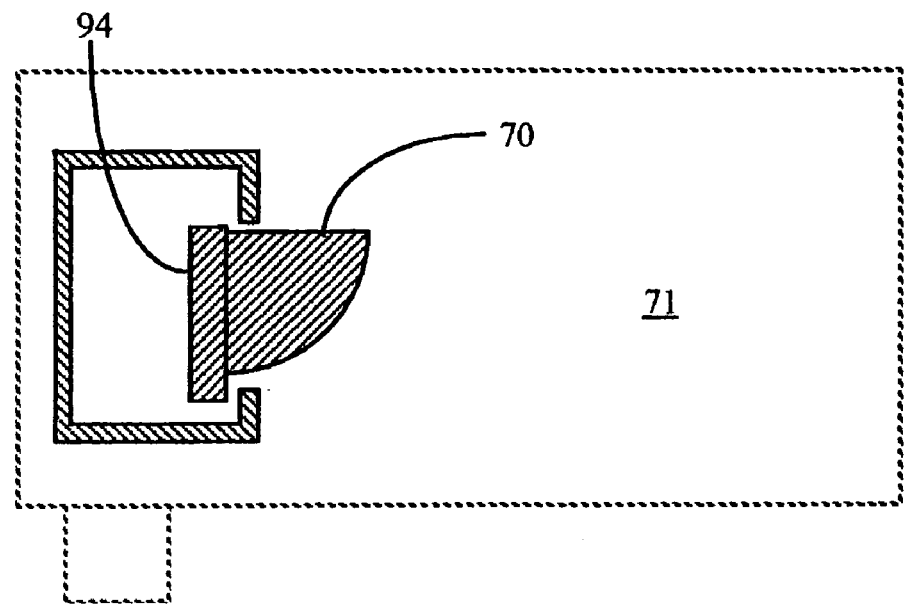
FIG. 4A is a sectional view of FIG. 2 taken along line 4-4 showing the locking mechanism of the information device with its latch in its locked position.

In FIGS. 3A and 4A, the securing latch 70 is shown in its locked position 71. Latch release spring 82 biases latch release button 74 into its extended position. An electric switch 86 is used to sense the motion of the button 74. An optional latch release solenoid 90 and the geared rack engage latch movement gear 78. A movable rod of latch release solenoid 90 is biased to extend into slot 92 to prevent the latch release button 74 from moving. The latch 70 includes a backing door 94 to keep foreign material out of the information device 10.

Figure 3B:
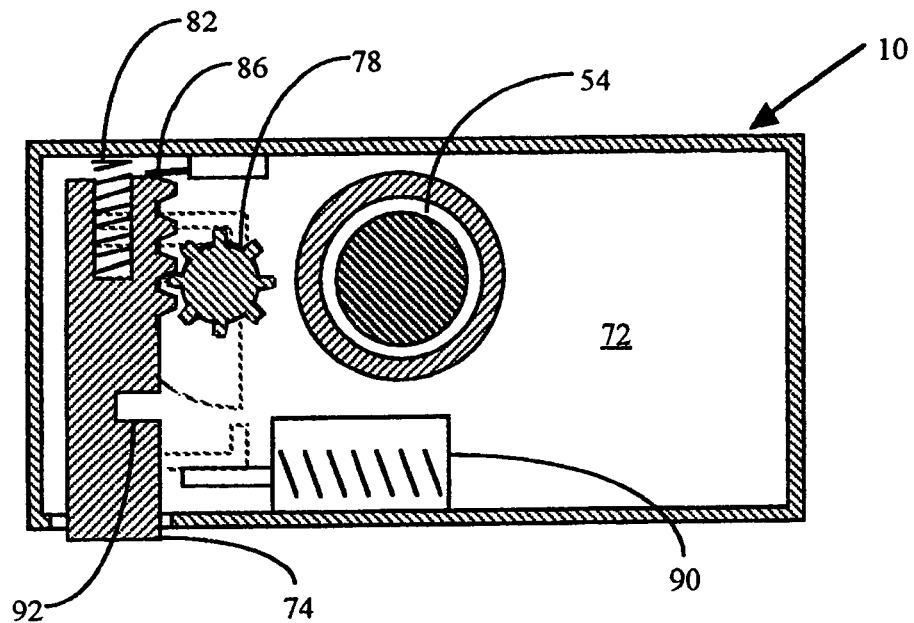
FIG. 3B is a sectional view of FIG. 2 taken along line 3-3 showing the locking mechanism of the information device with its latch in an unlocked position.
Figure 4B:
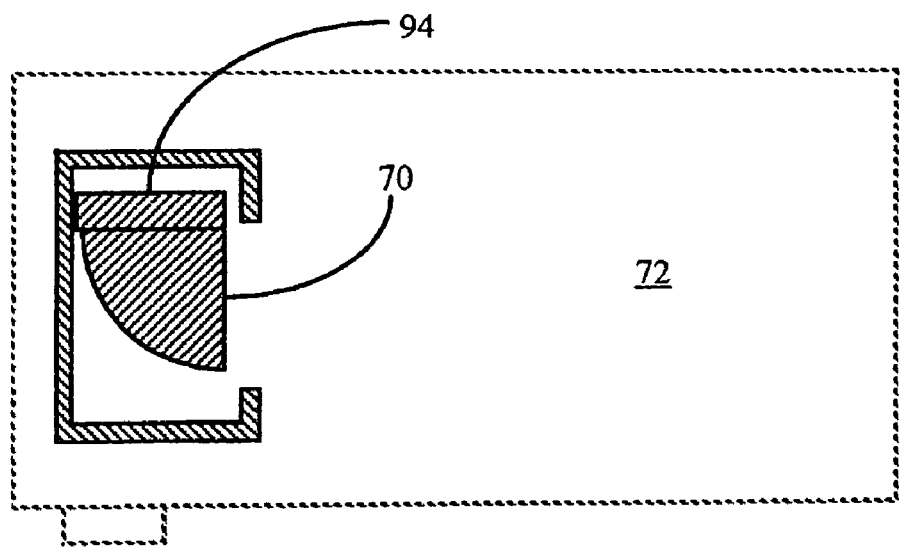
FIG. 4B is a sectional view of FIG. 2 taken along line 4-4 showing the locking mechanism of the information device with its latch in its unlocked position.

FIGS. 3B and 4B show the securing latch 70 is in its unlocked position 72. Securing latch 70 moves into unlocked position 72 when processor 50 receives appropriate instructions via transceiver device 22 to retract latch release solenoid 90. With the movement rod of the solenoid 90 retracted, latch release button 74 can be depressed to cause latch movement gear 78 to rotate and allow securing latch 70 to swing away from the locked position 71. Electric switch 86 is closed which indicates the button 74 was pressed. When the latch release button 74 is released, spring 82 will again bias the latch release button into its extended position. When the solenoid 90 is deactivated its movement rod will again extend into slot 92, securing latch 70 into its locked position 71.

FIG. 5 shows the portable container 100 in its open position 132. Container 100 may be a disposable container intended for a single use to prevent medication cross contamination. The lid 122 includes a paper label 140 for printing textual labeling information as shown in FIG. 6. Alignment projection 24 can pass through the opening 126 so that the information device 10 can be removed, when securing latch 70 is retracted into its unlocked position 72, but not when the securing latch is extended into its locked position 71. FIG. 6 shows information device 10 secured to container 100 in its closed position 130. The latch 70 is in its locked position so that the container 100 cannot be opened. The doses of medication are locked inside the closed container 100. The display device 34 is provided to display a desired portion of the information contained in memory contents 500 of the information device 10. See FIG. 17, as discussed below.

Figure 7:
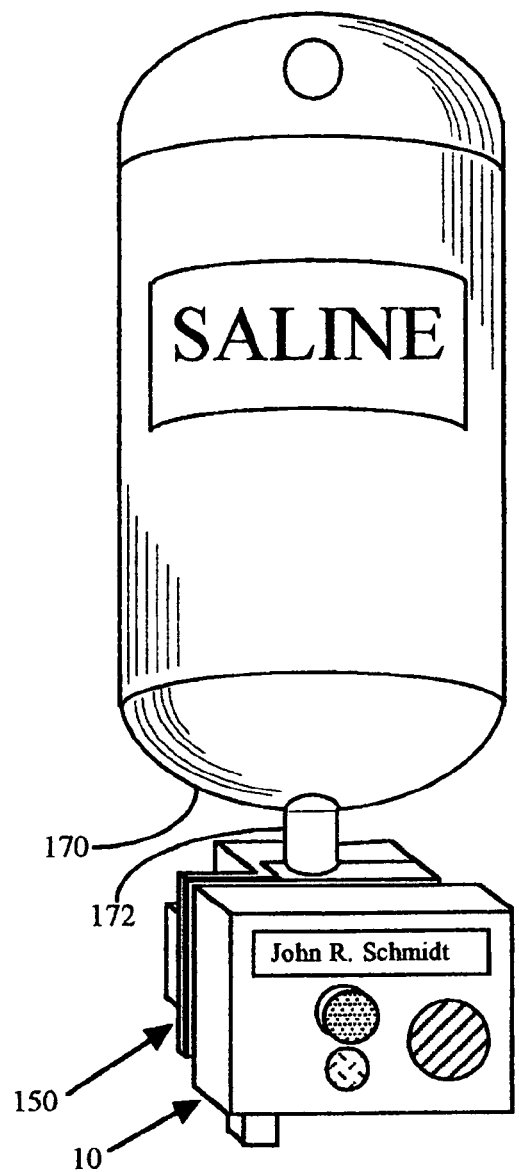
FIG. 7 is a perspective view of an information device attached to a securing device that is secured to a fluid bag for holding IV or blood solutions, the securing device being in a locked position to prevent access to the IV solution via a nipple or tip of the fluid bag.
Figure 8:
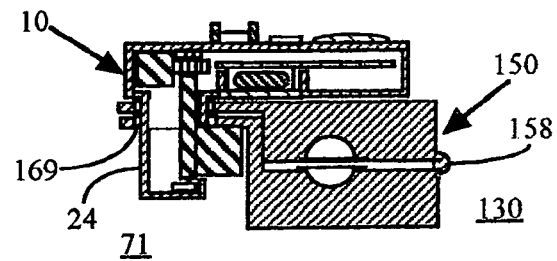
FIG. 8 is an elevated sectional view of an information device and securing device in its locked position.
Figure 9:
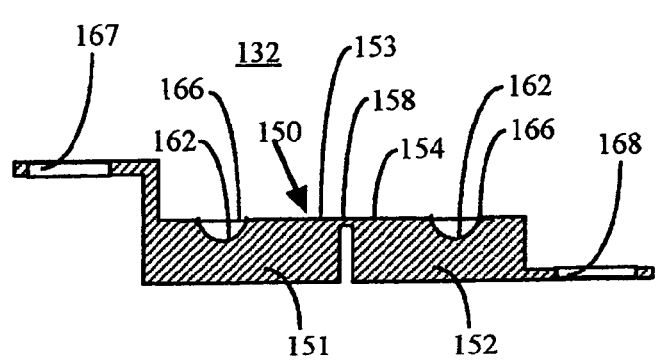
FIG. 9 is an elevated sectional view of a securing device in an open position to allow access to the nipple or tip of the fluid bag.

FIGS. 7 to 9 show the information device 10 used in conjunction with a fluid bag securing device 150 and a fluid bag 170. The information device 10 assists in the electronic labeling of fluid bag 170 containing IV solutions or blood. Securing device 150 is an integral piece of plastic with first and second clamping portions 151 and 152 with upper surfaces 153 and 154. The clamping portions are joined by a living hinge 158 located proximal the upper surfaces. Each clamping portion has a recess 162 and a pressure ridge 166. As shown in FIG. 8, the hinge 158 enables the clamping portions to fold so the recesses 162 and pressure ridges 166 can tightly surround an extended tip 172 of fluid bag 170 preventing flow or normal use of the fluid bag 170. When securing device 150 is folded, holes 167 and 168 form opening 169 allowing alignment projection 24 to pass through when securing latch 70 is retracted, but not when it is extended. FIGS. 7 and 8 show the securing device 150 in closed position 130 surrounding and securing fluid bag tip 172 with the information device 10 attached in locked position 71.

FIG. 10 shows an integral portable container and information device 190 which may be used for IV bags 170, syringes, body tissues, body organs, or other larger objects such as personal items or items used in, e.g., manufacturing, industrial or other processes. The information device 10 is an integral part of the covering lid. Optional data entry buttons 194 are provided to enter data or modify information about medication given to a patient or otherwise concerning the contents of the container 190. It should be understood that data entry buttons 194 could also be provided on information device 10.

Figure 11:
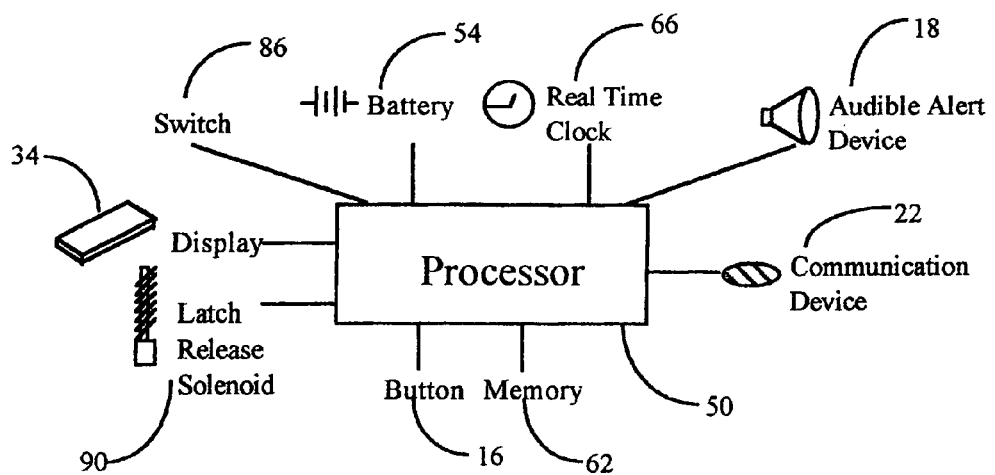
FIG. 11 is a schematic drawing of the electronic circuitry for the information device.

FIG. 11 is a schematic circuit diagram for information device 10 or the information device portion of integral container 190. The information device 10 includes computer processor 50, memory element 62, and real time clock 66 as well as controls to interact with activation button 16, latch release solenoid 90, optional display device 34, battery 54, audible alert device 18, and communication device 22 (which may be an infrared, radio frequency, etc. communication device, or a bar code or magnetic strip reader, etc.).

FIG. 17 shows a list of memory contents 500 maintained in the memory element 62 of the information device 10. The memory contents 500 includes information specific to the information device 10, such as information device data elements 504 which contain a serial number 505, end of battery life data 506, and communication encryption codes 507. As discussed elsewhere herein, the information device 10 may be used in combination with a container 945 having a plurality of individual compartments 950. In such case, the memory contents 500 may also include information on the number of compartments 508.

The memory contents 500 includes information received from other electronic devices, such as the automated or manual dispensing systems 200 or 280 as discussed below. Information received from dispensing systems 200 or 280 can include selected predetermined patient information 520, selected prescribed medication dose information 540, predetermined healthcare worker information 560, dispensed medication information 580, medication information 581 and medication report components 600. Memory contents 500 can further include specific patient information 621 received from a patient identification device 300, a healthcare worker identification device 320, or a patient room information workstation 350 or computer peripheral device 355. Memory contents 500 can include administering healthcare worker information 681 received from the healthcare worker identification device 320.

Memory contents 500 can include consumption information 640 generated during use. Consumption information 640 can include consumption time information (e.g., consumption date and time information) 642 regarding when the portable container was opened 642, offered medication amount information 643 regarding the amount of medication offered to a specific patient 360, and consumed medication amount information 644 regarding the actual amount of medication consumed by the specific patient 360. Memory contents 500 can include a final medication transaction report 660. It should be understood that the memory contents 500 may include additional elements or fewer than shown in FIG. 17. For use with a container 945 having a plurality of individual compartments 950, selected memory contents 500 may include information elements unique to selected ones of the compartments. Each of these sources of information and the use of the various information elements 500 can vary based on the intended use of information device 10 such as in a patient verification system, healthcare worker authorization system, medication tracking system, etc. as more fully described below, or in another medical or non-medical application or setting.

Automated Dispensing System

Figure 12:
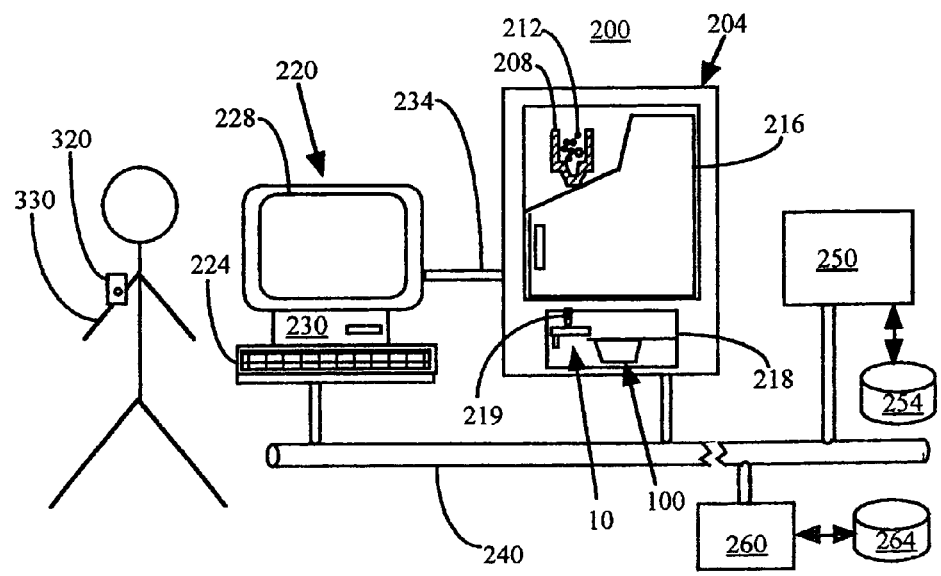
FIG. 12 is a plan view of a healthcare worker using an automated dispensing system that includes a dispensing machine and a medication dispensing workstation, both connected via a hospital network to a pharmacy database and a hospital database.

FIG. 12 shows the automated dispensing system 200 including an automated dispensing machine or unit dose dispenser 204 containing a plurality of bulk medication containers 208 stored inside the dispenser. Each bulk container 208 contains a specific type of medication 212. An access door 216 to the bulk containers 208 is kept locked. Access to the containers 208 is limited to authorized personnel in charge of maintaining the inventory of medication 212 in the dispenser 204, such as the hospital pharmacist. The dispensing machine 204 also contains an access port 218 through which the filled and sealed portable containers 100 are dispensed. A transceiver device 219 is provided for communicating information to the information device 10. Dispenser 204 is used in conjunction with a dispensing workstation 220.

The dispensing workstation 220 includes an input terminal 224 such as a keyboard or a pointer device, and a monitor 228 for communicating with the dispensing machine 204. The workstation 220 also includes a computer processor 230 and program software for controlling the operation of the dispenser 204 and the flow of information and instructions to and from the dispenser. The dispenser 204 or workstation 220 can communicate by a direct communication line 234 or via a hospital network 240. However, it should be understood that the computer processor 230 or an alternate computer processor could be located directly inside the dispenser 204 or included as a part of a hospital network 240.

The hospital network 240 can include its own internal database or can be connected to a pharmacy system 250 with pharmacy database 254 or a hospital information system 260 with a hospital database 264. The internal database or the workstation, or the separate databases 254 and 264 of the pharmacy and hospital systems 250 and 260, contains information pertaining to a plurality of physician orders such as prescription regimens or prescribed medication dose information 540 for administering medication 212 to a plurality of predetermined patients listed in at least one of the databases. The databases include predetermined patient information 520 and corresponding prescribed medication dose information 540 for each patient in the database. The computer processor 230 of the workstation 220 communicates with and obtains information from and relays information to its internal database, pharmacy database 254 or hospital database 264.

A healthcare worker 330 uses the automated dispensing system 200 to obtain prescribed doses of medication 110 for a specific patient 360 under his or her care. Before the dispensing machine 204 dispenses medication 110, the workstation 220 requests the healthcare worker 330 to select one of the predetermined patients in the database. The selected predetermined patient or selected patient should correspond to the specific patient 360 under his or her care. The healthcare worker 330 dispenses the prescribed dose or doses of medication by entering some form of selected patient information 520 that corresponds to the selected patient listed in the database. Alternatively, the healthcare worker 330 can select the name of the desired predetermined patient from a list of predetermined patients in the workstations internal database or by using the hospital information system 260 to locate the desired predetermined patient from the hospital information database 264. The list of predetermined patients to choose from may be limited to those who have been assigned to healthcare worker 330. Having identified the selected patient from the database 262 that corresponds to the specific patient 360 under his or her care, dispensing workstation 220 locates patient medication information 700 (see FIG. 18) for the selected patient in the workstations internal database or by using pharmacy system 250 to locate the information in pharmacy database 254.

Patient medication information 700 contained in the workstation database or associated databases 254 or 264 includes predetermined patient information 520 and corresponding prescribed medication dose information 540 for each predetermined patient. The physician prescription orders determine what prescribed medications correspond to which patient. The database also includes predetermined healthcare worker information 560 that is associated with the prescribed medication dose information. The prescribed medication dose information includes information designating what title or level of authority or clearance an authorized healthcare worker must have to administer the medication to a patient. Predetermined patient information 520 can include patient identification number 521, patient name 522, admitting physician 523, and patient room number 524, and patient blood type 525. The predetermined patient information preferably includes at least patient identification number 521.

Prescribed medication dose information 540 for each prescribed dose of medication 110 can include medication type 541, medication quantity prescribed 542, dosing times 543, and identification of physician prescribing medication 544. Patient medication information 700 can include medication report 720 (see FIG. 24) and universal resource locator 724 (see FIG. 25) which are reformatted by information device 10 as described infra. Predetermined healthcare worker information 560 can include the responsibilities, title, or level of authority of the healthcare worker 561 allowed to give the prescribed medication, healthcare worker identification number(s) 562 allowed to give the prescribed medication, healthcare worker names(s) 563 allowed to give the prescribed medication, and list of patients 564 under care of each healthcare worker. Predetermined healthcare worker information preferably includes the responsibilities, title, or level of authority of the healthcare worker 561.

The computer processor 230 and monitor 228 present prescribed medication dose information 540 for the medications that have been prescribed for the selected patient. The healthcare worker 330 then selects the medication to dispense from this list. Healthcare worker 330 can also enter a medication to be dispensed without the aid of the list or not on the list. In either case, computer processor 230 determines whether the medication is stocked in any of the holding containers 208. If not, an error message will be presented or displayed on the monitor 228. If the medication is available, computer processor 230 causes the dispenser 204 to dispense individual doses of the selected medication 110. As each dose of medication 110 is dispensed, they are placed in the compartment 108 of portable container 100. When all the doses of medication 110 have been dispensed, the lid 122 of the container 100 is closed by dispenser 204 to preventing access to medication.

As medication 212 in the bulk container 208 is dispensed for the selected patient, computer processor 230 creates dispensed medication information 580 for the doses of medication 110 dispensed. Dispensed medication information 580 can include medication information 581, date and time medication dispensed 582, identification of healthcare worker 583 who dispensed medication, and type and quantity actually dispensed 584. Dispensed medication information 580 can also include medication report components 600, medication report 720, and universal resource locator 724 whose use are discussed below.

When all the prescribed doses of medication 110 for the selected patient are dispensed into the portable container 100, selected portions of patient medication information 700 and dispensed medication information 580 are communicated to information device 10 by dispenser 204 using transceiver device 219 via a dispensing signal. This is shown in steps 800, 860, and 910 in FIGS. 29A, 30A, and 31A. The transferred information is stored in the memory element 62 of the information device 10. The use of the selected portions of patient medication information 700 vary based on the intended use of information device 10 such as in a patient verification system, healthcare worker authorization system, medication tracking system, etc., as more fully described below.

Information device 10 may intermittently turn itself off to conserve power when stored in the dispenser during periods of non-use. The dispenser 204 can press activation button 16 to initiate the transfer of data. The data received by the information device 10 can be communicated back to the dispenser 204 as part of a verification process.

Once information device 10 receives the dispensing signal, computer processor 230 sends a message to the information device 10 to retract the latch release solenoid 90. The dispenser 204 automatically presses the latch release button 74 to cause securing latch 70 to swing to its unlocked position 72. This step may also be accomplished manually by healthcare worker prior to inserting the information device 10 into the dispenser 204. Latch release button 74 also makes contact with electric switch 86 which is sensed by processor 50 and causes latch release solenoid 90 to be biased to return to its extended position. Projection 24 of the information device 10 is now aligned with and moved along a path of travel so that the projection passes through the opening 126 formed by the base 104 and closed lid 122. The bottom surface of the information device 10 now rests on the upper surface of the lid 122 of the container 100. Latch release button 74 is then released to allow the spring 82 to force latch release button to move into its extended position 71, so that securing latch 70 rotates to its extended or locked position 71. The upper surface of the latch 70 now abuts the lower surface of the rim 105 of the container 100. Latch release solenoid 90 then enters slot 92, which prevents securing latch 70 from moving out of its locked position 71. The container 100 is now removed from dispenser 204 through access port 218. Access port 218 can be secured to prevent removal of container 100 until information device 10 has been secured and locked to the portable container 100.

When prescribed dose or doses of medication 110 are dispensed into portable container 100, the dosing times 543 or time ranges for when the medication is to be administered can be included with the dispensing signal transferred to information device 10. Dosing times 543 are used by processor 50 in conjunction with real time clock 66 to prevent latch release solenoid 90 from being retracted until the prescribed time or time range is reached. This feature helps prevent the healthcare worker 330 from administering the medication inside the container 100 to the specific patient 360 under his or her care too soon. Processor 50 can also use its audible alert device 18 to issue a reminder tone when the time or time range is reached. This tone is used to indicate to the healthcare worker 330 transporting the medication that it is time to administer doses of medication 110 to the predetermined patient.

Manual Dispensing System

Figure 13:
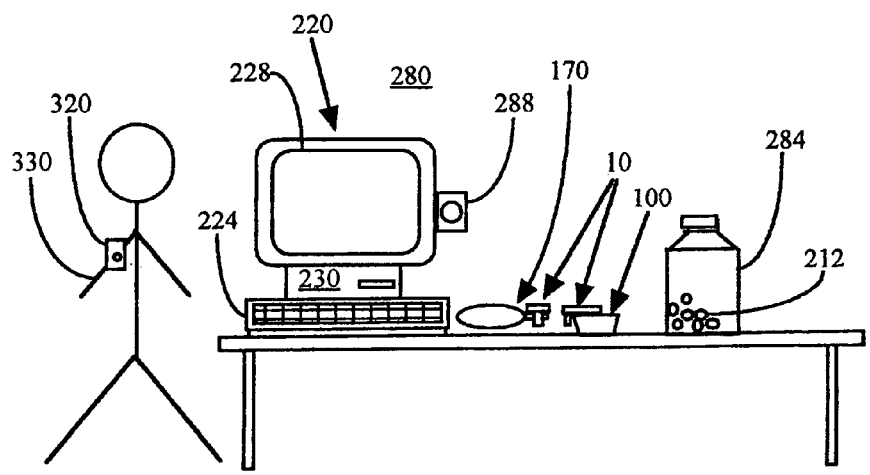
FIG. 13 is a plan view of a healthcare worker using a manual dispensing system with the healthcare worker using the dispensing workstation for manually dispensing medication and labeling medication containers.

FIG. 13 shows the manual dispensing system 280 which includes dispensing workstation 220. Healthcare worker 330 manually locates a bulk medication container 284 holding a quantity of a specific type of medication 212 for dispensing to a specific patient 360 under his or her care. Healthcare worker 330 then removes the prescribed dose or doses of medication 110 from container 284 and places these doses in compartment 108 of portable container 100, and closes lid 122. Healthcare worker 330 then uses workstation 220 to identify the medication and the amount of that medication that has been selected and placed in the container 100 for administering to the predetermined patient. Healthcare worker 330 may also use input terminal 224, to identify the medication selected for administering to the selected patient from patient medication information 700.

When all the prescribed doses of medication 110 for the selected patient are manually dispensed into portable container 100, selected portions of patient medication information 700 and dispensed medication information 580 are communicated to information device 10 via communication port 288 which transmits the initial dispensing signal to the information device 10 for storage in memory element 62. If the patient medication information 700 is not available, portions of selected patient information 520 and predetermined healthcare worker information 560, as entered by healthcare worker 330 using workstation 220, may be sent as part of the dispensing signal. This is shown as steps 800, 860, and 910 in FIGS. 29A, 30A, and 31A.

The healthcare worker 330 manually secures the information device 10 to the container 100. This is done by closing the lid 122 of the container, pressing latch release button 74, inserting the projection 24 of the information device into the opening 126 of the container. The bottom surface of the information device 10 now rests on the upper surface of the lid 122 of the container 100. The healthcare worker then releases latch release button 74 so that latch 70 is biased by spring 82 into its locked position 71. The upper surface of the latch 70 now abuts the lower surface of the rim 105 of the container 100. The information device 10 and portable container 100 are now in the closed and locked positions 130 and 71, which prevents the container from inappropriate opening.

The workstation 220 can also be used to aid in manually preparing a fluid bag 170 for administering to the predetermined patient as in FIG. 13. Various medications are prepared and mixed in fluid bag 170. Once the medication is mixed and the fluid bag is filled, securing device 154 is placed around the fluid bag tip 172 of the fluid bag. The information device 10 is then attached in locked position 71 to the securing device 154 to prevent the inappropriate use of the fluid bag 170.

Information device 10 contains portions of dispensed medication information 580 regarding each medication mixed in fluid bag 170. Dispensed medication information 580 can be written to information device 10 by workstation 220 as each medication is mixed as part of the dispensing signal. Workstation 220 is used to transfer portions of selected patient information 520 and predetermined healthcare worker information 560 to information device 10. This transfer of the selected patient identification information is done either at the time the medication is mixed in fluid bag 170 or before the fluid bag is transported to the patient to whom it is to be administered. In this manner, medication is premixed in fluid bag 170 and stored in a convenient location so that healthcare worker 330 has quick access to the premixed fluid bag, yet portions of predetermined patient information 520 can still be added to information device 10 prior to transportation to the specific patient 360.

Communication port 288 is used to read dispensed medication information 580 stored in the information device 10 previously attached to a fluid bag 170 containing premixed medication. Healthcare worker 330 then uses workstation 220 to communicate with pharmacy system 250 to verify that the medication in fluid bag 170 has been prescribed for the predetermined patient. The workstation 220 will inform the healthcare worker 330 if the medication in fluid bag 170 is prescribed for the selected patient and alert healthcare worker 330 if it is not. If it is intended for the selected patient, workstation 220 can transmit a supplemental signal containing the selected predetermined patient information 520 to information device 10.

Container 100 or fluid bag 170 with securing device 154 are now secured and locked in closed position 130 by information device 10, and are ready for transport to a specific patient 360 in a particular hospital room 380.

Patient Verification System

Figure 15:
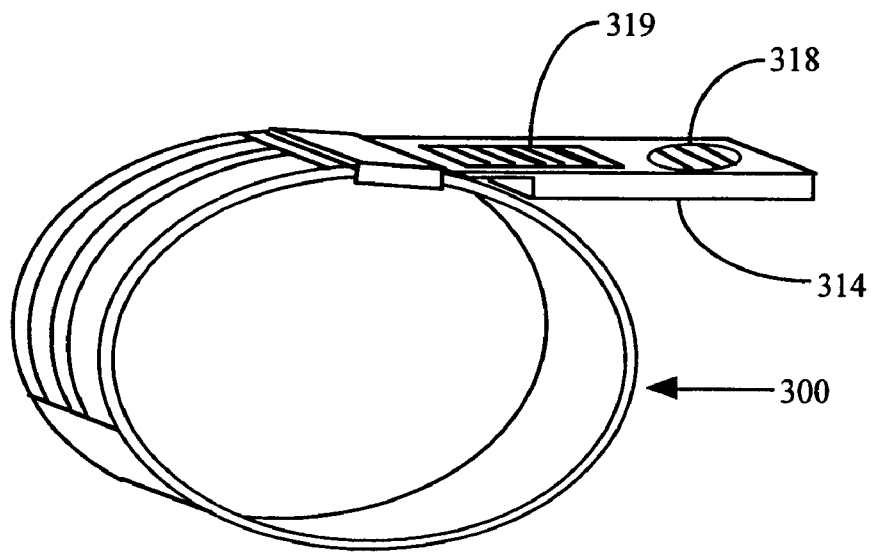
FIG. 15 is a perspective view of a patient identification device.
Figure 16:
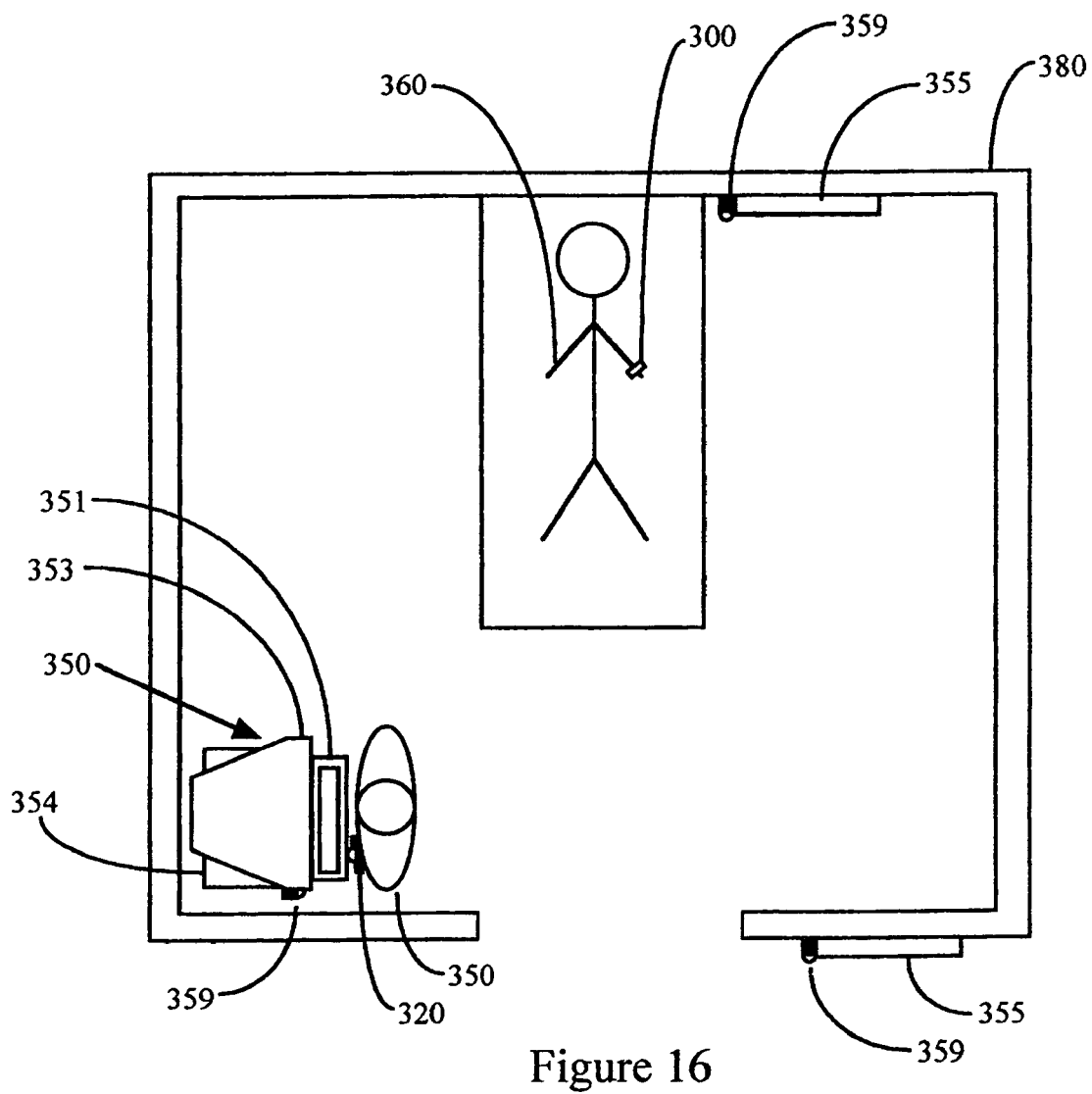
FIG. 16 is an overhead plan view of a hospital room with a specific patient in a bed and an administering healthcare worker at an information station containing a computer and electronic equipment.
Figure 29A:
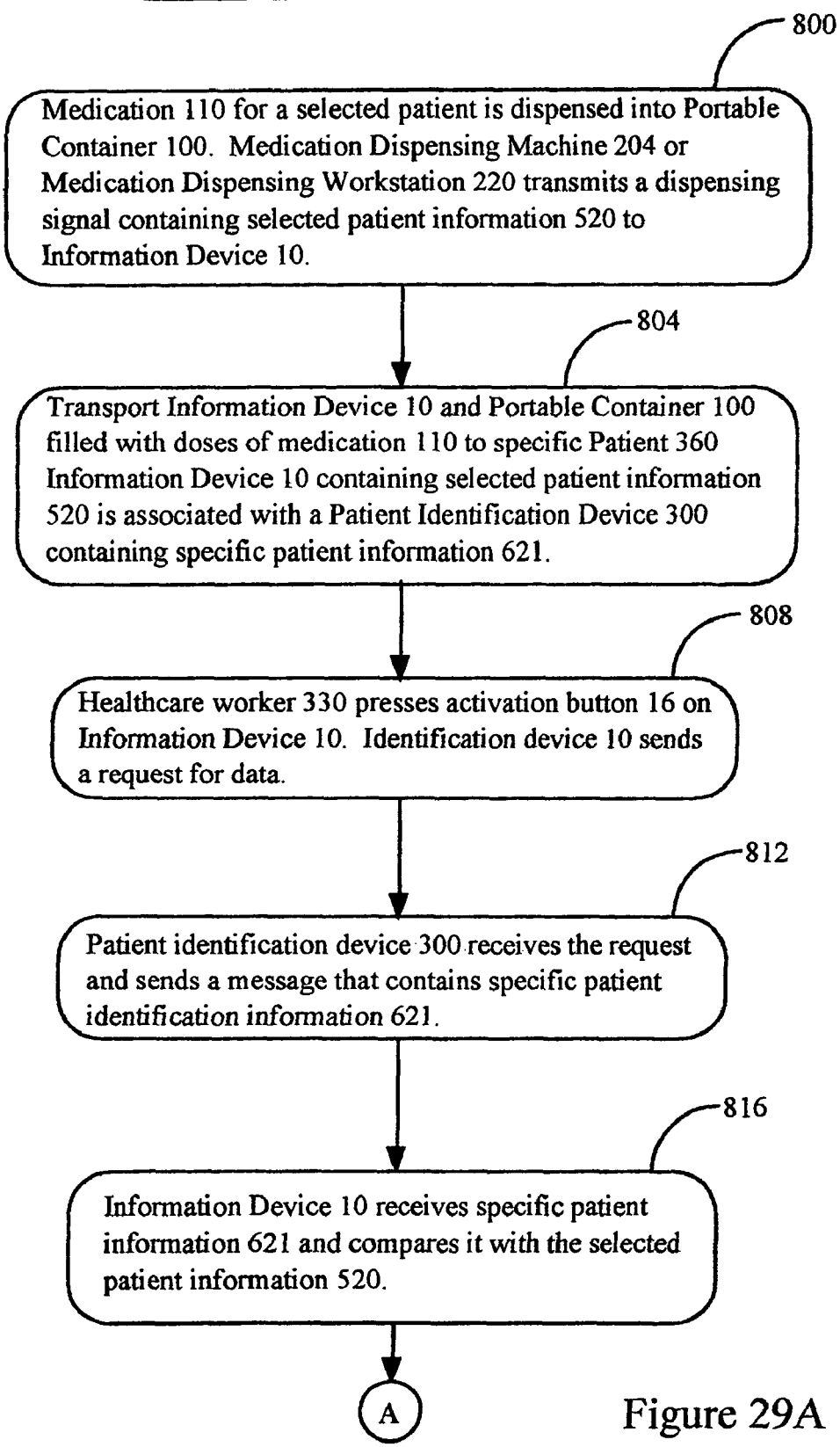
FIGS. 29A and 29B are a flowchart showing the steps in verifying that medication is administered to the specific patient for whom the medication was prescribed as in a patient verification system.
Figure 29B:
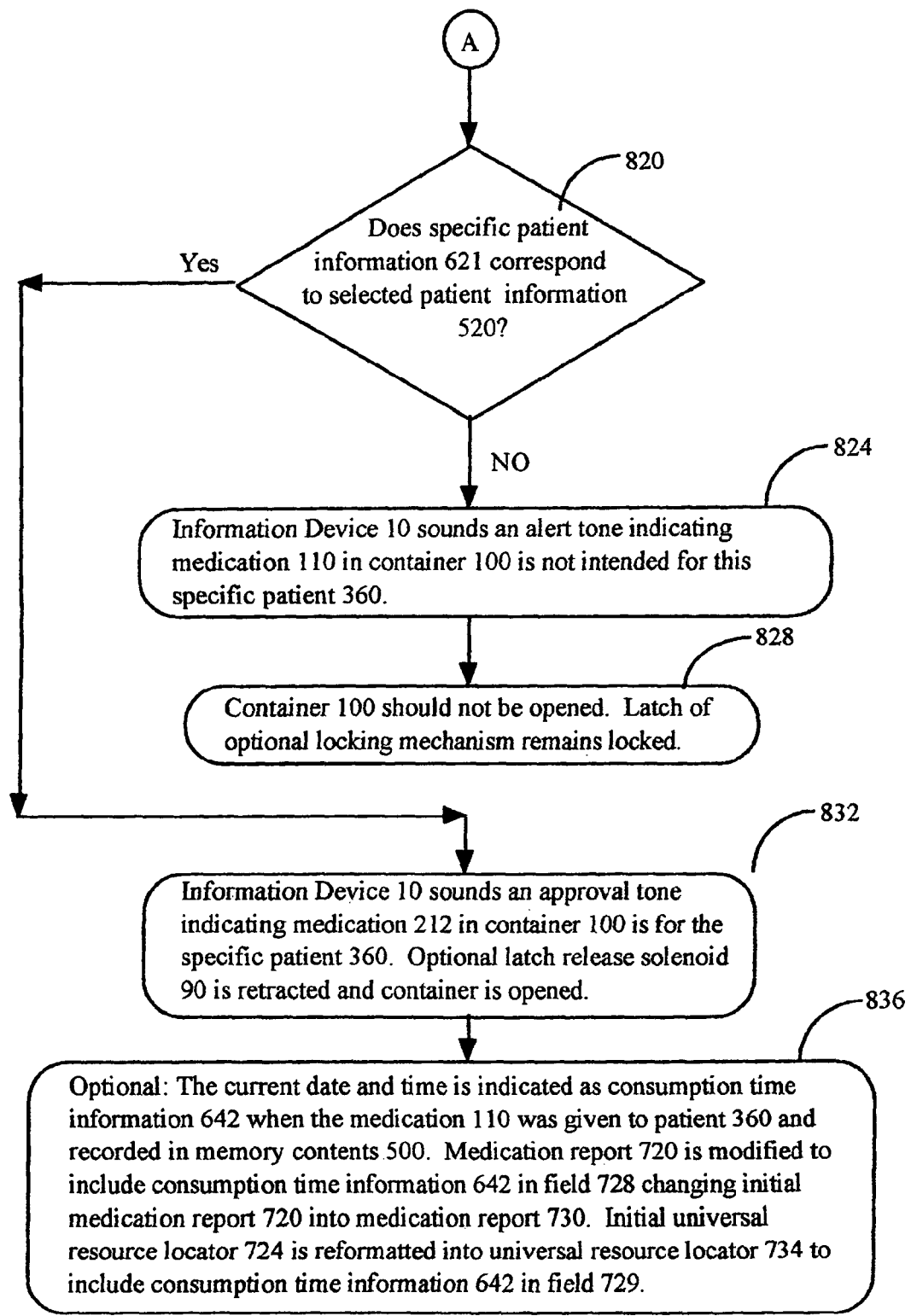

A patient verification system is accomplished by providing the specific patient 360 with patient identification device 300 as in FIGS. 15 and 16. Patient identification device 300 can take the form of a wrist bracelet. Patient identification device 300 may include a processor 314 and a communicating device 318 that is compatible with the information device 10. Memory contents 620 is held in a memory of processor 314. FIG. 20 provides a list of information contained in the memory of the patient identification device 300. Memory contents 620 can include specific patient information 621, such as patient identification number 622, patient name 623, list of medications to which patient is allergic 624, admitting physician 625, and patient blood type 626. While specific patient information 621 is shown as a list of data, the list is may include additional data elements or fewer than shown. Preferably specific patient information 621 contains at least patient identification number 622. Such information may also or alternatively be stored in bar code or magnetic strip form, such as on a bar code label 319 attached to the identification device 300. A flowchart showing a series of steps 800-836 for performing the patient verification system is shown in FIGS. 29A and 29B.

Communicating device 318 transmits specific patient information 621 for the specific patient 360 (step 800). When container 100 and attached information device 10 are brought near to patient identification device 300 (step 804), healthcare worker 330 presses activation button 16 (step 808). This causes information device 10 to transmit a signal that is received by the patient identification device 300. Patient identification device 300 responds by transmitting a verification signal containing the specific patient information 621 that is received by the information device 10 (step 812). (Alternatively, information may be read from the identification device 300 by the information device 10 using a bar code reader, magnetic strip reader, or the like.) The computer processor or comparison device 50 of the information device 10 compares portions of specific patient information 621 with corresponding elements of selected patient information 520 stored in the memory contents 500 of the information device (step 816). While the specific patient information 621 is stated to be transmitted to the information device 10 for comparison with the selected predetermined patient information 520, it should be understood that this information could be transmitted to a different comparison device such as a healthcare worker identification device 320, an information workstation 350, or a computer peripheral device 355 for comparison.

When specific patient information 621 corresponds to predetermined patient information 520 (step 820), information device 10 provides an approval tone using the audible alert device 18 to indicate that the prescribed dose of medication 110 in portable container 100 are intended for that specific patient 360 (step 832), and latch release solenoid 90 is activated to enable securing latch 70 to be released into unlocked position 72 by healthcare worker 330. Once released, the alignment projection 24 of the information device 10 is removed from opening 126 of container 100 so that the lid 122 can be moved to its open position 132. The term "corresponds to" means that the portion of information being compared matches, agrees with, falls within a range prescribed by, or correlates to the information to which it is being compared.

The real time clock 66 in the information device 10 is used to record consumption time information (e.g., date and time portable container opened information) 642 (step 836). This date and time information corresponds to when the medication 110 is given or administered to the specific patient 360. This consumption time information 642 is recorded in the memory element 62 of the information device 10 as part of consumption information 640. Medication report 720 and universal resource locator 724 are modified to include the date and time container opened information 642 in fields 728 and 729 to create a final medication report 730 as shown in FIG. 26, and the final universal resource locator 734 part of medication report components 670 as in FIG. 27.

When specific patient information 621 differs from or does not correspond to the selected patient information 520, an error tone is sounded by audible alert device 18 (step 824). Latch release solenoid 90 keeps securing latch 70 in its locked position 71 (step 828), so that the healthcare worker 330 cannot open the container 100 and give the medication to the wrong patient. The term "differs" means that the portion of information being compared does not match, agree with, fall within the range prescribed by, or correlate to the portion of information to which it is being compared.

As shown in FIG. 16, the patient verification system can be accomplished by placing a workstation 350 or computer peripheral device 355 in or near the room 380 of the specific patient 360. The workstation 350 or computer peripheral device 355 can broadcast specific patient information 621 using communication device 359 to the information device 10 on request. Workstation 350 includes input device 351, monitor 353, and processor 354. Workstation 350 or computer peripheral device 355 must be known by the healthcare worker 330 to be associated with specific patient 360 and has memory contents 690 including specific patient information 621 as in FIG. 22. This specific patient information 621 is transmitted to information device 10 as described above. The specific patient information 621 preferably includes patient identification number 622.

The patient verification system can also be accomplished by using healthcare worker identification device 320, described below, to receive specific patient information 621 from patient identification device 300, and in turn transmit this data to information device 10 to authorize the unlocking of container 100.

Healthcare Worker Authorization System

Figure 30A:
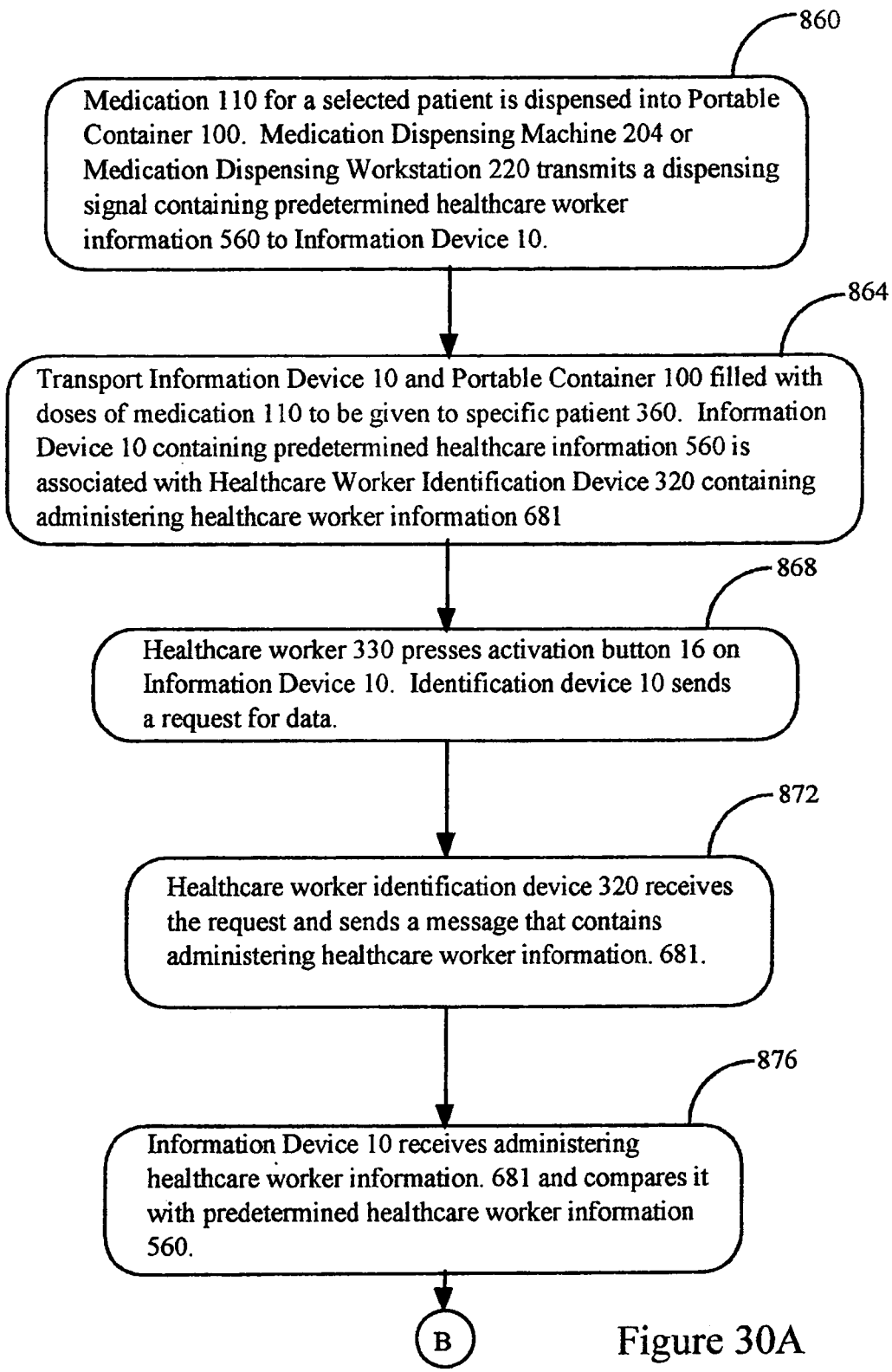
FIGS. 30A and 30B are a flowchart showing the steps in verifying that a specific healthcare worker is authorized to give medication as in a healthcare worker verification authorization system.
Figure 30B:
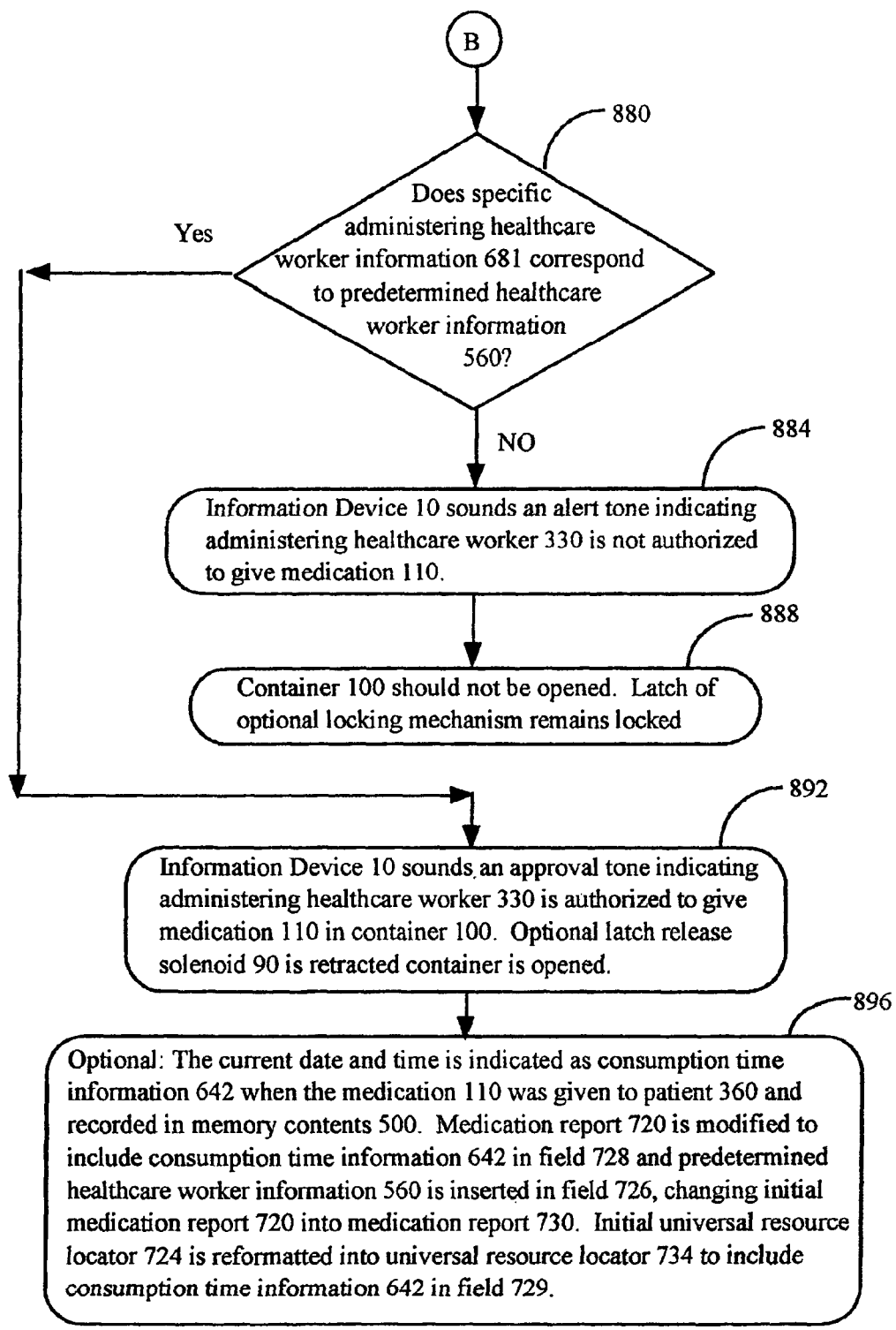

A healthcare worker authorization system can be accomplished by having healthcare worker 330 wear or carry healthcare worker identification device 320 that can communicate compatibly with information device 10. The healthcare worker identification device 320 may take the form of an identification badge as in FIG. 14. Healthcare worker identification device 320 has communication device 322, activation button 324, and processor and memory section 328. A flowchart showing a series of steps 860-896 for performing the healthcare worker authorization system is shown in FIGS. 30A and 30B.

As shown in FIG. 21, the memory contents 680 of the healthcare worker identification device 320 is held in memory of processor 328. Memory contents 680 can include administering healthcare worker information 681, such as responsibilities or title 682, identification number 683, name 684, list of patients 685 under care of healthcare worker 330. While specific administering healthcare worker information 681 is shown as a list of data, the list is may include additional data elements or fewer than shown. Preferably the data includes the responsibilities or title 682 of the healthcare worker 330. Such information may also or alternatively be stored in bar code or magnetic strip form, such as bar code label 329 attached to the identification device 320. Memory contents 680 can also include specific patient information 621 received from patient identification device 300 and final medication transaction report 660 received from information device 10.

The healthcare worker 330 is allowed to unlock the information device 10, and remove it and open portable container 100 by presenting their own administering healthcare worker information 681 to information device 10. When the portable container 100 and attached information device 10 are transported to the specific patient 360 and then brought close to healthcare worker identification device 320 (step 864), healthcare worker 330 presses activation button 16 (step 868). This causes information device 10 to transmit a signal that is received by healthcare worker identification device 320 (step 868). Healthcare worker identification device 320 responds by transmitting an authorization signal containing administering healthcare worker information 681 to information device 10 (step 872). (Alternatively, information may be read from the identification device 320 by the information device 10 using a bar code reader, magnetic strip reader, or the like.) The computer processor or comparison device 50 of the information device 10 compares portions of administering healthcare worker information 681 with corresponding elements of predetermined healthcare worker information 560 stored in the memory contents 500 of the information device (steps 876 and 880). While the administering healthcare worker information 681 is stated to be transmitted to the information device 10 for comparison with predetermined healthcare worker information 560, it should be understood that this information could be transmitted to a different comparison device such as the patient identification device 300, information workstation 350 or computer peripheral device 355 for comparison.

When administering healthcare worker information 681 corresponds to predetermined healthcare worker information 560, information device 10 provides an approval tone using the audible alert device 18 to indicate that the medication in portable container 100 can be administered to patient 360 by healthcare worker 330, and latch release solenoid 90 is activated to enable securing latch 70 to be released by healthcare worker 330 (step 892). Once released, the alignment projection 24 of the information device 10 is removed from opening 126 so that the lid 122 of the container 100 can be moved to its open position 132.

The real time clock 66 in the information device 10 is used to record consumption time information 642 indicating when the medication is given or administered to patient 360 (step 896). This consumption time information 642 is recorded in the memory element 62 of the information device 10 as part of consumption information 640. Medication report 720 and universal resource locator 724 are modified to include predetermined healthcare worker information 560 in field 726 and consumption time information 642 in fields 728 and 729 to create a final medication report 730 and a final universal resource locator 734, part of medication report components 670.

Information device 10 may be used without latch release solenoid 90. Information device 10 has one or more sensors or switches 36 or 86 to detect when container 100 is being opened. Should the healthcare worker 330 attempt to open container 100 by depressing latch release button 74 before specific patient information 621 or administering healthcare worker information 681 is transmitted to information device 10, the first switch 86 will detect the partial retraction of securing latch 70 and sound an advisory alert via audible alert device 18. Healthcare worker 330 can then allow securing latch 70 to automatically close. Should healthcare worker 330 attempt to remove information device 10 from container 100 extra sensing switch 36 detects this and sounds a more pronounced alert tone. The information device will record the inappropriate opening of container 100 for reporting at a later time.

Medication Tracking System

Figure 31A:
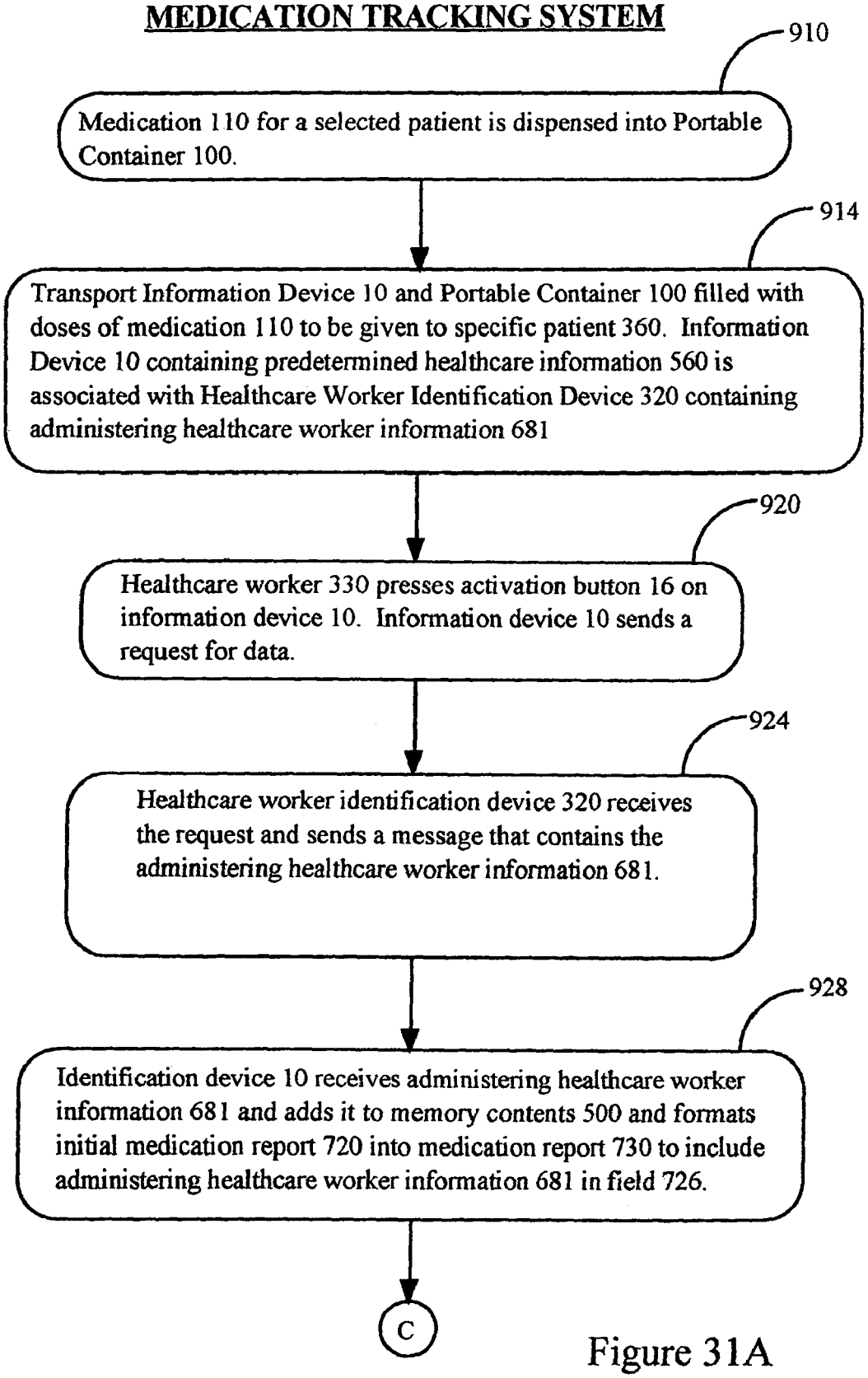
FIGS. 31A and 31B are a flowchart showing the steps in recording which healthcare worker opens a medication container as in a medication tracking system.
Figure 31B:
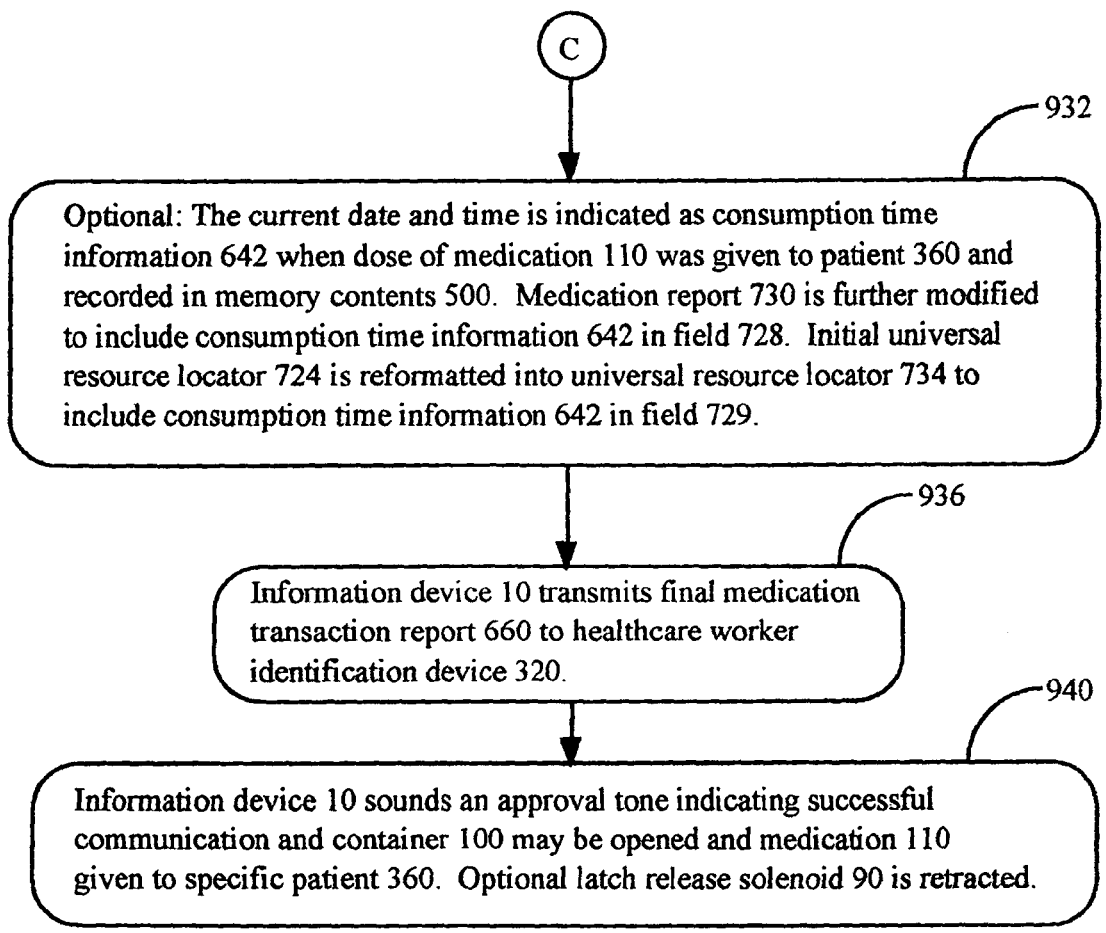

Information device can also be used as a medication tracking system. The healthcare worker 330 is allowed to unlock the information device 10, by presenting their own administering healthcare worker information 681 to information device 10. A flowchart showing a series of steps 910-940 for performing the medication tracking system is shown in FIGS. 31A-31B.

Medication 110 is dispensed into compartment 108 of container 100 for the predetermined patient using techniques discussed above (step 910). The portable container 100 and attached information device 10 are transported to the specific patient 360 (step 914) and then brought close to healthcare worker identification device 320. The healthcare worker 330 then presses activation button 16 (step 920). This causes information device 10 to transmit a signal that is received by the healthcare worker identification device 320 (step 924). Healthcare worker identification device 320 responds by transmitting an authorization signal containing administering healthcare worker information 681. Administering healthcare worker information 681 is received and is added to memory contents 500 and into field 726 of medication report 720 (step 928).

The real time clock 66 in information device 10 is used to record consumption time information 642 indicating when the medication is given or administered to patient 360 (step 932). This consumption time information 642 is recorded in the memory element 62 of the information device 10 as part of consumption information 640. Medication report 720 is further modified and universal resource locator 724 is modified to include consumption time information 642 in fields 728 and 729 to create a final universal resource locator 734 (step 932).

Information device 10 transmits final medication transaction report 660 to healthcare worker identification device 320 (step 936). Information device 10 provides an approval tone using audible alert device 18 to indicate a successful communication and that the medication in container 100 can be administered to a patient by healthcare worker 330, and the latch release solenoid 90 is activated to enable securing latch 70 to be released by healthcare worker 330 (step 940). Once released, the alignment projection 24 is pulled out of opening 126 so that lid 122 can be moved to open position 132.

Transferring Information from the Information Device to an Information System

Workstation 350 or computer peripheral device 355 is also adapted to receive memory contents 500, which can be formatted as final medication transaction report 660, for automatic transfer to pharmacy system 250 or hospital information system 260. This transfer can be done by using hospital network 240. While final medication transaction report 660 is shown as a list of data in FIG. 23, the list may include additional data elements or fewer than shown.

The data in the final medication transaction report 660 may be sent preformatted to comply with the structure of the data recording system, for example, medication report 730 as shown in FIG. 26. Information device 10 may also format and transmit the address where memory contents 500 is to be stored. This may be in the form of universal resource locator (URL) 734 as shown in FIG. 27. In this case, workstation 350 need only send medication report 730 to the address indicated by universal resource locator 734 without interacting with workstation 350, thus keeping workstation 350 completely independent of needing to know how to handle medication report 730. Using the technology of the Internet, medication report 730 can be viewed on a display 740 of a workstation in a doctor's office, home or any workstation 220 or 350 as shown in FIG. 28. Using a browser or general purpose data retrieval, display, and entry program, medication report 730 may displayed by any workstation as seen in medication report browser presentation 744.

Information device 10 is returned to dispenser 204 for reuse. When this is done, memory contents 500, which can be formatted as final medication transaction report 660, is transmitted to dispenser 204 so that memory contents 500 can be communicated to pharmacy system 250 or hospital information system 260, via hospital network 240, and the information device 10 is considered available for reuse. Any error conditions, such as low battery voltage or communication errors, are also transmitted to dispenser 204 from information device 10.

Transferring Information from the Healthcare Worker Identification Device to an Information System The healthcare worker identification device 320 can also receive final medication transaction report 660 or components of it from information device 10. Final medication transaction report 660 can in turn be communicated to the workstation 350 by healthcare worker identification device 320 for communication to pharmacy database 254 or database 264 to automate the recording of the patient receiving.

Using Information Device to Label Medical Samples and Personal Items

The information device 10 can also be used to record patient information regarding blood, fluid, or tissue samples collected from a specific patient 360. A healthcare worker 330 obtains the samples directly from the specific patient 360, places them in compartment 108 and closes lid 122. Healthcare worker 330 then presses activation button 16, and information device 10 is placed in communication with the patient identification device 300 or workstation 350 associated with patient 360. In the same process as explained above, specific patient information 621 is transferred to information device 10. Healthcare worker 330 can manually press latch release button 74 and secure information device 10 to the container 100 to prevent the container from inappropriate opening. The container 100 holding the blood, fluid, or tissue sample is then transferred to the appropriate laboratory for analysis. When received by the laboratory, specific patient information 621 is transferred from information device 10 by communicating with workstation 220, now placed in a laboratory setting, or a laboratory system (not shown). The laboratory will now know from which specific patient 360 the sample came.

A similar process may be used to label a patient's personal items. A patient may enter a medical facility with many valuable personal items, such as hearing aids, jewelry, etc. These personal items are often removed from the patient during treatment. To ensure that such items are returned to the proper patient, and are not misplaced, such items may be stored in a container secured by an information device 10 as described herein. At the time that the personal items are placed in the container, patient identification information is transferred to the information device 10 from the patient identification device 300, or otherwise obtained therefrom. Healthcare worker identification information, obtained by the information device 10 from a healthcare worker identification device 320, may also be stored in the information device 10, to identify the healthcare worker who took the personal items from the patient. The information device 10 will prevent access to the items within the container, or will provide a warning indication, unless the information device 10 is presented the correct identification information from the patient identification device 300 at the time the personal items are to be returned to the patient. For additional security, conventional theft deterrent devices, such as RF detection devices, may be mounted in or on the container or the information device 10 attached thereto. These devices, in combination with a conventional theft deterrent system, may be employed to prevent the container with personal items therein from being removed from, e.g., a hospital or other area without a warning being provided.

For additional security, when specific patient information 621 is read from the identification device 300 by the information device 10, it may be accompanied by a secret code generated by the identification device 300 or the information device 10 at that time. The secret code is recorded, e.g., in the memory of the identification device 300 and the memory of the information device 10. When the container 100 is to be opened, e.g., to return items to a patient, both the patient identification information and the secret code are retrieved from the identification device 300 by the information device 10 and compared with the identification information and secret code stored therein. Access to the container is allowed only if both the retrieved identification information and retrieved secret code match the stored identification information and secret code.

Figure 34:
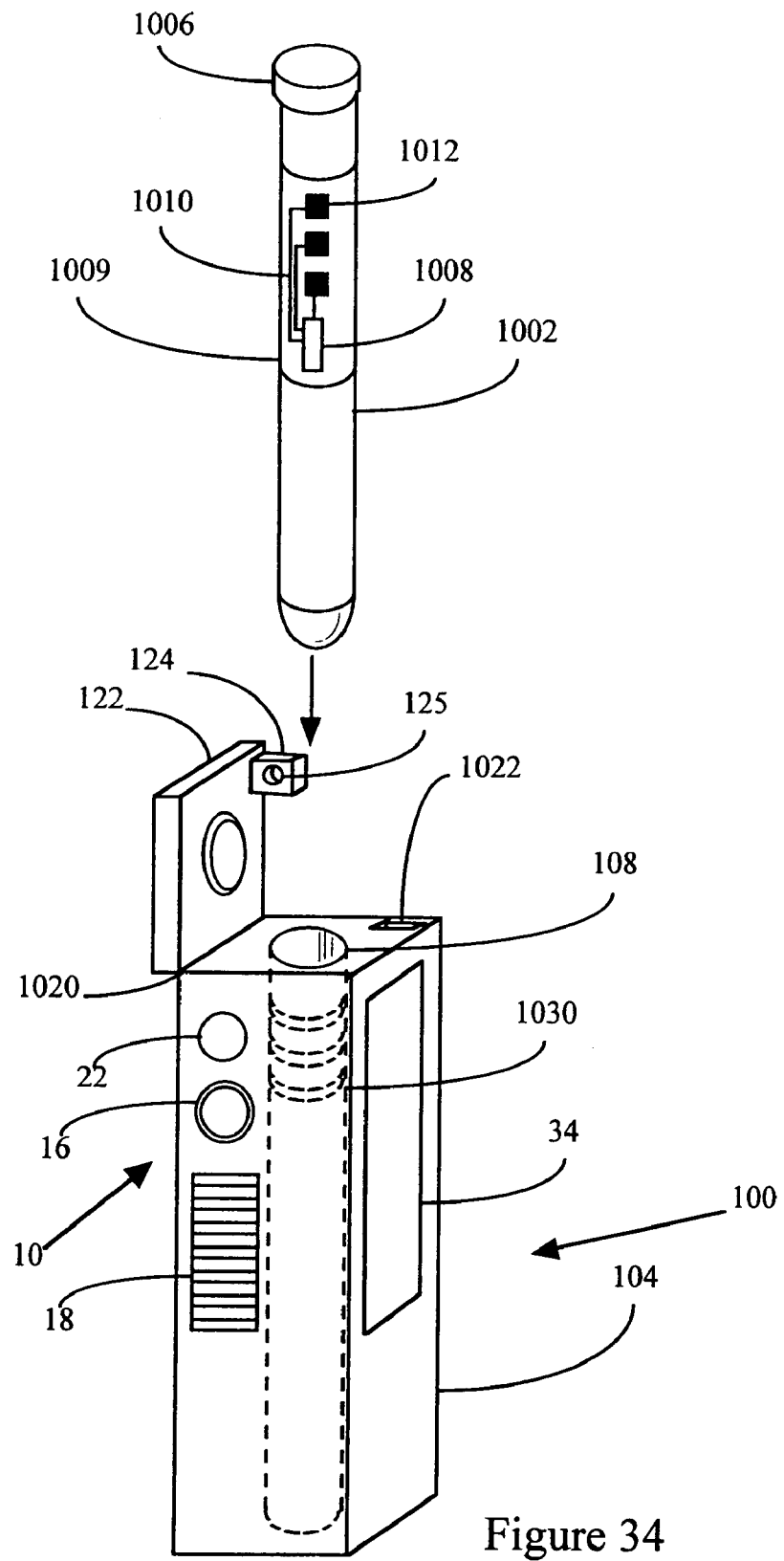
FIG. 34 shows an exemplary system for labeling and identifying medical samples in accordance with the present invention.
Figure 39:
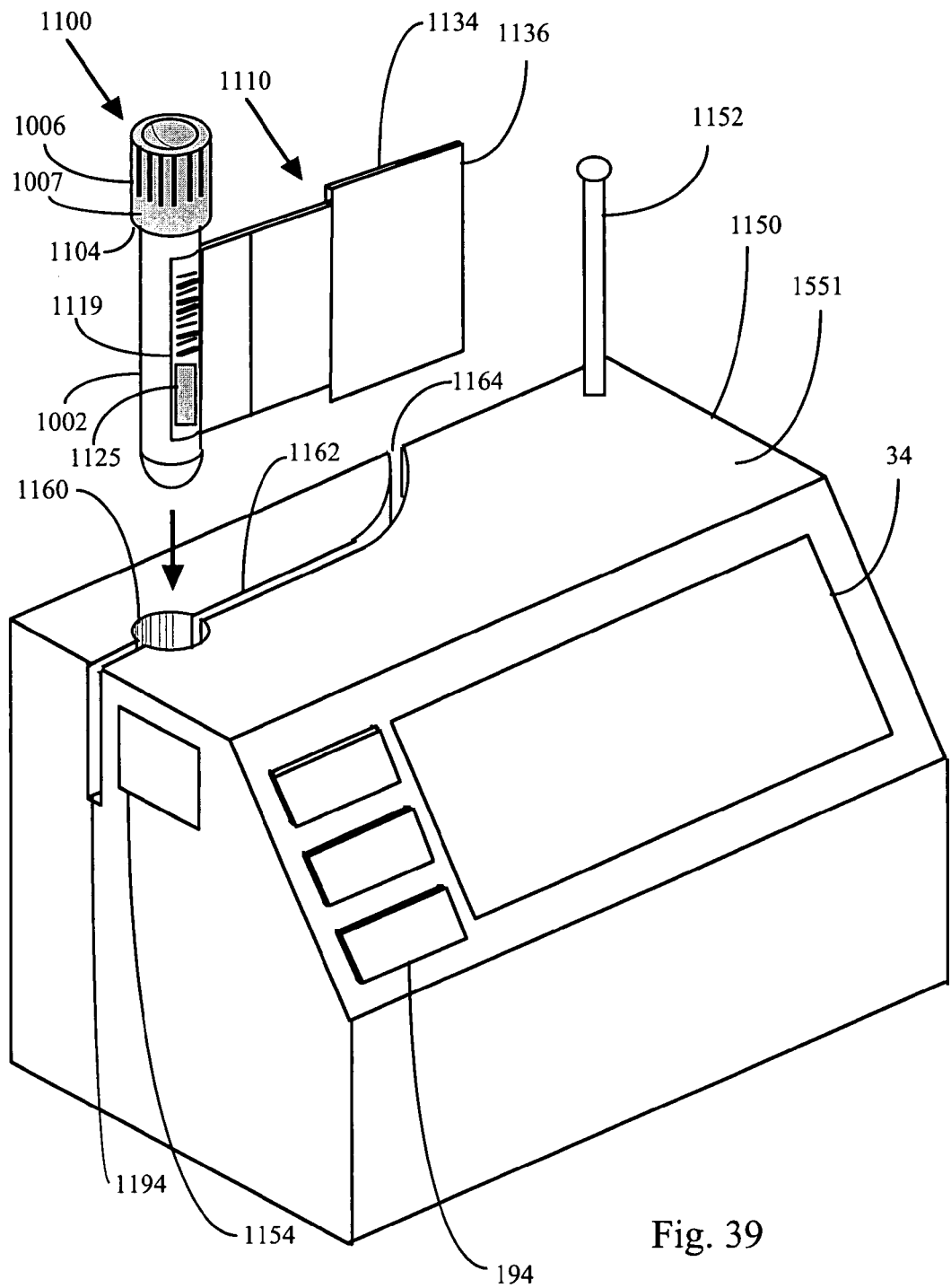
FIG. 39 shows a container verification device and label printer for printing the labels attached to the containers of FIGS. 35 and 37 and the slide of FIG. 45.
Figure 40:
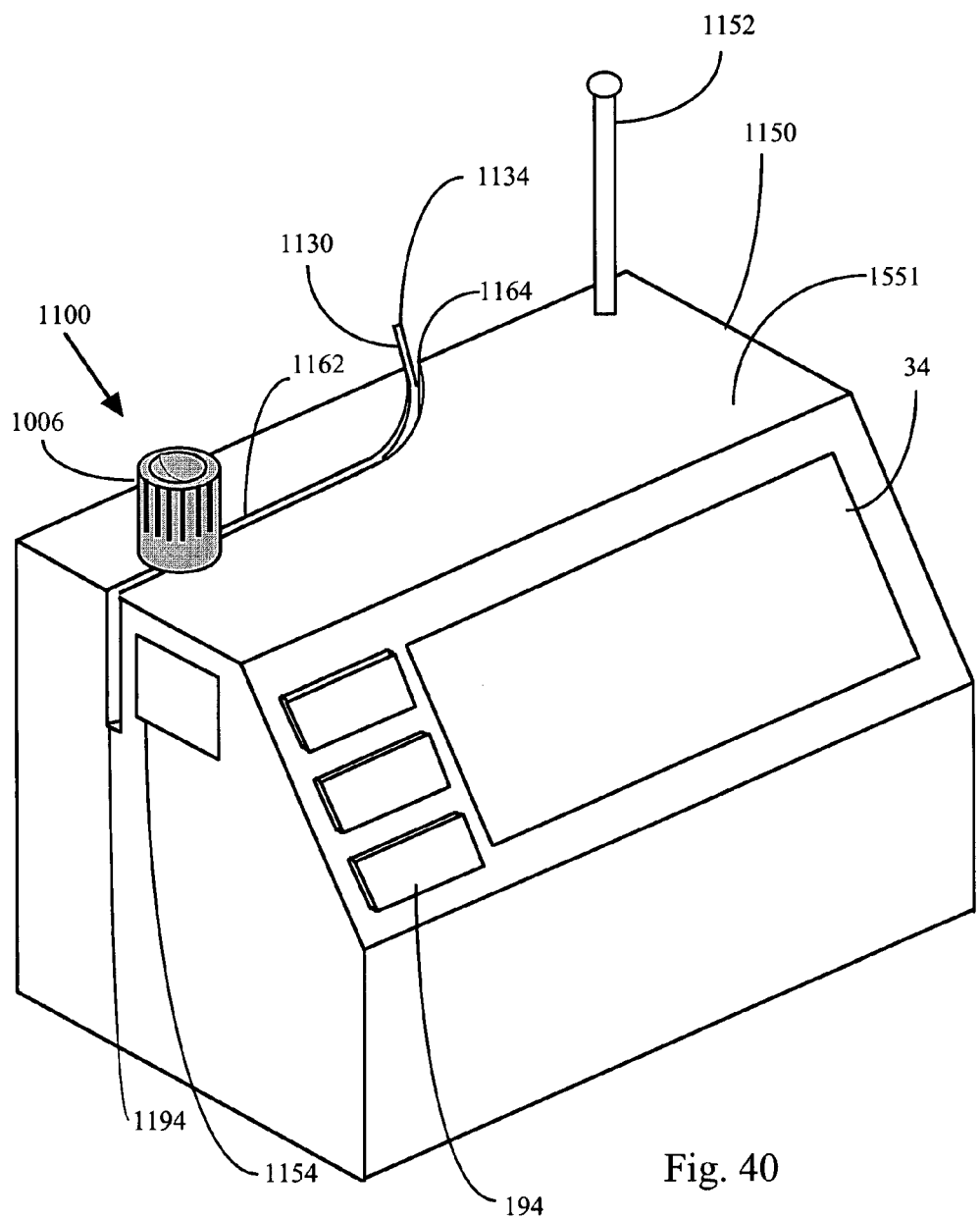
FIG. 40 shows the container of FIGS. 35 and 37 placed in the label printer of FIG. 39 so the partially attached labels can be printed.

Another example of a system for labeling medical samples in accordance with the present invention is shown in FIG. 34. A tube or vial 1002, such as a glass tube, is used to collect blood or other specimens from a patient. (Note that the tube 1002 may be any type of container, including, e.g., a slide, etc. for holding a sample or other item.) For example, tube 1002 may be inserted into a blood syringe to withdraw blood from a patient. After the blood or other sample has been collected, the tube 1002 is closed by a cap 1006. The tube 1002 preferably has an electronic memory device 1008 attached to it. The memory device 1008 may be implemented in a form similar to that used by Smart Cards. The memory device 1008 may be attached to a flex circuit 1009 that includes electrically insulated conductors 1010 leading to exposed electrical contacts 1012. The flex circuit 1009 may be attached to the tube 1002 on the outer surface thereof with an epoxy or other adhesive.

A container 100, as described previously, may be designed to receive and hold the tube 1002. For example, container 100 may include a base 104, a compartment 108 adapted for containing the tube 1002, a lid 122, and a hinge 1020, such as a living hinge. Lid 122 may include a projecting tab 124 with a hole 125 formed therein. The tab 124 is positioned on the lid 122 so as to enter an opening 1022 in the container 100 when the lid 122 is closed. The container 100 may include an integral information device 10, similar to those previously described. The information device 10 may include an activation button 16, a transceiver 22 to read specific patient identification information 621 from a patient identification device 300, as described previously, an optional display 34, and audible alert 18 devices. The information device 10 may include a processor, battery, and memory, as described previously.

An exemplary and typical use of the system illustrated in FIG. 34 follows. After a blood or other sample has been drawn or taken, and placed within the tube 1002, the tube 1002 is capped 1006 and placed in the compartment 108 in the container 100. (Additional compartments 108 may be provided in the container 100 to hold multiple tubes 1002, or one or more large compartments may be formed in the container 100 to hold multiple tubes 1002.) Lid 122 is rotated about hinge 1020 so that projecting tab 124 enters opening 1022, thereby closing the tube 1002 within the compartment 108. A healthcare worker may then press activation button 16 such that information device 10 is placed in communication with a patient identification device 300. In the same process as described previously, specific patient information 621 is transferred from the patient identification device 300 to the information device 10. Such patient information may be displayed on display 34. The information device 10 may also issue an audible acceptance tone using alert device 18 and activate a locking mechanism to lock the lid 122 closed. (The locking mechanism may include a solenoid which is activated to extend into hole 125 formed in the projecting tab 124 to secure the lid 122 to the base 104 of the container 100.) The sample contained in the tube 1002, within the container 100, will be sent to, for example, a laboratory for analysis, bearing the specific patient information 621 from the patient information device 300 in a manner that ensures that the sample will not be confused with a sample from another patient. When the container 100 is received in the laboratory, the specific patient information 621 may be read from the information device 10 positively to identify the patient from whom the sample was drawn.

The compartment 108 formed in the container 100 may be equipped with electrical contacts 1030 designed to mate with the contacts 1012 formed on the tube 1002 when the tube 1002 is placed in the compartment 108. When information device 10 reads specific patient information 621 from an identification device 300, a portion of this information can be written by the information device processor, via contacts 1030 and 1012, to memory device 1008 mounted on the tube 1002. The date and time can also be written to the memory device 1008 by the information device 10. As previously discussed, transceiver 22 can also be used to read healthcare worker information 681 from a healthcare worker identification device 320. The information device 10 may also transfer a portion of this information to the memory device 1008 on the tube 1002. Thus, all necessary identification information may be provided in the memory device 1008 mounted on the tube 1002 itself. Therefore, the information device 10 itself need not include memory of its own for storing such information. When the laboratory removes the tube 1002 from the container 100 for analysis, the laboratory will be able to identify, e.g., which patient the sample came from, the time it was drawn, and who drew the sample, from memory device 1008 mounted on the tube itself.

As a further enhancement, the information device 10 may be previously programmed with selected patient information 520, the type of sample that is to be obtained, and the type of laboratory analysis to be performed on the sample. Compartment 108 may contain one or more empty tubes 1002. Container 100 is brought to the patient and transceiver 22 is used to read specific patient information 621 from a patient identification device 300. A comparison is performed between selected patient information 520 and specific patient information 621. If there is a match, the lid 122 of the container 100 may be allowed to be opened such that the healthcare worker can remove the tube 1002 for use. The type of sample that is to be obtained may be displayed at this time on the display 34.

Updating of Information Relating to Container Contents

An information device 10 attached to a container 100 may preferably be adapted to receive updated information relating to the contents of the container. Such communication may be accomplished in a conventional manner via direct or wireless connection between the information device and a computer network. (Such communications may be received by the information device 10 via the internal communication device 22 or via a separate communication device for receiving such communications.) The updated information relating to the contents of the container may indicate a required change to the container contents. The information device 10 may display such a required change, e.g., on display 34, or provide an audible or other visual indication indicating such a required change. Such a display or indication may be provided when the information is received, when the container is to be opened, or when an identification verification is attempted or performed.

For example, as discussed previously, a container 100 may include medication and an attached information device may include dispensed medication information 580 stored therein. If a patient's prescription changes, e.g., medication is to be added or deleted, after the medication is dispensed into the container, but before the medication is delivered to the patient, this required change may be communicated to the information device, and presented to a health care worker. Thus, a patient can be assured to receive the proper prescription. Information concerning required changes to other information, such as the timing of providing medication to a patient, may also be communicated to the information device.

Infusion Pump Control

Figure 33:
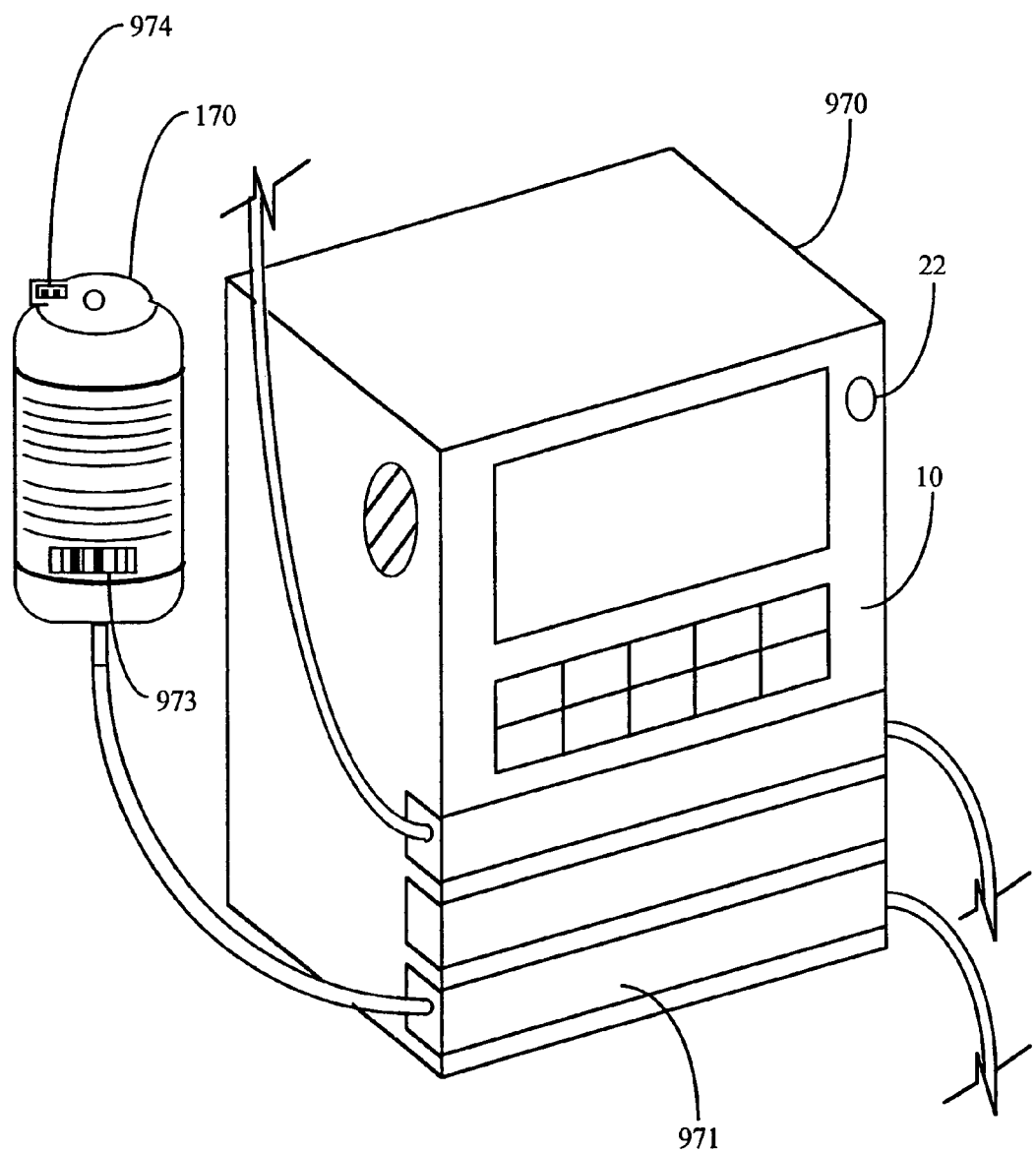
FIG. 33 shows an apparatus including a system for dispensing intravenous fluids according to one embodiment of the invention.

In an alternate embodiment of the invention, as shown in FIG. 33, the information device 10 may be connected to or integrally formed as part of a fluid dispensing system, such as an infusion pump 970. In the event that the information device identification information 520 and the identification device identification information 621, obtained from a patient identification device 300, correspond correctly to each other, then the information device 10 can activate a response function in the form of, e.g., allowing the infusion pump motor to operate to dispense fluid from an IV bag 170, unlocking a compartment 971 on the infusion pump 970 to allow the IV bag 170 to be mounted thereon, and/or providing an audible or visual indication, as discussed previously. Healthcare worker information 681 also may be required to be transferred from a healthcare worker identification device 320 to information device 10, and a comparison performed, in the manner described previously, to determine if the healthcare worker is authorized to operate the infusion pump 970.

In another preferred embodiment, an information device 10 in accordance with the present invention, which is separate from the infusion pump 970, may be employed as part of an infusion pump control system. The infusion pump 970 may include a conventional infusion pump controller which controls, e.g., the flow rate and flow duration from the IV bag 170 (or multiple IV bags). A conventional receiver/transmitter, similar to the receiver/transmitter 22, may be provided in the infusion pump 970 for allowing infusion pump control information (for example, flow rate, duration, and IV type) to be received by the infusion pump controller. The information device 10 may have such infusion pump control information stored therein, and may communicate such information, via the communication device 22, to the infusion pump controller. The information device 10 may be attached to the IV bag 170, as shown, for example in FIG. 7 or the IV bag 170 put in a container including an information device, as shown in FIG. 10. Alternatively, the infusion pump control information, including information identifying for whom the IV 170 is prescribed, may be provided on the IV bag 170 itself, e.g., in the form of a bar code label 973 or memory device 974, such as a conventional RF identification device or solid state memory device, mounted on the IV bag in a conventional manner. In such a case, the information device 10 mounted in the infusion pump would include a conventional device, e.g., a bar code reader, RF identification device reader, etc., for reading the identification information from the IV bag 170. The information device 10 and IV bag 170 (or just the IV bag 170, if the infusion pump control information is provided directly thereon) are transported to the infusion pump where the infusion pump control information is downloaded from the information device 10 (or obtained from the IV bag 170 bar code 973 or memory device 974) into the infusion pump controller, and the IV bag 170 is attached to the infusion pump 970. (A comparison of patient identification information stored in (or on) the information device with patient identification information stored in the infusion pump controller may also be performed, in the manner described above. In this case, the infusion pump controller acts as a peripheral identification device 355 having memory contents including specific patient information.) The infusion pump controller may provide a confirmation indication and/or a signal to the information device 10 that the desired infusion pump control information was received. This confirmation information may be recorded in the information device 10 for later transmission to a database, as described above. Alternatively, the information device 10 may merely store the fact that the infusion pump control information was communicated to the infusion pump controller.

This system may be employed in combination with the identification verification system described above, to ensure that the correct patient receives the correct IV prescription. For example, an information device 10 attached to, or otherwise associated with, an IV bag 170, may include infusion pump control information, including information identifying for whom the IV 170 is prescribed. (Alternatively, as discussed above, such information may be provided by a bar code 973 or memory device 974 mounted on the IV bag 170 itself.) Such information may be read into and stored in the infusion pump controller at the time the IV bag 170 is mounted on the infusion pump 970 and the IV is administered to the patient. As subsequent replacement or additional IV bags 170 are brought to the infusion pump 970, the infusion pump control information, including patient identification information, associated therewith, is obtained by the infusion pump controller. The infusion pump controller, acting as an information device, compares the patient identification information thus obtained with the patient identification information obtained from the first IV bag 170 (e.g., from the information device 10 attached thereto) which was provided to the infusion pump 970. In the event that the identification information corresponds correctly to each other, the infusion pump controller/information device can activate a response function to, e.g., allow the subsequent IV bag 170 to be mounted on the infusion pump 970, allow the infusion pump 970 to dispense fluid from the subsequent IV bag 170, and/or provide an audible or visual (or other) indication. Thus, in this manner, the first IV bag 170 attached to the infusion pump 970 includes patient identification information associated therewith which is read into and stored in the infusion pump information device, to thereby effectively assign the infusion pump 970 for use by a single patient, and no other, thereby assuring that a patient will receive correct IV prescriptions.

Applications in Other Fields

Although the above-described apparatus is of particular use in medical and hospital administration applications, its advantages can be utilized in other fields as well. For example, a verification apparatus in accordance with the present invention may be especially useful in an industrial setting where individual components are shipped from one location to another. As a system for tracking the location and access to certain components, the verification apparatus contains an information device 10, an identification device 300, and a container 100. Industrial components may be locked in the container 100 by a locking mechanism controlled by the information device 10. When an individual wishes to retrieve the components from the container 100, the identification device 300, including identification device identification information 621, is presented to the information device 10. The information device 10 proceeds to compare its own information device identification information 520 with the identification device identification information 621. If the two pieces of information correspond to each other, then a response signal is activated. In one embodiment of the invention, the response signal activates the unlocking of the container 100. Alternatively, or additionally, the response signal may control an audible or visual indication.

It should also be understood that the roles of the information device and identification device described herein may be interchanged for some activities. For example, identification information may be sent from an information device to an identification device, with the comparison of information described above performed in the identification device. If the identification comparison is favorable, the identification device may issue an audible or visual alert and/or send a response signal to the information device to provide an alert and/or unlock the lid of a container.

Application to Container Labeling

FIGS. 35 to 45 show another embodiment of the invention related to the labeling of containers (e.g., blood sample tubes, blood slides, urine samples, or other non-medical containers and objects). These containers have two and in some cases three states. The first state is an empty or substantially empty state. Empty has the normal meaning of being unfilled, while substantially empty means that the container may have a reagent or chemical preservative, but the container is not yet filled for the purpose intended. For example, in the case of a blood tube, the tube may have one or more preservatives or reagents in powder or as a interior coating, but when supplied is not yet filled. When the container is a glass slide, a plastic bio-chip, or diagnostic assay tray it may contain a reagent that causes reaction with a specific blood or other sample obtained from a patient, but is deemed to be substantially empty until a sample is collected in or on it. The container is substantially empty even if the amount of the sample provided to it is only a fraction of the volume or weight of the chemical or reagent added to the container.

The second state is when the container is filled, that is, after a biological sample has been collected. For example, after blood is drawn into a blood tube, or urine into a sample cell, or blood onto a slide. The third state is a testing state, where the filled container is analyzed in a laboratory or laboratory analyzer during which additional chemicals can be added to the container or the container can be subjected to light, radio waves, magnetic pulses, electrical pulses, sound, gravitational effects, or other energy sources.

Specifically, FIGS. 35 and 36 show commonly used blood sample container 1100 with cap 1006 having a central puncture membrane 1102 and tube 1002. The diameter of cap 1006 is D1 and the diameter of tube 1002 is D2 which is less than D1 creating ledge 1104 around the bottom of cap 1006. Partially attached to the vertical wall of tube 1002 is identification label 1110. Label 1110 can be made of paper or special non-tear printable materials can also be used.

Label 1110 is shown consisting of 3 sections; pre-adhered section 1112, spacer section 1114, and printing section 1116 with distal end 1117. Section 1112 is of length L0, for example 2 mm. Sections 1114 and 1116 are not attached to tube 1002 and are of lengths L1 and L2 respectively. The height of label 1110 is H1. Note that label 1110 is positioned so that it is a distance H2 below ledge 1104.

Label 1110 has a front surface 1118 and a back surface at least partially coated with a conventional adhesive coating (not shown) protected by release liner 1120. By removing release liner 1120 the adhesive is exposed allowing a healthcare worker to wrap the exposed adhesive coated back surface of label 1110 around tube 1002, as seen in FIG. 36, now showing distal end attached to tube 1002 and not covering printed section 1116. When desired a gap may be left between distal end 1117 and the adhered end 1119 of label 1110 so the contents of container 1100 can be seen along the vertical wall of tube 1002.

It should be noted that dimension L2 should be less than the circumference of tube 1002, that is L2<=D2*PI (approx. 3.1415), so that important printed material on section 1116 is not covered over as label 1110 is wrapped around tube 1002. As previously mentioned in some cases (L0+L1+L2)< (D2*PI−2 mm) to ensure a visual gap is provided between distal end 1117 and adhered end 1119.

Label 1110 can include preprinted bar code 1122 which can be used to identify the type and size of container 1100. The type data can include information identifying special reagents that are in container 1100. Bar code 1122 can also be a unique serial number that can be used to identify container 1100, although in that case determining what type of container it is may require communication with a database to map the serial number to container type information or bar code 1122 may include both a unique number and identify the type of container.

Label 1110 is typically preprinted with other text 1124 describing the manufacturer, the purpose it is to be used for, the container size, expiration date, and any other pertinent data. In many cases cap 1006 is colored 1007 to indicate a specific purpose. Typically label 1110 has colored indicia 1125 to match color 1007 of cap 1006. Label 1110 also has print area 1116, where text and or bar code information can be printed regarding specific information relating to the blood sample being collected. For example this may include the patient name 623 from whom the blood was collected, the time, the healthcare worker who collected the sample. In some cases this information is correlated to a unique serial number bar code that is printed on label 1110 and the other text information is transferred to a database by wireless communication, for example using 802.11 or cellular communication standards. In either case the information about the collected sample and container 1100 are associated with each other.

Label 1110 can also be configured with an electronic memory or tag 1130, for example an RFID tag. Tag 1130 may be used with or instead of bar code 1122. In some cases tag 1130 may only be read, while in other cases it can be written to and read.

It is anticipated that label 1110 will be wrapped around tube 1002 for shipping, but not adhered and freely extended for use.

FIG. 37 shows another embodiment of label 1110. Clear overcoat section 1134 has been added to label 1110. Section 1134 is of length L3 and height H3 and has distal end 1136 and the back surface is at least partially coated with a transparent adhesive (not shown) protected by release liner 1120. In this embodiment of label 1110, sections 1114 and 1116 need not have any adhesive.

The purpose of section 1134 is to protect information printed on section 1116 from wear, solvents or damage. By removing release liner 1120 the healthcare worker can wrap label 1110 around tube 1002. Section 1134 is designed so it will wrap over any important printed material on section 1116. FIG. 38 shows distal end 1136 of section 1134 extending beyond distal end 1117 of section 1116. It is anticipated that L3 will be equal to or larger than the circumference of tube 1002, such that L3>=D2*PI, however, it may be shorter. Overcoat section 1134 being transparent allows the contents of container 1100 to be seen when a gap is to be maintained be maintained between distal end 1117 and the attached end of label 1110.

When desired section 1134 height H3 is greater than H1, so when section 1134 is wrapped around tube 1002 overcoat section 1134 completely covers section 1116, encapsulating section 1116 while leaving text 1124 and print area 1126 visible for reading or bar code recognition.

FIGS. 39 to 42 show information device or printer assembly 1150 with housing 1151 which may be hand held or incorporated as part of a portable cart or tray. Information device 1150 has most of the components shown in FIG. 11 as well as having wireless communication module 1152 (using for example a 802.11 or cellular communication standard), machine code reader 1154 (for example a bar code reader, magnetic strip reader, or an RFID reader or reader/writer), printer 1156, and internal RFID tag reader/writer 1184 all in communication with processor 50. Bar code reader 1154 may be external to housing 1151 connected by a cable or it can be a separate device that communicates with processor 50 like identification device 320, a handheld code reader or a conventional PDA.

Housing also has opening 1160 sized to accommodate tube 1002. Opening 1160 is formed by walls 1161 in housing 1151 so as to laterally support tube 1002. In some cases opening 1160 is designed to prevent cap 1006 from entering opening 1160, so that ledge 1104 rests on the top of housing 1151 when tube 1002 is inserted in opening 1160 (see FIG. 40). Walls 1161 may be elongated so as to allow a variety of different length tubes 1002 to be placed in opening 1160 so that ledge 1104 rests against the top of housing 1151. In this manner the top edge of label 1110 is always positioned properly relative to printer 1156 by distance H2.

Projecting from opening 1160 is slot 1162 designed to allow label 1110 to pass into housing with tube 1002. When label 1110 is long, for example when it uses overcoat section 1134, label 1110 can pass through slot opening 1164, allowing for a variety of labels to use used with device 1150.

Printer 1156 is positioned within housing 1151 and can use any of the conventional printing techniques such as ink jet, thermal, thermal transfer, or when label 1110 is constructed of electronic paper, such as from e-Ink Corp. or the like, printer 1156 is an interface used to program or "print" to the electronic paper. Note, when electronic paper is used label can be "printed" to externally from housing 1151, or by connection to a connector (not shown) on device 1150.

Figure 41:
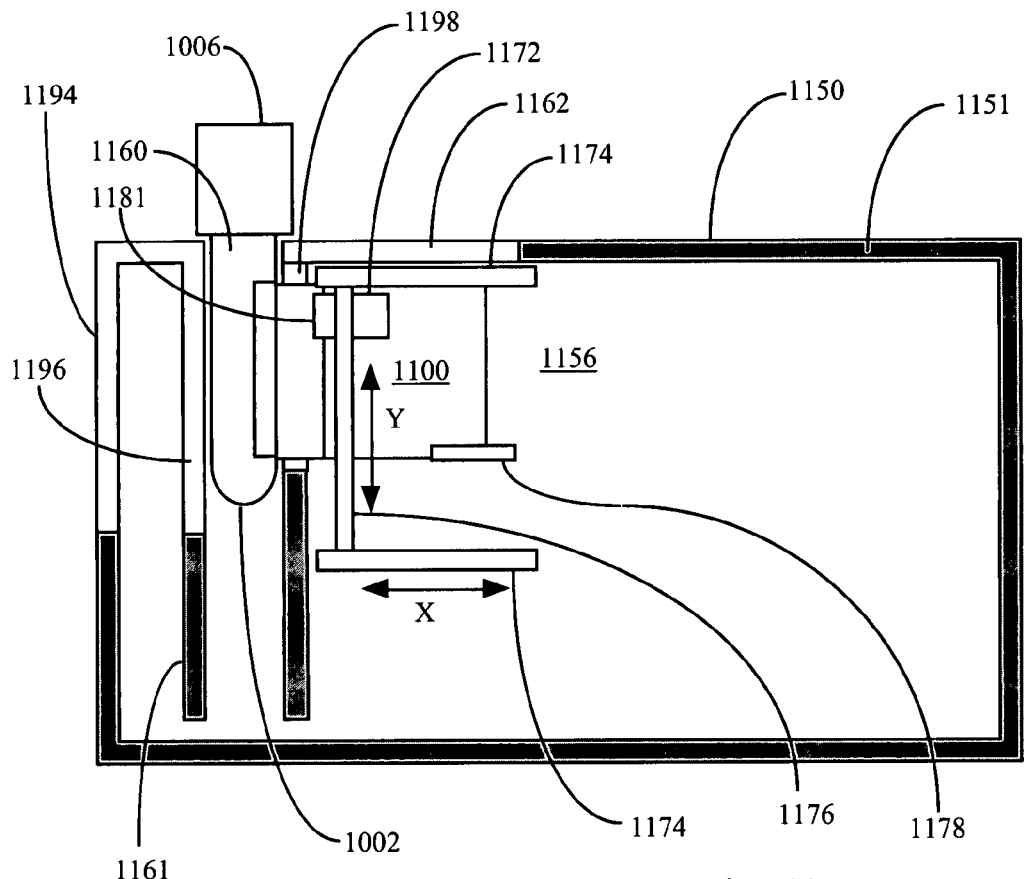
FIG. 41 is a sectional diagram of the printer of FIG. 40 showing a container with partially attached label positioned for printing.
Figure 42:
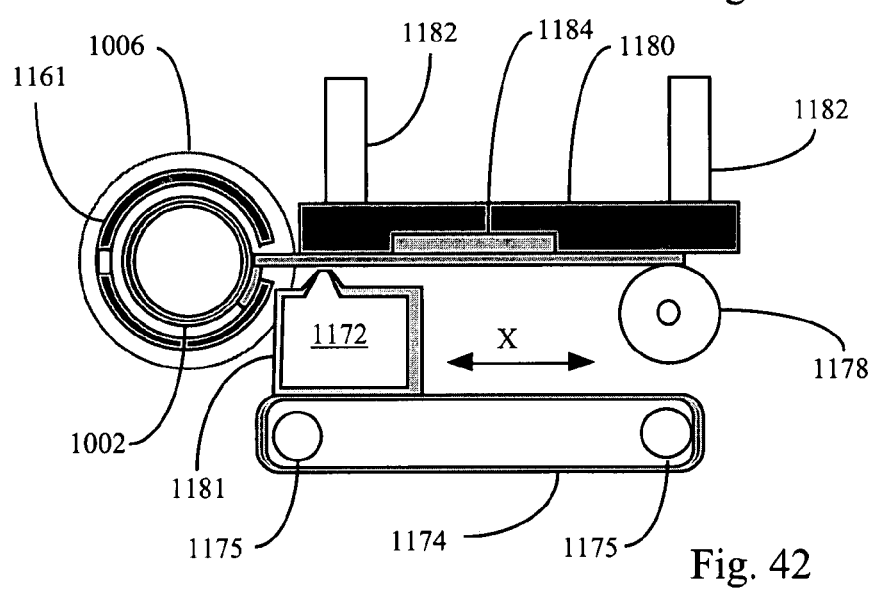
FIG. 42 is another enlarged cross sectional diagram of the printer mechanism of FIG. 40 with partially attached label positioned for printing.
Figure 43:
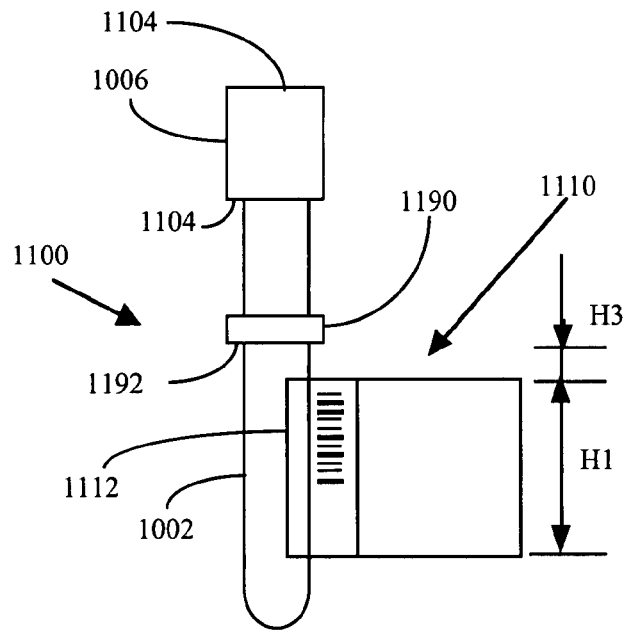
FIG. 43 shows a container with a partially attached label and a physical characteristic to position the label properly for printing.

Printer 1156 is shown in more detail in FIGS. 41 and 42. Now visible are print head 1172 (for example an inkjet cartridge), drive belts 1174 and 1176 driven by drive gears 1175. In this manner print head 1172 can be swept in an X-Y motion across front surface 1118 of print area 1126 of section 1116. Tension roller 1178 is used to pull a portion of label 1110 so that it remains flat and to draw label 1110 fully into printer 1156. Supporting the back side of label 1110 is plate 1180 which may be under pressure from springs 1182. Some print technologies such as thermal printing do not require both X and Y movement.

Most printer assemblies need a specific clearance between leading edge 1181 of printer 1156 and wall 1161 of inserted tube 1002. This distance may be equal to L1 of spacer section 1114, an area where the printer is not able to print when label 1110 is attached to container 1100.

RFID reader/writer 1184 is shown as part of plate 1180, but may be positioned elsewhere and can when desired be on the exterior of housing 1151, for example reader (/writer) 1154.

In some cases an accessory ring 1190 with underside ledge 1192 may be placed around tube 1002. This can also be arranged distance H3 above label 1110, so that when a very long tube is placed in opening 1160 ledge 1192 rests on the top surface of housing 1151. In this case the position of label 1110 relative to printer 1156 is maintained. However, other physical characteristics of container 1100 can be used to ensure label 1110 and printer 1156 care aligned.

It is anticipated that, in at least some embodiments, a label may be pre-wrapped around and adhered to tube 1002. In this case, printer 1156 may be designed to print to print area 1126 while tube 1002 is rotated by drive rollers or the like. Preferably an alignment indicia such as a preprinted marker or a physical detent can be used to indicate to printer 1156 the orientation of label 1110 in printer 1156 so the printed text and/or codes are properly printed along label 1110. However as before the label 1110 is precisely positioned vertically relative to a fixed physical aspect of container 1100.

While not shown information device 1150 can be equipped to rotate container 1100 from the bottom, as opposed to radially, to ensure proper mixing of the blood sample with the reagent in cases where the blood sample is added to the reagent prior to printing activity. In some cases the number of rotations is determined by reading a code or other indication printed on label 1110 by the manufacturer.

Operation of Container Label Printer

In at least some embodiments, operation of device 1150 in many aspects parallels that of device 190 of FIG. 10 and device 100 of FIG. 34, with a few extra steps.

Figure 44:
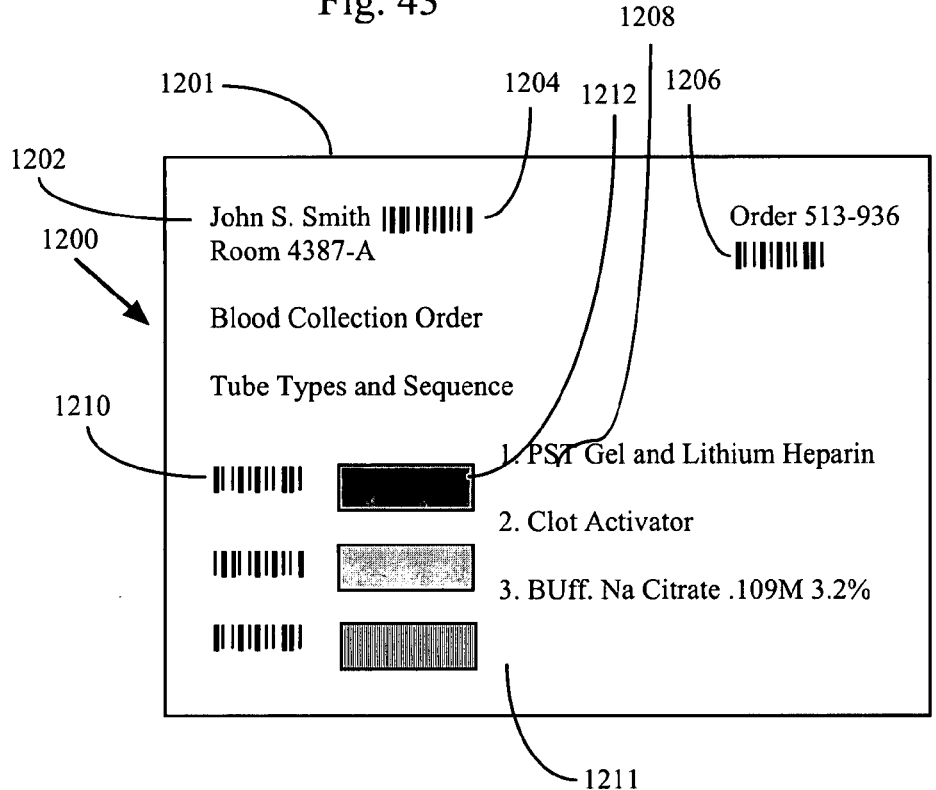
FIG. 44 shows a sample medical order for a specimen to be collected.

Referring again to FIG. 12, a work order for a blood sample may be entered at workstation 220 or the like and stored in database 264. Referring to FIG. 44, the work order can be printed as a blood collection work order 1200 on paper sheet 1201 and given to a healthcare worker. Exemplary work order 1200 includes a patient's name or identification number 1202, a corresponding patient identification bar code 1204 and an order bar code 1206. In at least some embodiments bar code 1204 is not a direct match for the patient identification number 622 found on identification device 300, so code 1204 cannot be accidentally read instead of bar code 319 or reading 318 (see FIG. 14) to obtain the patient identification number. For example, code 1204 may be the patient identification number 622 in reverse order or with an "X" preceding the number.

Also printed on the paper sheet is a list of the types of blood collection containers where the list specifies container type via text 1208 and bar code 1210 as well as via a color code 1212 (assuming work order 1200 is printed using a color capable printer) that matches the color code 1007 of a cap 1006 of an appropriate container 1100 (i.e., the container with the appropriate reagent for a specific test). The container list is presented in a specific sequence (see numbers 1211) that indicates the appropriate sequence in which blood should be drawn by the healthcare worker (i.e., the printed sequence should be used by the healthcare worker as a guide in the proper sequence selection of blood tubes 1100).

Not all the information or bar codes described above need to be printed on order sheet 1201 and additional information not discussed can be provided. For example, order bar code 1206 can be read and the other information can be retrieved by device 1150 using wireless module 1152 in communication with database 264.

In some embodiments work order sheet 1201 need not be printed. Instead device 1150 using reader 1154 can be used to read specific patient information 621 from patient identification device 300 and communicate information 621 to database 264 using wireless module 1152. Upon receiving a patient identifying number, database 264 or a processor associated therewith can then search for work order 1200 corresponding to specific patient information 621 and communicate work order 1200 to device 1150.

In the present example, after one or more blood tests have been ordered for a patient, a healthcare worker with container(s) 1100 and an exemplary information device 1150 proceeds to the patient's room. The healthcare worker uses reader 1154 to read the bar codes 1204, 1206, and 1210 from the paper identifying the patient, the order and the types of containers to be used to draw blood.

The worker then uses reader 1154 to read bar code 319 from the wrist band or the like on the patient's wrist to determine if the patient in the room corresponds to the order on the sheet 1201. If the patient in the room does not correspond to the order on the sheet, the worker is advised to locate the correct patient. When the patient in the room matches the order on the sheet 1201, the worker uses sheet 1201 or display 34 to determine the types of containers into which blood is to be collected and the sequence in which the container types are to be filled with blood. The worker selects the appropriate containers 1100 from a stock on hand (for example in a cart, wall dispenser, cupboard, or tote). Using the color codes 1212 printed on the sheet 1201 greatly helps worker in selecting the correct containers 1100. When display 34 is a color display it can present the color matching the container cap color 1007 as well. The worker then uses reader 1154 to read bar code 1122 from the tag 1110 (see FIG. 35) on the selected container 1100. Device 1150 then determines if the code read corresponds to the type of tube in order 1200 and if it has been read in the correct sequence. If the code 1122 does not match the container type on the order 1200 and the sequence of containers on the order, an alert is presented to the healthcare worker using display 34 or device 18. If the container type and order are consistent with the order 1200, the worker draws the blood sample from the patient into container 1100.

Container 1100 is then inserted into opening 1160 and the unattached sections 1114, 1116, and 1134 (when provided) are inserted into slot 1162 of device 1150. Once again bar code 1122 can be read, now by an internal machine code reader (not shown) to determine that container 1100 corresponds to blood sample work order 1200 and an alert is presented if the container type does not match the work order. RFID reader 1184 (see FIG. 42) can also be used for this purpose.

Next, printer 1156 is activated, for example by pressing button 194. Printer 1156 can use roller 1178 to pull label 1110 tight into printer 1156, plate 1180 can be pressed against label 1110 by springs 1182 and print head 1172 is passed across surface 1118 so that appropriate text and bar codes can be printed to print area 1126. In some cases the printed information applied to area 1126 will include the name and an identity bar code associated with the patient from which blood was drawn, a blood sample identifier corresponding to a specific order, the current date and time from clock 66, healthcare worker identity 683, the ordering physician, etc. In some cases, RFID tag reader/writer 1184 can be used to write order information to RFID tag 1130 along with or instead of using print head 1172.

In yet another embodiment a handheld code reader, device 320 or PDA (person digital assistant not shown) equipped with reader 1154 can be used to read information from identification devices 300 and/or 320, order codes 1204, 1206, 1206, as well as bar code 1122 or tag 1130. The handheld code reader can be used to perform any comparisons against the blood collection order or can communicate wirelessly with database 264 or a remote processor to perform any comparisons. Various indicators can be used to indicate to the healthcare worker the status of the comparisons. The PDA can then transfer information about the patient, healthcare worker, containers 1100, and work order 1200 to device 1150 to complete the step of printing label 1110 when container in inserted in opening 1160.

After comparisons and printing and/or writing, container 1100 is removed from device 1150, release liner 1120 is removed and sections 1114, 1116, and 1134 (when provided) are wrapped around tube 1002. The next container 1100 on the order list (see FIG. 44) is obtained, confirmed using device 1150, used to collect blood, labeled via device 1150 and so on. After blood has been drawn into each of the containers on the order list and each container has been properly labeled, the labeled containers 1100 are sent to the lab for processing.

In an alternate embodiment, after at least one order for a blood test has been generated for a patient, a healthcare worker uses device 1150 to access the order via wireless module 1152 and, upon receiving the order, goes to the patient's room to collect the blood sample. Once in the patient's room the worker uses reader 1154 to read bar code 319 from the patient's identification device or memory contents 620 via device 318. Specific patient information 621 gathered is used to re-access the patient blood collection work order 1200 either already stored in memory 62 or to again obtain the order from database 264 using wireless communication module 1152. The specific types of containers 1100 are identified in work order 1200 and the worker presents the correct containers 1100 to reader 1154, is provided with an indication that the containers match work order 1200 (e.g., via display 34), collects the blood, and inserts containers 1100 into opening 160 for printing as described above.

It should be noted that the printing operation ensures that label 1110 is always in a fixed position relative to cap 1006 or to another positioning limiter, for example ring 1190 or the tip of tube 1002. This guarantees that the processing lab system gets precisely positioned labels 1110 on containers 1100 and that labels 1110 correspond to the types of containers used for specific orders.

The above processes also ensure that the information printed in print area 1126 or recorded to tag 1130 is correct. As an extra precaution, a timer can be activated by using clock 66 to ensure that the time that passes between the first activity of processing an order (for example reading a patient identifier 320 or reading order 1200) and the last activity (for example printing label 1110) must take place within a specific threshold period of time, for example within 3 minutes plus 30 seconds for each additional container used. If the time period exceeds the threshold period of time, an alert can be presented to the healthcare worker and the patient identification device 300 may have to be reread to prevent any chance for blood to be mislabeled for the wrong patient. Here, the alert may be either audible, visual (i.e., a blinking LED or a message via display 34) or a combination of both.

Device 1150 can be used to print information to unattached section 1116 of label 1110 attached at section 1112 to a medical glass slide, a plastic bio-chip, or diagnostic assay tray 1213 (see FIG. 45) to identify a specific patient from whom a sample was collected. Slide 1213 has front surface 1214 and rear surface 1215. Slide 1213 can be printed by inserting it and label 1110 into slot 1194 of device 1150 allowing label 1110 to extend into printer 1156 so front surface 1118 of label 1110 can be printed and tag 1130 written to as seen in FIG. 46. While slot 1194 is designed to let slide 1213 be passed into it, slot 1198 is designed to prevent slide 1213 from entering printer 1156 by being undersized compared to the dimensions of slide 1213.

When release liner 1120 (if provided as sections 1114 and 116 need not have any adhesive applied to them) is removed, label 1110 can be wrapped around and adhered to surface 1215. It should be noted that sections 1114 and 1116 are dimensioned such that, when wrapped around and attached to slide 1213, do not cover, obscure, or interfere with any of the sensing features of slide 1213, for example electrical contacts 1216, optically transparent section 1217, sample cells 1218, etc.

Figure 45:
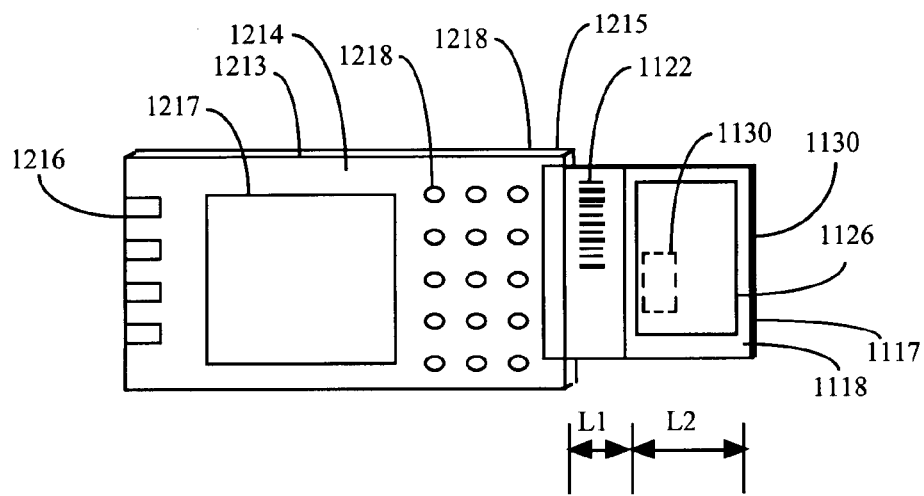
FIG. 45 shows a medical slide with a partially attached label.
Figure 46:
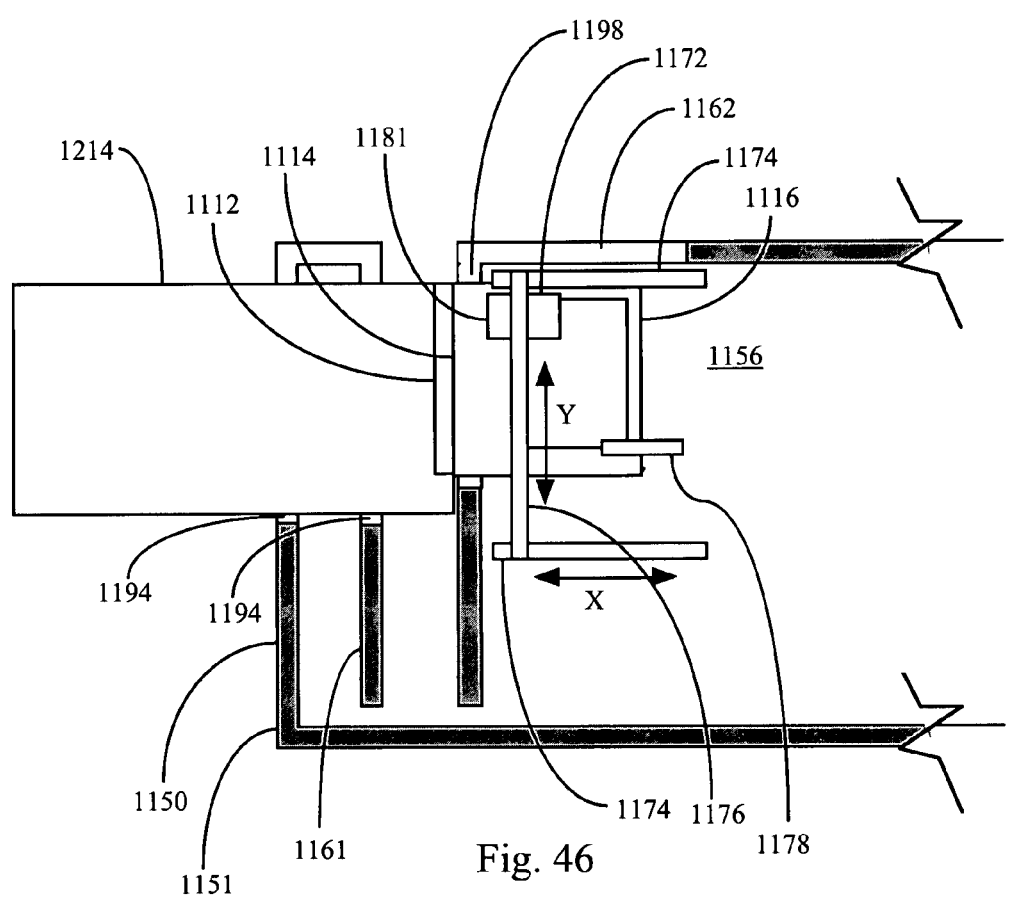
FIG. 46 is a sectional diagram showing the medical slide of FIG. 45 inserted into the printer of FIG. 40.

As in the case of the containers above, work order 1200 information can be compared with bar code 1122 or tag 1130 information in FIG. 45 to determine that tray 1213 is the correct type of slide 1213 or assay to be used for the order. Also a portion of patient information 621, healthcare worker information 681, and the date/time can be printed on label 1110 or recorded to tag 1130.

Advanced Container Selection and Labeling System

Figure 47:
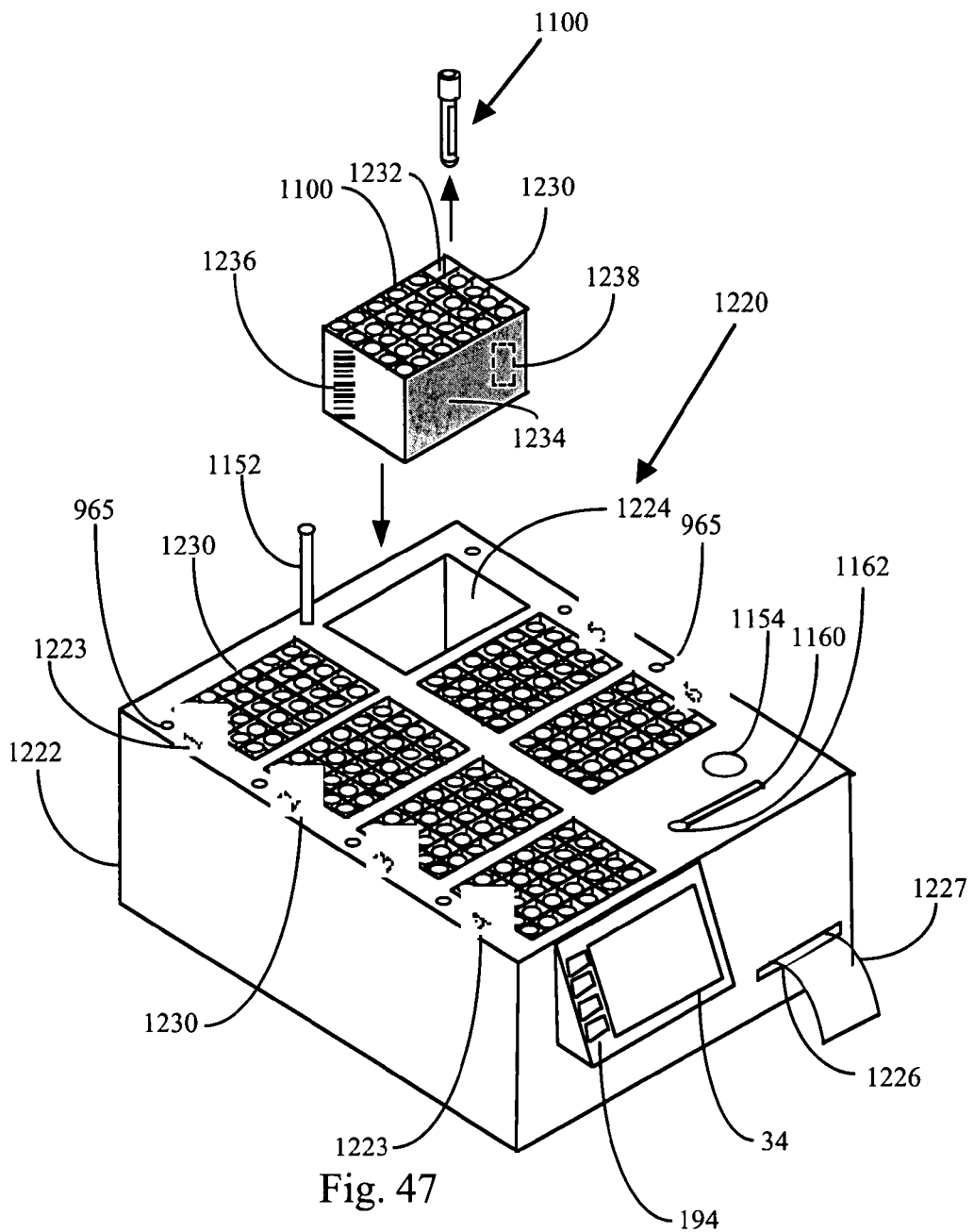
FIG. 47 shows medical specimen container selection and labeling system.

FIG. 47 shows another exemplary information device or container selection and labeling system 1220. System 1220 is similar to device 1150, but is equipped with several additional features. System printing device 1222 can either be carried by hand, be part of a cart, or installed in a fixed location. Device 1222 has one or more package recesses 1224 and a machine code reader 1154 and forms an opening 1160 and slot 1162 for receiving container 1100 and label 1110 for printing/ writing in a fashion similar to that described above with respect to device 1150. Device 1222 further includes a processor and memory (not shown but akin to the processor 50 and memory 62 illustrated in FIG. 11 above) and may include a printer 1226 for printing paper documents such as work orders 1200. In some cases printer 1226 may be used instead of a printer 1156 to print secondary adhesive label 1227 that is adhered to tube 1002. Label 1227 can be used instead of section 1116 and can be printed with a color code to match the color code 1125 of the container 1100 to which it is to be adhered to.

Exemplary device 1222 further includes display 34, button 194, indicator lights 965 adjacent to and for identifying each recess 1224 or its location, and a wireless communication module 1152. All these electronic components are in communication with the device processor.

Recess 1224 is designed to receive package 1230 holding multiple containers 1100 of a similar type (i.e., including the same reagent). Each recess can be identiifed using indicator lights 965 or printed label or recess identifier 1223. Package 1230 can be divided into separate cells 1232 to house individual containers 1100. For maximum packing density it is assumed that label 1110 is rolled around, but not adhered to the wall of tube 1002. To identify the types of containers 1100 in packages 1230 the walls of the packages can be color coded 1234 to match the colors 1125 of caps 1006, have text identifying container 1100 type, and bar code 1236 and/or RFID tag 1238 also to identify package 1230 to device 1222.

When package 1230 is inserted into recess 1224 device 1222 can read bar code 1236 or RFID tag 1238 using a reader (not shown) in the interior of opening 1224. Alternately bar code 1236 or RFID tag 1238 can be read by reader 1154 and button 194 can be used to identify which recess 1224 package 1230 is being placed into. In this manner device 1222 can determine which type of container is housed in package 1230 placed in any of the different recesses 1224. Device 1222 can also determine the inventory of container 1100 in package 1230 by using bar code 1236 or RFID tag 1238 to obtain an initial quantity and then monitoring usage of containers 1100 of each specific type to deduct from the initial quantity maintained.

Containers 1100 that are rarely used and therefore not justifying a separate package 1230 may be housed in a separate drawer or other carrier.

Labeling system 1220 can be used much like device 1150. The system 1220 processor receives an order, for example via wireless communication module 1152 in communication with database 264 or by using reader 1154 to read order sheet 1201. Reader 1154 is used to read patient device 318 or bar code 319 to determine that the patient selected matches the patient corresponding to the order.

As discussed above a handheld code reader or a PDA with reader 1154 can be used to obtain patient, healthcare worker, and container information that are transferred to device 1222. Device 1222, after receiving work order 1200, can verify that specific patient information 621 matches patient identification code 1204. When there is no match, device 1222 provides an alert. When a match occurs, device 1222 may provide a verification signal.

Device 1222 then determines types of containers 100 that need to be selected according to the order. Device 1222 can use display 34 to indicate which containers 1100 are to be use and in what sequence and present a color code corresponding to the container color code 1125. When device 1222 maintains a list of what packages 1230 have been inserted into recesses 1224 (for example by reading bar code 1236 or RFID tag 1238), device 1222 can indicate that one or more containers 1100 is to be removed from a specific package 1230 by using display 34 in conjunction with activating the indicator 965 adjacent to the correct package 1230.

The healthcare worker removes the appropriate container 1100 from package 1230 or from a separate drawer and uses reader 1154 to read bar code 1122 or RFID tag 1130 to identify each container 1100. If a match occurs, the worker obtains the blood sample in the container. If a match does not occur, an appropriate alert is presented to the worker via device 1222. An alert can also be presented if the wrong type of container 1100 is selected or selected out of the recommended sequence.

After obtaining the blood sample container 1100 is placed in opening 1160 and label 1110 in slot 1162 for printing as described for device 1150. It is anticipated that device 1222 may also remove release liner 1120 and automatically rotate container 1100 so that label 1110 is wrapped and adhered to tube 1002.

It is also anticipated that device 1222 can rotate container 1100 about a substantially vertical axis so as to mix the blood sample with the reagents of container 1100. The number of rotations can be determined by information printed on label 1110.

Medication Container Labeling

FIGS. 48 to 50 show a medication container labeling system. FIG. 48 shows medication container 1250 with attached label 1110 where the container does not include a cap (a cap may be provided). Label 1110 is attached by section 1112 and has spacer section 1114 and print section 1116. As above, adhesive is applied to at least a portion of the back surface of label sections 1114 and 1116 and the adhesive is protected by a release liner 1120.

Bar code 1122 can be preprinted on label 1110 to identify the type of container, its shape, size, or other characteristics associated with the container. Label 1110 can also have a memory tag 1130, for example an RFID tag, attached to it. Label 1110 may also have optional flag labels 1256 and 1258. Labels 1256 and 1258 can be printed with special instructions concerning specific medications or dosing regimens. Labels 1256 and 1258 are separated from section 1116 and can be removed individually and applied to container 1250 as needed after or before sections 1114 and 1116 are wrapped around and adhered to container 1250. Labels 1256 and 1258 may also be color coded to attract attention (e.g., red for caution).

Container 1250 has a diameter of D3 and section 1116 has a length of L2 such that L2<D3*☐ so section 1116, when wrapped around container 1250, does not cover over any of the printed text.

FIG. 49 shows printing device 1260 similar to device 1150 with all or most of the same electronic elements of device 1150. In this example, medication may be dispensed into container 1250 according to a work order 1200. Either before, while, or shortly after filling interior 1252 of container 1250 with medication 212, unattached sections 1114 and 1116 are inserted into slot 1162 and printer 1156 will print information (for example selected patient information 520 and/or selected medication dose information 540) in print section 1116 to identify the medication in container 1250, the patient for whom the medication was dispensed, the dosing regimen, etc. Bar code 1122 or tag 1130 can be read by reader 1154 or by an internal reader to determine that the medication being dispensed is appropriate to be dispensed into container 1250, for example that the quality of medication fit in interior 1252.

Text and bar codes can be printed to print section 1116 and tag 1130 can be written to by device 1260. Label 1110 is then removed from slot 1162. Release liner 1120 is removed from the adhesive coated back surface of label 1110, allowing sections 1114 and 1116 to be wrapped around and adhered to the side walls of container 1250. Flags labels 1256 and 1258 are removed as appropriate and attached to container 1250 so that they do not obscure printed text on section 1116.

Device 1260 can also used to print labels 1110 for blister packs, medication bottles, or box packaged medication. It is anticipated that container 1250 could be placed in an opening similar to opening 1160 of device 1150 (not shown in FIGS. 49 and 50) and printed.

In some cases it is also anticipated that label 1110 can be pre-wrapped and attached to container 1100. When device 1260 has opening 1160 so container 1100 can be inserted in opening 1160 allowing printer 1156 to print label 1110 while rotating container 1250 (or 1100) using friction rollers, a mandrel, or vacuum disk to print on surface 1118. In this case a registration marker or physical characteristic can be used to align printer 1156 to label 1110.

Figure 51:
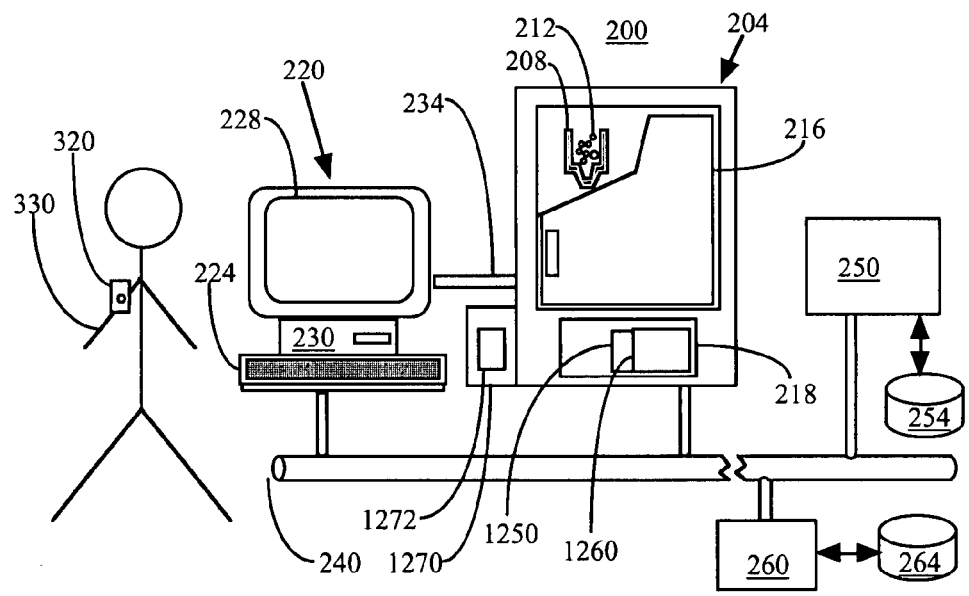
FIG. 51 shows a medication dispensing system of FIG. 12 modified to print the labels of a medication container.

FIG. 51 shows dispenser 204, previously seen in FIG. 12, now modified with container 1250 placed in access port 218 and being filled with medication 212. Label 1110 has been inserted in device 1260 which is under control of dispenser 204, so text and bar codes can be printed on section 1116. RFID tag 1130 can be written to as well or in other instances can be read as a unique serial number and stored in database 264 along with the prescription regimen for a specific patient that can later be obtained by a remote tag reader (for example at the patient's home) reading tag 1130 and communicating with database 264.

Ancillary printer 1270, also under control of dispenser 204, can print medication instructional sheets 1272 as needed.

Object Labeling in Other Fields

Figure 52:
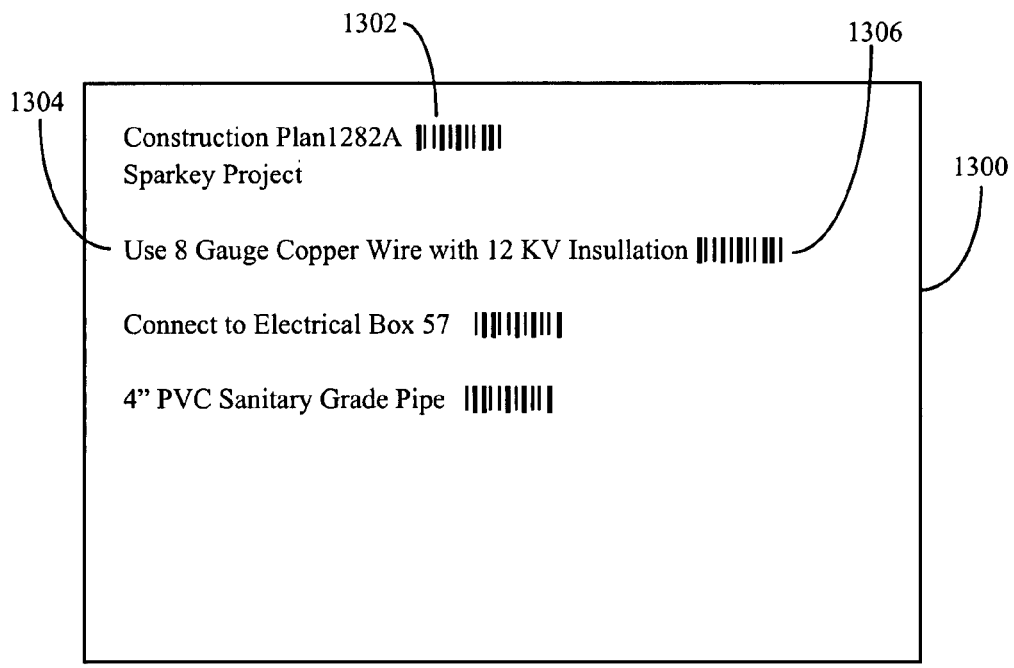
FIG. 52 is a construction plan.

The use of the present invention is not limited to the medical field or for use only with containers. For example FIG. 52 shows a work order in the form of a construction plan 1300, for example a product assembly diagram or architectural plans. The work order includes a plan bar code 1302, similar to order bar code 1206, the sequence of construction assembly events, and the specifications 1304 of the material grade or type that is approved for use as well as a corresponding material bar code 1306. The specifications may be a wire size, a pipe size and strength, a cable type, an approved connector, ASTM designation, or other product characteristics.

Figure 53:
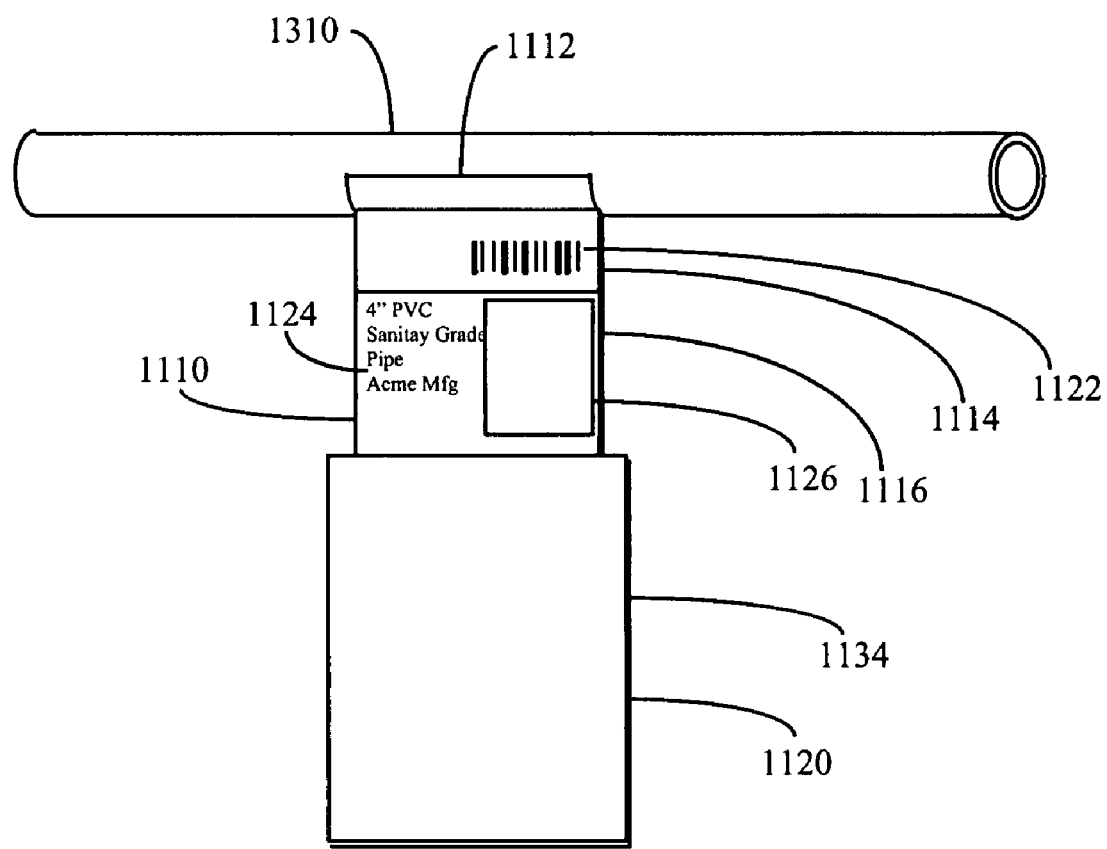
FIG. 53 is an object identified by a partially attached label to which text and bar codes can be printed.

FIG. 53 shows, by way of example, object 1310 (for example a pipe) with label 1110 attached to it, although label 1110 may be completely adhered to object 1310. Label 1110 has a bar code 1122 printed on it, and readable text, both of which can identify the size, quality, manufacturer and part number of the associated pipe. Alternately, some or all of the information that can be printed on label 1110 may be preprinted on the exterior of object 1310, for example a pipe. For long objects labels 1110 may be attached to the objects 1310 every 5 feet or reprinted on the exterior surface of object 1310 every 2 feet, allowing object 1310 to be cut to a required length for installation, yet preserving the contents of label 1110.

To follow plan 1300, worker can use device 1150, device 320 or a PDA equipped with a bar code reader to read material codes 1306. Next, the worker can read bar codes 1122 from objects 1310. If an object code 1122 does not match a material code 1306 (albeit they may not be a perfect match to prevent reading material code twice so one may be preceded by an "X") on a plan or work order, an alert can be provided to the worker to not use the object 1310. If there is a match between an object code and a work order, device 1150, 320, or PDA can record the date and time when the match was made and affirm the worker in using the part associated with the matched code.

When an object includes a label 1110 with unattached sections 1114 and 1116, the unattached sections can be inserted into device 1150 or 1260 which can print the plan number, the date, worker identifier 681, and the material information from code 1122. As before, device 1260 can read bar code 1122 when label 1110 is inserted into slot 1162 to determine if there is a match. Other information can be printed on label 1110, for example designating a pipe as conveying hot water, oxygen, sewer discharge, direction of flow, etc. If desired release liner 1120 can be removed and label 1110 adhesively attached to object 1310.

Another step that can be followed is to read the bar code 1122 from the adjacent object 1310 to which object 1310 is being attached or with which the object is to be assembled. This additional step can be used to ensure that objects to be attached or assembled together are compatible for use with each other. When an incompatibility is identified, device 1150, 320, 1260, or a PDA with reader 1154 can present an alert. When no incompatibility occurs, approval information can be printed on label 1110 or linked to object 1310 via a bar code 1122 or a bar code printed on section 1116 linkable to database 264 to retrieve the other information about object 1310 and its use.

While the invention has been described with reference to a preferred embodiment, it will be understood by those skilled in the art that various changes may be made and equivalents may be substituted without departing from the broader aspects of the invention. For example, while the blood collection processes described above call for obtaining a blood sample prior to printing information on a label, in at least some embodiments, after confirmation that a container is the correct container for obtaining a blood sample for a specific patient and prior to obtaining the sample, information may be printed on the label and the label attached to the container.

What is claimed is:

1. A container label printing method comprising the steps of:
  a. providing a label having a first section and a second section spaced apart from the first section and oppositely facing front and back surfaces;

b. providing a container with an external surface;

c. securing the first section of the label to a portion of the external surface of the container with the second section of the label extends from the first surface;

d. providing a printer;

e. using the printer to print indicia on the front surface of the second section of the label; and f. securing the second section of the label to the external surface.

2. The method of claim 1 wherein the step of securing the first section of the label to the external surface of the container includes adhering the back surface of the first section of the label to the external surface.

3. The method of claim 2 wherein the step of providing a label includes providing a label with an adhesive on the back surface of the second section of the label and a release liner that covers the adhesive on the back surface of the second section and wherein the step of securing the second section of the label to the external surface further includes removing the release liner from the back surface of the second section and using the adhesive on the back surface of the second section to adhere the second section to the external surface.

4. The method of claim 1 wherein the step of providing a label includes providing a label having dimensions such that, after the first and second sections of the label have been secured to the external surface of the container, adjacent facing edges of the label are spaced apart so that at least a portion of the external surface of the container between the facing edges is uncovered by the label.

5. The method of claim 4 wherein the step of providing a container includes providing a cylindrical container where the external surface is a cylindrical external surface, the step of securing the first section includes securing the first section to a portion of the cylindrical surface so that the second section of the label can extend substantially perpendicularly from the cylindrical surface and the step of securing the second section of the label including the step of wrapping the section at least in part around the cylindrical external surface.

6. The method of claim 1 wherein the step of providing a printer includes providing a printer that forms an opening and a slot where the opening is dimensioned to receive the container and the slot is dimensioned to receive at least a portion of the label extending from the container wherein, when the portion of the label is received in the slot, the front surface of the received label portion is aligned with a printer mechanism of the printer.

7. The method of claim 1 wherein the second section of the label includes a printable section and a non-printable section wherein the non-printable section is located between the first section and the printable section.

8. The method of claim 1 wherein the step of providing a container includes providing a container for use in a specific testing operation and wherein the step of providing a label includes providing a label that includes a machine readable code that can be read by a machine where the code indicates the specific testing operation to be performed using the container.

9. The method of claim 1 wherein the step of printing includes printing at least one of human readable indicia on the front surface of the second section of the label, machine readable indicia on the front surface of the second section of the label, and writing to a memory device attached to the label.

10. The method of claim 1 wherein the step of providing a label includes providing a label that includes a third section where the second section is between the first and third sections and wherein the third section includes an at least partially transparent overcoat section, the method further including the step of applying the overcoat section over the second section of the label.

11. The method of claim 10 wherein the step of securing the second section of the label to the external surface includes using the overcoat section to secure the second section to the external surface.

12. The method of claim 10 wherein the step of providing a container includes providing a cylindrical container where the external surface is a cylindrical external surface, the step of securing the first section includes securing the first section to a portion of the cylindrical surface so that the second section of the label can extend substantially perpendicularly from the cylindrical surface and the step of securing the second section of the label including the step of wrapping the second section at least in part around the cylindrical external surface ands the step of applying the overcoat section over the second section including wrapping the overcoat section at least in part around the cylindrical external surface.

13. A container/label assembly for use in filling work orders that specify container types to be used to fill each order, the assembly comprising:

a container with an external surface;

a label having a first section and a second section spaced apart from the first section and oppositely facing front and back surfaces, the first section secured to the external surface of the container with the second section of the label extends from the first surface; and a container type identifier physically associated with the container, the type identifier including at least one of text, a machine readable code and a color indicia indicating the type of the container, wherein the container type is useable to verify that the container can be used to complete a work order.

14. The assembly of claim 13 further including an adhesive applied to the back surface of the second section of the label.

15. The assembly of claim 13 further including a removable release liner covering the adhesive on the back surface of the second section of the label.

16. The assembly of claim 13 further including a non-printable section between the first and second section of the label and wherein the front surface of the second section is printable.

17. The assembly of claim 16 where the container type identifier is presented at least in part on one of the first section and the non-printable section.

18. The assembly of claim 13 wherein the external surface has a girth and wherein the label includes a length that is less than the girth.

19. The assembly of claim 18 wherein the container is cylindrical, the external surface is a cylindrical external surface and the first section is secured to a portion of the cylindrical surface so that the second section of the label can extend substantially perpendicularly from the cylindrical surface.

20. The apparatus of claim 13 wherein the label includes a third section where the second section is between the first and third sections and wherein the third section includes an at least partially transparent overcoat section.

21. A method to properly complete a medical work order including the steps of:

a. providing a medical work order that specifies a type of container to be used to facilitate the order;

b. providing a container of a specific type where the container is at least substantially empty and the container includes a container type identifier identifying the container type and the container has an external surface;

c. securing a first section of a label to the exterior surface where the label has a second section that extends from the first surface; and d. filling the container according to the container type identifier.

22. The method of claim 21 further including the steps of:

e. using an electronic device to obtain the work order and the container type identifier;

f. comparing the container type specified by the work order with the container type identifier;

g. when the container type specified by the work order is the same as the container type identifier, indicating a match; and h. when the container type specified by the work order is different than the container type identifier, indicating that a different container type must be selected.

23. The method of claim 22 wherein the step of providing a medical work order includes providing an order that further specifies a patient associated with the work order, the method further including the steps of, prior to comparing the container type specified by the work order to the container type identifier, providing a patient identifier for a patient that may be associated with a work order, using the electronic device to obtain the patient identifier, comparing the obtained patient identifier with the patient specified by the work order, when the patient identifier is different than the patient specified by the work order, indicating that the wrong patient has been identified and, when the patient identifier matches the patient specified by the work order, performing steps (f) through (h).

24. The method of claim 23 further including the step of, when the container type specified by the work order is the same as the container type identifier, associating information with the container where the information specifies at least one of the patient associated with the work order and the work order.

25. The method of claim 24 wherein the step of associating includes one of printing the information that specifies the patient associated with the work order on a label and securing the label to the container and writing information to an identification device that is secured to the container.

26. The method of claim 24 further including the step of providing a container specific identifier on the container and wherein the step of associating includes correlating the information that specifies the patient associated with the work order with the container specific identifier and storing the correlated information in a database.

27. The method of claim 22 further including the steps of providing a container specific identifier on the container and, when the container type specified by the work order is the same as the container type identifier, further correlating the container specific identifier with the work order in a database.

28. The method of claim 22 where the step of comparing is performed by one of the electronic device, a remote computer, a PDA, or a printer used to record information on the container.

29. The method of claim 22 where the step of providing a medical work order that specifies a type of container to be used to facilitate the order includes printing the work order and wherein the step of using an electronic device to read the work order includes reading a code printed on the printed work order.

30. The method of claim 22 where the step of using the electronic device to obtain the work order includes receiving the work order by wireless communication.

31. The method of claim 22 further including the step of obtaining a biological sample from the patient and placing the sample in the container.

32. An apparatus for storing containers and for use with a database that stores at least a first work order that specifies a first container type to be used to facilitate the first work order, the apparatus comprising:

a. a carrier with at least first and second recesses, the first recess holding at least one of the first container type and the second recess holding at least one of a second container type;

b. a memory storing information that specifies the type of container in each of the recesses;

c. an output device; and d. a processor that is linked to the memory and the output device, the processor programmed to obtain the first work order from the database, identify the first container type specified by the work order and generate an output via the output device that indicates the first container type specified by the first work order.

33. The apparatus of claim 32 wherein the output device includes first and second light devices adjacent the first and second recesses and wherein the processor generates the output by illuminating one of the first and second light devices to indicate the container type specified by the first work order.

34. The apparatus of claim 32 wherein the output device is a display screen and wherein the processor generates the output by presenting at least one of human readable text, a recess identifier, and a color code corresponding to the container type via the display screen indicating the container type specified by the first work order.

35. The apparatus of claim 32 for use where the first work order further specifies a second container type for facilitating at least a portion of the first work order and wherein the processor provides output indicating each of the first and second container types.

36. The apparatus of claim 35 wherein the work order specifies that the portion of the first work order associated with the first container type should be completed prior to the portion of the first work order associated with the second container type and wherein the processor indicates the order in which the container types should be used via the output device.

37. The apparatus of claim 32 wherein each of the containers includes a container type identifier and wherein the apparatus further includes an identifier reader, the processor further programmed to, after a container type has been indicated via the output device, read a container type identifier that is proximate the reader, compare the identifier type to the container type indicated via the output device and, when the identifier type matches the container type indicated via the output device, indicate a match via the output device and, when the identifier type is different than the container type indicated via the output device, indicate that a different container is required to facilitate the work order.

38. The apparatus of claim 37 further including a printer for printing one of a label attached to the container, a label partially attached to the container and a label to be attached to the container with at least a portion of work order information.

39. The apparatus of claim 38 wherein the printer prints on a label.

40. The apparatus of claim 39 wherein the label is to be at least in part applied to the container after the printer prints the work order information on the label.

* * * * *